US011103557B2

(12) United States Patent
Kim et al.

(10) Patent No.: US 11,103,557 B2
(45) Date of Patent: Aug. 31, 2021

(54) EXENATIDE ANALOGUE AND USE THEREOF

(71) Applicant: ANYGEN CO., LTD., Gwangju (KR)

(72) Inventors: San Ho Kim, Gwangju (KR); Seon Myung Kim, Busan (KR); Moon Young Park, Gwangju (KR)

(73) Assignee: ANYGEN Co., Ltd., Gwangju (KR)

( * ) Notice: Subject to any disclaimer, the term of this patent is extended or adjusted under 35 U.S.C. 154(b) by 0 days.

(21) Appl. No.: 15/127,512

(22) PCT Filed: Mar. 23, 2015

(86) PCT No.: PCT/KR2015/002820
§ 371 (c)(1),
(2) Date: Sep. 20, 2016

(87) PCT Pub. No.: WO2015/142140
PCT Pub. Date: Sep. 24, 2015

(65) Prior Publication Data
US 2017/0128541 A1 May 11, 2017

(30) Foreign Application Priority Data
Mar. 21, 2014 (KR) ........................ 10-2014-0033712

(51) Int. Cl.
*A61K 38/26* (2006.01)
*A61K 9/00* (2006.01)
*C07K 14/605* (2006.01)
*A61K 47/54* (2017.01)
*A61K 47/61* (2017.01)
*A61K 38/00* (2006.01)

(52) U.S. Cl.
CPC ............ *A61K 38/26* (2013.01); *A61K 9/0053* (2013.01); *A61K 47/542* (2017.08); *A61K 47/61* (2017.08); *C07K 14/605* (2013.01); *A61K 38/00* (2013.01)

(58) Field of Classification Search
CPC .............. A61K 38/26; A61K 47/48038; A61K 47/4823; A61K 9/0053
See application file for complete search history.

(56) References Cited

U.S. PATENT DOCUMENTS

| 7,226,990 | B2 * | 6/2007 | Knudsen ................ A61K 38/26 530/300 |
| 7,888,066 | B2 | 2/2011 | Good et al. |
| 10,139,412 | B2 | 11/2018 | Vadasz et al. |
| 2004/0106547 | A1 | 6/2004 | Larsen et al. .................... 514/12 |
| 2007/0292387 | A1 | 12/2007 | Jon et al. ...................... 424/85.1 |
| 2011/0245165 | A1 * | 10/2011 | Larsen ............... C07K 14/57563 514/6.7 |
| 2011/0301084 | A1 | 12/2011 | Lau et al. ........................ 514/7.2 |
| 2014/0142037 | A1 | 5/2014 | Yue ................................ 514/7.2 |

FOREIGN PATENT DOCUMENTS

| CN | 1372570 A | 10/2002 | |
| CN | 1376166 A | 10/2002 | |
| CN | 101405301 A | 4/2009 | |
| CN | 102100912 A | 6/2011 | |
| JP | 2002-544127 A | 12/2002 | |
| JP | 2003-522099 A | 7/2003 | |
| JP | 2008-515857 A | 5/2008 | .......... C07K 14/575 |
| JP | 2011-102305 A | 5/2011 | ............. C07K 14/46 |
| JP | 2013-514976 A | 5/2013 | .............. A61K 9/28 |
| KR | 10-2007-0077428 | 7/2007 | ............. C07K 17/10 |
| KR | 10-2011-0007520 | 1/2011 | ......... C07D 207/452 |
| KR | 10-2014-0033023 | 3/2014 | ............... C07K 1/06 |
| WO | WO-9943708 A1 * | 9/1999 | .......... C07K 14/605 |
| WO | WO 0066629 A1 * | 11/2000 | ....... A61K 47/48215 |
| WO | WO 2009/035540 A2 | 3/2009 | ......... A61K 31/4743 |
| WO | WO 2009/035540 A3 | 3/2009 | ............. A61K 38/00 |
| WO | WO 2009/143285 A2 | 11/2009 | ............. A61K 38/22 |
| WO | WO 2009/143285 A3 | 11/2009 | ............. A61K 38/22 |
| WO | WO 2011/063549 A1 | 6/2011 | .......... C07K 14/575 |
| WO | WO 2011/084618 A2 | 7/2011 | ............... A61K 9/28 |
| WO | WO 2011/084618 A3 | 7/2011 | ............... A61K 9/16 |

OTHER PUBLICATIONS

Loretta L. Nielsen, Pharmacology of exenatide (synthetic exendin-4): a potential therapeutic for improved glycemic control of type 2 diabetes, Regulatory Peptides 117 (2004) 77-88.*
International Search Report (ISR) PCT/KR2015/002820, dated Jun. 15, 2015 published in WO 2015/142140.
Chae et al., (2010). "The fatty acid conjugated exendin-4 analogs for type 2 antidiabetic therapeutics", *Journal of Controlled Release*. 144(1):10-16.
Youn, Yu Seok, et al., (2013): "Long-acting inhalable chitosan-coated poly(lactic-co-glycolic acid) nanoparticles containing hydrophobically modified exendin-4 for treating type 2 diabetes", *International Journal of Nanomedicine*, 2013:8 2975-2983.
Extended European Search Report from corresponding European Application No. 15764055.8 dated Sep. 8, 2017.
Ahn, S., et. al. (2013) "Oral delivery of an anti-diabetic peptide drug viaconjugation and complexation with low molecular weight chitosan.", *J. Control. Release*, Sep. 2013, vol. 170, pp. 226-232.
Byetta, *Drug Label*, 2007.

(Continued)

*Primary Examiner* — James H Alstrum-Acevedo
*Assistant Examiner* — Erinne R Dabkowski
(74) *Attorney, Agent, or Firm* — Harness, Dickey & Pierce, P.L.C.

(57) ABSTRACT

The present invention relates to a novel exenatide analogue, which is an exenatide analogue in which the first to fifteenth amino acids from the C-terminal of the amino acid sequence of exenatide are deleted and a fatty acid is conjugated. The present invention provides a short length exenatide exhibiting almost the same level of anti-diabetic effects compared with that of conventional exenatide and liraglutide, which is an anti-diabetic drug, and capable of reducing the preparation cost of exenatide.

4 Claims, 51 Drawing Sheets

Specification includes a Sequence Listing.

(56) References Cited

OTHER PUBLICATIONS

Lee, C., et. al. (2014) "Decanoic acid-modified glycol chitosan hydrogels containing tightly adsorbed palmityl-acylated exendin-4 as a long-acting sustained-release anti-diabetic system.", *Acta Biomaterialia*, vol. 10, pp. 812-820.

Lee, J., et. al. (2012) "Self-assembled glycol chitosan nanogels containing palmityl-acylated exendin-4peptide as a long-acting antidiabetic inhalation system." *J. Controlled Release*, vol. 161, pp. 728-734.

Muranishi, S., et al. (1995) "Gastrointestinal absorption of used peptide pharmaceutical improvement.", *Drug Delivery System*, vol. 10, No. 1, pp. 21-30.

Office Action dated Aug. 15, 2017 in the foreign corresponding Japanese Patent Application No. 2017-5007874, with English Translation.

Office Action from corresponding Japanese Patent Application No. 2017-500787 dated Apr. 3, 2018, and its English translation.

Decision to Grant a Patent from corresponding Japanese Patent Application No. 2017-500787, dated Oct. 23, 2018.

Wang, M., et al. (2012) "Investigation of Transport Mechanism of Exendin-4 across Madin Darby Canine Kidney Cell Monolayers." *Biol. Pharm. Bull.*, 35(5):745-752.

Office Action from corresponding Chinese Patent Application No. 201580015260.9 dated Sep. 25, 2019 , with an English translation.

Kim et al. (2012) "Site-Specific PEGylated Exendin☐4 Modified with a High Molecular Weight Trimeric PEG Reduces Steric Hindrance and Increases Type 2 Antidiabetic Therapeutic Effects.", *Bioconjugate Chem.*, 23:2214-2220.

2nd Office Action of CN Patent Application No. 201580015260.9, dated Jul. 20, 2020, with English translation.

\* cited by examiner

EXENATIDE ANALOGUE AND USE THEREOF

FIELD

This application claims priority to and the benefit of Korean Patent Application No. 10-2014-0033712 filed in the Korean Intellectual Property Office on 21 Mar. 2014, the entire contents of which are incorporated herein by reference.

The present invention relates to a novel exenatide analog and a use thereof.

BACKGROUND

Exenatide, which is a functional analog of glucagon-like peptide-1 (GLP-1) isolated from salivary glands of *Heloderma suspectum* living in the American Southwest, has been used as a medicine for type 2 diabetes. Exenatide (scientific name: "Exendin-4") is a biological active peptide composed of 39 amino acids. The exenatide exists in the living human body, but the amino acids of the exenatide are 53% similar to those of GLP-1. The exenatide is stable against a degradation enzyme, such as dipeptidyl peptidase-4 (DPP-4), and thus the in vivo half-life thereof is relatively longer than that of GLP-1.

The exenatide is administered twice a day, prior to breakfast and dinner. Since the exenatide is excreted to the kidney, the use of the exenatide for patients with severe damage of kidney functions or end-stage renal diseases is not recommended. The excretion of exenatide is not dependent on the liver functions, and thus the exenatide does not have an interaction with a drug metabolized into the liver. The exenatide influences the gastric motility, and thus may cause an interaction with other drugs with respect to the intake thereof.

Moreover, the synthesis of exenatide peptides requires large quantities of reagents and excessive costs. Moreover, there are many reaction steps, intermediates need to be separated for respective steps, and the possibility of the generation of isomers is high, and thus exenatide is not easy to purify.

As set forth above, the disadvantages of existing exenatide, such as administration twice a day due to a short half-time thereof and expensive production costs, need to be solved. Therefore, research for methods for reducing the production costs while improving the stability and efficacy of exenatide may be very important in the pharmaceutical Industry field.

Throughout the entire specification, many papers and patent documents are referenced and their citations are represented. The disclosure of the cited papers and patent documents are entirely incorporated by reference into the present specification and the level of the technical field within which the present invention falls, and the details of the present invention are explained more clearly.

DETAILED DESCRIPTION OF THE INVENTION

Technical Problem

The present inventors have endeavored to improve the efficacy and stability of exenatide, which is a functional analog of glucagon-like peptide-1 (GLP-1) and is used as a medicine for diabetes, and a preparing method of exenatide. As a result, the present inventors have developed a short-fatty acid exenatide analog which has the same efficacy as conventional exenatide and exhibits high stability against peptidases, and thus have completed the present invention.

Accordingly, an aspect of the present invention is to provide an exenatide analog.

Another aspect of the present invention is to provide a pharmaceutical composition for alleviating, preventing, or treating diabetes.

Still another aspect of the present invention is to provide a pharmaceutical composition for alleviating, preventing, or treating obesity.

Still another aspect of the present invention is to provide a pharmaceutical composition for appetite suppression.

Other purposes and advantages of the present disclosure will become more obvious with the following detailed description of the invention, claims, and drawings.

Technical Solution

In accordance with an aspect of the present invention, there is provided an exenatide analog having 1 to 15 amino acid deletions in the C-terminal of the amino acid sequence of exenatide and including a fatty acid conjugated thereto.

The present inventors have endeavored to improve the efficacy and stability of exenatide, which is a functional analog of glucagon-like peptide-1 (GLP-1) and is used as a medicine for diabetes, and a preparing method of exenatide. As a result, the present inventors have developed a short-fatty acid exenatide analog which has the same efficacy as conventional exenatides and exhibits high stability against peptidases.

The exenatide is a GLP-1 receptor agonist and an analog mimicking GLP-1 (GLP-1 metrics), which is quickly degraded by dipeptidyl peptidase-IV (DPP-IV). The exenatide is a drug that is not quickly degraded by DPP-IV, promotes the secretion of sugar-dependent insulin, suppresses glucagon secretion, gastric emptying, and appetite, and exhibits a GLP-1 effect, showing the β-cell protecting effect.

In the exenatide analog of the present invention, the fatty acid may be conjugated to various locations of the amino acid-deleted exenatide. According to an embodiment of the present invention, the fatty acid may be conjugated to the Lys residue, N-terminal, or C-terminal of the amino acid-deleted exenatide. For example, the fatty acid may be conjugated to the Lys residue in the internal sequence of the amino acid-deleted exenatide, or may be conjugated to the N-terminal or C-terminal of the amino acid-deleted exenatide.

More specifically, the fatty acid is conjugated to the C-terminal of the amino acid-deleted exenatide.

The conjugation of the fatty acid to the amino acid-deleted exenatide includes all of a direct conjugation and an indirect linkage via a linker. A functional group of the fatty acid, such as a carboxyl group, reacts with a functional group (e.g., —NH$_2$) of the amino acid-deleted exenatide to form a covalent linkage, thereby forming an amino acid-deleted exenatide-fatty acid conjugate. According to the indirect linkage manner, a compound that is normally used as a linker in the art mediates the formation of the amino acid-deleted exenatide-fatty acid conjugate.

The linker used in the present invention may be any compound that is used as a linker in the art, and an appropriate linker may be selected according to the kind of the functional group of the amino acid-deleted exenatide. For example, the linker includes N-succinimidyl iodoacetate, N-hydroxysuccinimidyl bromoacetate, m-maleimidobenzoyl-N-hydroxysuccinimide ester, m-maleimidobenzoyl-N-hydroxysulfosuccinimide ester, N-maleimidobutyryloxysuccinamide ester, and Lys, but is not limited thereto.

Specifically, the linker may be further linked to the C-terminal of the amino acid-deleted exenatide, and the fatty acid is conjugated to the linker linked to the C-terminal. For example, Lys, as a linker, is linked to the C-terminal of the amino acid-deleted exenatide, and the fatty acid may be conjugated to the Lys. In this case, the —$NH_2$ group of the additional Lys may react with the carboxyl group of the fatty acid to form a conjugate.

According to an embodiment of the present invention, the exenatide contains: (i) exenatide having the amino acid sequence of SEQ ID NO: 1, and (ii) an exenatide analog exhibiting similar activity to the exenatide and having at least 80%, specifically 90%, and more specifically 95% sequence identity to the amino acid sequence of SEQ ID NO: 1. The exenatide of the present invention is, more specifically, exenatide having the amino acid sequence of SEQ ID NO: 1, and still more specifically, exenatide composed of the amino acid sequence of SEQ ID NO: 1.

The fatty acid, which is suitable for the exenatide analog of the present invention, includes various saturated fatty acids and unsaturated fatty acids known in the art.

Specifically, the fatty acid suitable for the present invention is a fatty acid having C3-C36 carbon atoms. For example, the fatty acid suitable for the present invention is selected from the group consisting of propionic acid, butyric acid, valeric acid, caproic acid, enanthic acid, caprylic acid, pelargonic acid, capric acid, undecylic acid, lauric acid, tridecylic acid, myristic acid, pentadecylic acid, palmitic acid, margaric acid, stearic acid, nonadecylic acid, arachidic acid, heneicosylic acid, behenic acid, tricosylic acid, lignoceric acid, pentacosylic acid, cerotic acid, heptacosylic acid, montanic acid, nonacosylic acid, melissic acid, henatriacontylic acid, lacceroic acid, psyllic acid, geddic acid, ceroplastic acid, and hexatriacontylic acid.

More specifically, the fatty acid suitable for the present invention is a fatty acid having C6-C16 carbon atoms, and the fatty acid is, more specifically, valeric acid, caprylic acid, pelargonic acid, capric acid, undecylic acid, lauric acid, tridecylic acid, myristic acid, pentadecylic acid, or palmitic acid; still more specifically, caprylic acid, pelargonic acid, capric acid, undecylic acid, lauric acid, tridecylic acid, myristic acid, pentadecylic acid, or palmitic acid; and still more specifically, caprylic acid, capric acid, lauric acid, myristic acid, or palmitic acid.

For example, an exenatide analog of the present invention, in which valeric acid, caprylic acid, capric acid, lauric acid, myristic acid, or palmitic acid is conjugated to the C-terminal of an exenatide having 9 amino acid residue deletions in the C-terminal thereof, may be prepared. Alternatively, an exenatide analog of the present invention, in which valeric acid, caprylic acid, capric acid, lauric acid, myristic acid, or palmitic acid is conjugated to the C-terminal of an exenatide having 7 amino acid residue deletions in the C-terminal thereof, may be prepared.

According to an embodiment of the present invention, the exenatide analog of the present invention is an exenatide in which valeric acid, caprylic acid, capric acid, lauric acid, myristic acid, or palmitic acid is conjugated, and more specifically, valeric acid, caprylic acid, or capric acid is conjugated to the C-terminal of an exenatide having 9 amino acid residue deletions in the C-terminal thereof. In these cases, the fatty acid may be conjugated to the C-terminal via a linker having an amino group (e.g., Lys linker).

According to an embodiment of the present invention, the exenatide analog of the present invention is an exenatide in which valeric acid, caprylic acid, capric acid, lauric acid, myristic acid, or palmitic acid is conjugated, and more specifically, valeric acid, caprylic acid, or capric acid is conjugated to the C-terminal of an exenatide having 7 amino acid residue deletions in the C-terminal thereof. In these cases, the fatty acid may be conjugated to the C-terminal via a linker having an amino group (e.g., Lys linker).

According to an embodiment of the present invention, the exenatide analog of the present invention may have 1 to 10 (more specifically, 4 to 10, and still more specifically, 7 to 9) amino acid deletions in the C-terminal thereof.

According to an embodiment of the present invention, the exenatide analog of the present invention further contains conjugated chitosan. Chitosan may be conjugated to various locations of the amino acid-deleted exenatide. The conjugation of chitosan to the amino acid-deleted exenatide includes all of a direct conjugation and an indirect linkage via a linker.

The exenatide analog of the present invention has almost the same stability and efficacy as the existing exenatide.

According to an embodiment of the present invention, the exenatide analog shows almost the same level of stability as the existing exenatide with respect to NEP24.11, which is a peptide degrading enzyme.

According to another embodiment of the present invention, the exenatide analog shows almost the same level of sugar tolerance as the existing exenatide in diabetic model mice.

According to still another embodiment of the present invention, the exenatide analog shows an excellent blood glucose reducing effect compared with the existing exenatide in diabetic model mice.

This effect of the present invention is more excellent and lasting in the blood glucose lowering compared with liraglutide, which is an anti-diabetic agent.

In accordance with another aspect of the present invention, there is provided a pharmaceutical composition for alleviating, preventing, or treating diabetes, containing, as an active ingredient, the exenatide analog of the present invention.

In accordance with another aspect of the present invention, there is provided a method for alleviating, preventing, or treating diabetes, the method including administering to a subject the pharmaceutical composition containing, as an active ingredient, the exenatide analog of the present invention.

The pharmaceutical composition containing, as an active ingredient, the exenatide analog of the present invention, can alleviate, prevent, or treat diabetes.

As used herein, the term "diabetes" refers to a chronic disease characterized by a relative or absolute shortage in insulin, causing glucose-intolerance. The term "diabetes" includes all types of diabetes, for example, type 1 diabetes, type 2 diabetes, or hereditary diabetes. Type 1 diabetes is the insulin-dependent diabetes, and is mainly caused by β-cell disruption. Type 2 diabetes is the insulin-independent diabetes, and is caused by an insufficient secretion of insulin after eating or by insulin tolerance.

According to an embodiment of the present invention, the composition is applied to alleviation, prevention, or treatment of type 2 diabetes.

In accordance with still another aspect of the present invention, there is provided a pharmaceutical composition for alleviating, preventing, or treating obesity, containing, as an active ingredient, the exenatide analog of the present invention.

In accordance with still another aspect of the present invention, there is provided a method for alleviating, preventing, or treating obesity, the method including administering to a subject the pharmaceutical composition containing, as an active ingredient, the exenatide analog of the present invention.

The pharmaceutical composition containing the exenatide analog of the present invention as an active ingredient can alleviate, prevent, or treat obesity. As used herein, the term "obesity" refers to a condition in which adipose tissues are excessively accumulated in the body so as to cause health disorders.

In accordance with another aspect of the present invention, there is provided a pharmaceutical composition for suppressing appetite, containing, as an active ingredient, the exenatide analog of the present invention.

In accordance with another aspect of the present invention, there is provided a method for suppressing appetite, the method including administering to a subject the pharmaceutical composition containing, as an active ingredient, the exenatide analog of the present invention.

As used herein, the term "suppressing appetite" refers to the suppression of a desire to take food.

The pharmaceutical composition of the present invention may be mainly administered to the human body in a parenteral administration manner. However, interestingly, as validated in the following examples, the exenatide analog of the present invention itself may be orally administered to exert treatment efficacy. According to an embodiment of the present invention, the pharmaceutical composition of the present invention is a composition for oral administration.

According to an embodiment, the pharmaceutical composition of the present invention further contains chitosan, wherein the chitosan is mixed with the pharmaceutical composition, but not covalently linked to the exenatide analog.

There is a prior art in which the covalent linkage of chitosan to insulin enables oral administration of insulin (see, Korean Patent Registration No. 0766820). However, according to the prior art, chitosan needs to be covalently linked to insulin, but the covalent linkage may cause a big problem in view of quality control in the production of medicines. Moreover, the prior art does not disclose exenatide.

As validated in the following examples, the simple mixing of chitosan with the composition containing the exenatide analog of the present invention shows excellent efficacy through the oral administration of the exenatide analog. Such results of oral administration of the exenatide analog are very interesting.

As used herein, the term "containing, as an active ingredient" refers to the inclusion of an amount that is sufficient to attain the efficacy or activity of the following exenatide analog. The quantitative upper limit in the composition of the present invention may be selected within an appropriate range by a person skilled in the art.

In cases where the composition of the present invention is prepared as a pharmaceutical composition, the pharmaceutical composition of the present invention contains a pharmaceutically acceptable carrier. The pharmaceutically acceptable carrier contained in the pharmaceutical composition of the present invention is usually used at the time of formulation, and examples thereof may include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil. The pharmaceutical composition of the present invention may further contain a lubricant, a wetting agent, a sweetening agent, a flavoring agent, an emulsifier, a suspending agent, a preservative, an in vivo absorption promoting agent, and the like, in addition to the above ingredients. Suitable pharmaceutically acceptable carriers and agents are described in detail in *Remington's Pharmaceutical Sciences* (19th ed., 1995).

The pharmaceutical composition of the present invention may be administered orally or parenterally.

A suitable dose of the pharmaceutical composition of the present invention may vary depending on various factors, such as the method for formulation, manner of administration, the age, body weight, gender, and morbidity of the patient, diet, time of administration, route of administration, excretion rate, and response sensitivity. The general dose of the pharmaceutical composition of the present invention is within the range of 0.001 μg/kg-100 mg/kg in adults.

The pharmaceutical composition of the present invention may be formulated into a unit dosage form or may be prepared in a multi-dose container by using a pharmaceutically acceptable carrier and/or excipient according to the method easily conducted by a person having an ordinary skill in the art to which the present invention pertains. Here, the dosage form may be a solution in an oily or aqueous medium, a suspension, a syrup, or an emulsion, an extract, a pulvis, a powder, a granule, a tablet, or a capsule, and may further include a dispersant or a stabilizer.

In accordance with another aspect of the present invention, there is provided a pharmaceutical composition for oral administration to alleviate, prevent, or treat obesity, the pharmaceutical composition containing: (a) exenatide or an analog thereof; and (b) chitosan.

The pharmaceutical composition of the present invention allows oral administration.

In the pharmaceutical composition of the present invention, the exenatide analog includes various analogs known in the art. According to an embodiment of the present invention, the exenatide analog is the above-described exenatide analog of the present invention.

According to an embodiment of the present invention, the chitosan may be conjugated to exenatide or an analog thereof or mixed with the pharmaceutical composition Advantageous Effects Features and advantages of the present invention are summarized as follows:

(a) The present invention provides an exenatide analog, a pharmaceutical composition for alleviating diabetes or preventing or treating obesity, and a pharmaceutical composition for suppressing appetite.

(b) The present invention shows almost the same level of anti-diabetic effect as the existing exenatide and liraglutide, which is an antidiabetic agent.

(c) The present invention provides short-length exenatide capable of reducing the production costs of the conventional exenatide.

Mode for Carrying Out the Invention

Figure 1:
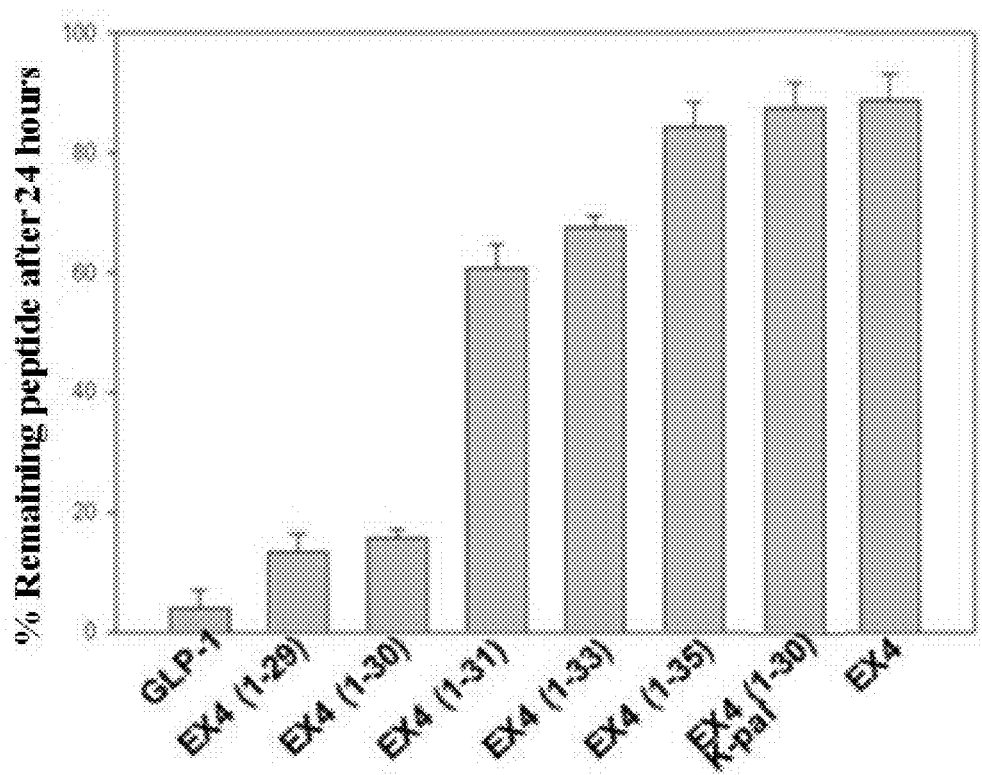
FIG. 1 shows percentages of remaining peptides 24 hours after treatment of short exendin-4 analogs with NEP24.11.

Hereinafter, the present invention will be described in detail with reference to examples. These examples are only for illustrating the present invention more specifically, and it will be apparent to those skilled in the art that the scope of the present invention is not limited by these examples.

EXAMPLES

Terms

As used herein, the term "exenatide" refers to a functional analog of glucagon-like peptide-1 (GLP-1) isolated from salivary glands of *Heloderma suspectum* living in the American Southwest. Exenatide (scientific name: "Exendin-4") is a biological active peptide composed of 39 amino acids, and has 53% amino acid similarity with GLP-1 existing in the human body. In the following examples, Ex4 means exenatide.

As used herein, the term "short exendin-4 analog" refers to exendin-4, of which the sequence of the C-terminal is different. Details are described in example 2.

As used herein, the term "Ex4(1-30)K-fatty acid" refers to an analog in which amino acid residues 1 to 30 are the same as those of the exenatide and K (lysine) having a fatty acid linked to a side chain thereof is conjugated to the C-terminal of the exenatide.

Unless otherwise specified herein, the abbreviations used for the designation of amino acids and the protecting groups used therefore are based on recommendations of the IUPAC-IUB Commission of Biochemical Nomenclature (Biochemistry, 11:1726-1732 (1972)).

The abbreviations of the protecting groups used herein are as follows:

Thr: Threonine
Glu: Glutamic acid
Ser: Serine
Arg: Arginine
Pro: Proline
Leu: Leucine
His: Histidine
Ala: Alanine
Gly: Glycine Phe: Phenylalanine
Asp: Aspartic acid
Lys: Lysine
Gln: Glutamine
Met: Methionine
Ala: Alanine
Val: Valine
Ile: Isoleucine
Trp: Tryptophan
Asn: Asparagine
Boc: t-butyloxycarbonyl
tBu: t-butyl
Fmoc: 9-Fluorenylmethyloxycarbonyl
Trt: Triphenylmethyl
dde: 1-(4,4-Dimethyl-2,6-dioxocyclohexylidene)ethyl Throughout the present specification, the term "%" used to express the concentration of a specific material, unless otherwise particularly stated, refers to (wt/wt) % for solid/solid, (wt/vol) % for solid/liquid, and (vol/vol) % for liquid/liquid.

Example 1: Preparation of Ex4(1-32)K-Cap

Ex4(1-32)K-Cap is composed of the peptide with 33 amino acids in which a lysine-fatty acid is added to Ser located at the 32nd site from the N-terminal of exenatide of chemical formula 1 below:

[Chemical Formula 1] (SEQ ID NO:1)
His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-trp-Leu-Lys-Asn-Gly-Gly-Pro-Ser-Ser-Gly-Ala-Pro-Pro-Pro-Ser For the preparation of Ex4(1-32)K-Cap, Fmoc-Lys (dde) and DMF (dimethylformamide) were loaded on the trityl resin to prepare Fmoc-Ser(tBu)-trityl resin. N,N-Dimethylformamide (DMF) containing 20% piperidine and DMF containing Fmoc-Pro-OH and hydroxy-benzo triazole (HOBt) were added to the Fmoc-Ser(tBu)-trityl resin to prepare Fmoc-Gly-Lys(dde)-trityl resin. Then, DMF containing 20% piperidine was added to the Fmoc-Gly-Lys (dde)-trityl resin, and then the coupling of amino acids was carried out a total of 31 cycles from Fmoc-Gly-OH to Boc-His(Trt)-OH to prepare the peptide of chemical formula 2.

[Chemical formula 2] (SEQ ID NO: 25)
Boc-His(Trt)-Gly-Glu(tBu)-Gly-Thr(tBu)-Phe-Thr(tBu)-Ser(tBu)-Asp(tBu)-Leu-Ser(tBu)-Lys(Boc)-Gln(Trt)-Met-Glu(tBu)-Glu(tBu)-Glu(tBu)-Ala-Val-Arg(pbf)-Leu-Phe-Ile-Glu(tBu)-Trp(Boc)-Leu-Lys(Boc)-Asn(Trt)-Gly-Gly-Pro-Ser-Lys(dde)- trityl resin The peptide of chemical formula 2 was subjected to the addition of DMF containing 2% $NH_2NH_2 \cdot H_2O$ and the removal of dde to prepare the peptide of chemical formula 3.

[Chemical formula 3] (SEQ ID NO: 26)
Boc-His(Trt)-Gly-Glu(tBu)-Gly-Thr(tBu)-Phe-Thr(tBu)-Ser(tBu)-Asp(tBu)-Leu-Ser(tBu)-Lys(Boc)-Gln(Trt)-Met-Glu(tBu)-Glu(tBu)-Glu(tBu)-Ala-Val-Arg(pbf)-Leu-Phe-Ile-Glu(tBu)-Trp(Boc)-Leu-Lys(Boc)-Asn(Trt)-Gly-Gly-Pro-Ser-Lys- trityl resin The peptide of chemical formula 3 was subjected to coupling by addition of DMF containing capric acid, HOBt, and DIC to prepare the peptide of chemical formula 4.

[Chemical formula 4] (SEQ ID NO: 27)
Boc-His(Trt)-Gly-Glu(tBu)-Gly-Thr(tBu)-Phe-Thr(tBu)-Ser(tBu)-Asp(tBu)-Leu-Ser(tBu)-Lys(Boc)-Gln(Trt)-Met-Glu(tBu)-Glu(tBu)-Glu(tBu)-Ala-Val-Arg(pbf)-Leu-Phe-Ile-Glu(tBu)-Trp(Boc)-Leu-Lys(Boc)-Asn(Trt)-Gly-Gly-Pro-Ser- Lys(capric acid)-trityl resin The peptide of chemical formula 4 was subjected to protecting group cleavage and then purification to prepare the peptide of chemical formula 5.

[Chemical formula 5] (SEQ ID NO: 28)
H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Lys(capric acid)-OH(TFA form)

The peptide of chemical formula 5 was subjected to salt exchange (trifluoroacetic acid (TFA) to AcOH) to prepare Ex4(1-32)K-Cap of chemical formula 6.

[Chemical formula 6] (SEQ ID NO:29)
H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Lys(capric acid)-OH (AcOH form)

Example 2: Preparation of Short Exendin-4 Analogs and Analysis of their Effects

Preparation of Short Exendin-4 Analogs and their Stability Test Against NEP24.11

Since the C-terminal of exendin-4 has the nine-AA C-terminal sequence, which is absent in GLP-1, exendin-4 is not easily degraded by neutral endopeptidases, such as NEP24.11 (see Doyle M E et al., Regulatory Peptides Volume 114, Issues 2-3, 15 Jul. 2003, Pages 153-158).

For the stability test against the peptidase NEP24.11, several short-exendin-4 analogs were prepared by varying the sequence of the C-terminal of existing exendin-4 as follows.

(a) Preparation of Ex4(1-29)

For the preparation of Ex4(1-29), Fmoc-Gly-OH, N,N-diisopropylethylamine (DIEA), and dimethylformamide (DMF) were loaded on the trityl resin to prepare Fmoc-Gly-trityl resin. N,N-dimethylformamide (DMF) containing 20% piperidine and DMF containing Fmoc-Asn(Trt)-OH and hydroxy-benzo triazole (HOBt) were added to the Fmoc-Gly-trityl resin to prepare Fmoc-Asn(Trt)-Gly-trityl resin. Then, DMF containing 20% piperidine was added to the Fmoc-Asn(Trt)-Gly-trityl resin, and then the coupling of amino acids was carried out a total of 29 cycles from Fmoc-Lys(Boc)-OH to Boc-His(Trt)-OH to prepare Ex4(1-29).

Boc-His(Trt)-Gly-Glu(tBu)-Gly-Thr(tBu)-Phe-Thr(tBu)-Ser(tBu)-Asp(tBu)-Leu-Ser(tBu)-Lys(Boc)-Gln(Trt)-Met-Glu(tBu)-Glu(tBu)-Glu(tBu)-Ala-Val-Arg(pbf)-Leu-Phe-Ile-Glu(tBu)-Trp(Boc)-Leu-Lys(Boc)-Asn(Trt)-Gly-trityl resin (b) Preparation of Ex4(1-30)

For the preparation of Ex4(1-30), Fmoc-Gly-OH, N,N-diisopropylethylamine (DIEA), and dimethylformamide (DMF) were loaded on the trityl resin to prepare Fmoc-Gly-trityl resin. N,N-dimethylformamide (DMF) containing 20% piperidine and DMF containing Fmoc-Gly-OH and hydroxy-benzo triazole (HOBt) were added to the Fmoc-Gly-trityl resin to prepare Fmoc-Gly-Gly-trityl resin. Then, DMF containing 20% piperidine was added to the Fmoc-Gly-Gly-trityl resin, and then the coupling of amino acids was carried out a total of 30 cycles from Fmoc-Asn(Trt)-OH to Boc-His(Trt)-OH to prepare Ex4(1-30).

Boc-His(Trt)-Gly-Glu(tBu)-Gly-Thr(tBu)-Phe-Thr(tBu)-Ser(tBu)-Asp(tBu)-Leu-Ser(tBu)-Lys(Boc)-Gln(Trt)-Met-

Glu(tBu)-Glu(tBu)-Glu(tBu)-Ala-Val-Arg(pbf)-Leu-Phe-Ile-Glu(tBu)-Trp(Boc)-Leu-Lys(Boc)-Asn(Trt)-Gly-Gly-trityl resin (c) Preparation of Ex4(1-31)

For the preparation of Ex4(1-31), Fmoc-Pro-OH, N,N-diisopropylethylamine (DIEA), and dimethylformamide (DMF) were loaded on the trityl resin to prepare Fmoc-Pro-trityl resin. N,N-dimethylformamide (DMF) containing 20% piperidine and DMF containing Fmoc-Gly-OH and hydroxy-benzo triazole (HOBt) were added to the Fmoc-Pro-trityl resin to prepare Fmoc-Gly-Pro-trityl resin. Then, DMF containing 20% piperidine was added to the Fmoc-Gly-Pro-trityl resin, and then the coupling of amino acids was carried out a total of 31 cycles from Fmoc-Gly-OH to Boc-His(Trt)-OH to prepare Ex4(1-31).

Boc-His(Trt)-Gly-Glu(tBu)-Gly-Thr(tBu)-Phe-Thr(tBu)-Ser(tBu)-Asp(tBu)-Leu-Ser(tBu)-Lys(Boc)-Gln(Trt)-Met-Glu(tBu)-Glu(tBu)-Glu(tBu)-Ala-Val-Arg(pbf)-Leu-Phe-Ile-Glu(tBu)-Trp(Boc)-Leu-Lys(Boc)-Asn(Trt)-Gly-Gly-Pro-trityl resin (d) Preparation of Ex4(1-32)

For the preparation of Ex4(1-32), Fmoc-Ser(tBu)-OH, N,N-diisopropylethylamine (DIEA), and dimethylformamide (DMF) were loaded on the trityl resin to prepare Fmoc-Ser(tBu)-trityl resin. N,N-Dimethylformamide (DMF) containing 20% piperidine and DMF containing Fmoc-Pro-OH and hydroxy-benzo triazole (HOBt) were added to the Fmoc-Ser(tBu)-trityl resin to prepare Fmoc-Pro-Ser(tBu)-trityl resin. Then, DMF containing 20% piperidine was added to the Fmoc-Pro-Ser(tBu)-trityl resin, and then the coupling of amino acids was carried out a total of 32 cycles from Fmoc-Gly-OH to Boc-His(Trt)-OH to prepare Ex4(1-32).

Boc-His(Trt)-Gly-Glu(tBu)-Gly-Thr(tBu)-Phe-Thr(tBu)-Ser(tBu)-Asp(tBu)-Leu-Ser(tBu)-Lys(Boc)-Gln(Trt)-Met-Glu(tBu)-Glu(tBu)-Glu(tBu)-Ala-Val-Arg(pbf)-Leu-Phe-Ile-Glu(tBu)-Trp(Boc)-Leu-Lys(Boc)-Asn(Trt)-Gly-Gly-Pro-Ser(tBu)- trityl resin (e) Preparation of Ex4(1-33)

For the preparation of Ex4(1-33), Fmoc-Ser(tBu)-OH, N,N-diisopropylethylamine (DIEA), and dimethylformamide (DMF) were loaded on the trityl resin to prepare Fmoc-Ser(tBu)-trityl resin. N,N-Dimethylformamide (DMF) containing 20% piperidine and DMF containing Fmoc-Ser(tBu)-OH and hydroxy-benzo triazole (HOBt) were added to the Fmoc-Ser(tBu)-trityl resin to prepare Fmoc-Ser(tBu)-Ser(tBu)-trityl resin. Then, DMF containing 20% piperidine was added to the Fmoc-Ser(tBu)-Ser(tBu)-trityl resin, and then the coupling of amino acids was carried out a total of 33 cycles from Fmoc-Pro-OH to Boc-His(Trt)-OH to prepare Ex4(1-33).

Boc-His(Trt)-Gly-Glu(tBu)-Gly-Thr(tBu)-Phe-Thr(tBu)-Ser(tBu)-Asp(tBu)-Leu-Ser(tBu)-Lys(Boc)-Gln(Trt)-Met-Glu(tBu)-Glu(tBu)-Glu(tBu)-Ala-Val-Arg(pbf)-Leu-Phe-Ile-Glu(tBu)-Trp(Boc)-Leu-Lys(Boc)-Asn(Trt)-Gly-Gly-Pro-Ser(tBu)- Ser(tBu)-trityl resin Stability test against NEP24.11 of exendin-4 peptides having different sequences in the C-terminal of exendin-4 was carried out. The prepared peptides were allowed to react with recombinant human NEP24.11 at 37° C. for 0, 4, 12, 24, 48, and 96 hours, and the concentrations of the peptides were analyzed through HPLC. As a result, it was verified that analogs Ex4(1-35), Ex4(1-33), Ex4(1-32), and Ex4(1-31) showed a long half-life against NEP24.11, but analogs Ex4(1-29) and Ex4(1-30) showed a short half-life. Therefore, it can be seen that the amino acid sequence after the 31st amino acid residue of exendin-4 plays a key role on the resistance to NEP24.11 (Table 1 and FIG. 1).

TABLE 1

| Peptide | Sequence | $T^{1/2}$ (h) |
| --- | --- | --- |
| Ex4 SEQ ID NO: 1 | HGEGTFTSDL SKQMEEEAVR LFIEWLKNGG PSSGAPPPS | >96 |
| GLP-1 SEQ ID NO: 2 | HAEGTFTSDV SSYLEGQAAK EFIAWLVKGR | 5.5 |
| Ex4 (1-29) SEQ ID NO: 3 | HGEGTFTSDL SKQMEEEAVR LFIEWLKNG | 9.1 |
| Ex4 (1-30) SEQ ID NO: 4 | HGEGTFTSDL SKQMEEEAVR LFIEWLKNGG | 9.3 |
| Ex4 (1-31) SEQ ID NO: 5 | HGEGTFTSDL SKQMEEEAVR LFIEWLKNGG P | 32.4 |
| Ex4 (1-32) SEQ ID NO: 6 | HGEGTFTSDL SKQMEEEAVR LFIEWLKNGG PS | 65.2 |
| Ex4 (1-33) SEQ ID NO: 7 | HGEGTFTSDL SKQMEEEAVR LFIEWLKNGG PSS | 57.0 |
| Ex4 (1-35) SEQ ID NO: 8 | HGEGTFTSDL SKQMEEEAVR LFIEWLKNGG PSSGA | >96 |

Activity and CD Spectrum of Short Exendin-4 Analogs on GLP-1 Receptor

For comparative analysis of the relationship between activity of the short exendin-4 analog on the GLP-1 receptor and the Ex-4 structure, luciferase analysis and CD spectrum test were carried out.

The luciferase assay system used in the present study can investigate the activity of a drug (ligand), which binds to a cell receptor, in cells. Fibroblast strain cv-1 ($1 \times 10^6$ cells/ml) was cultured in a 96-well cell culture plate for 24 hours. After that, the 96-well cell culture plate with 50 multiplicity of infection (MOI) of viruses and 25 MOI of viruses was treated with the GLP-1 receptor inserted into adenovirus and cAMP response element (CRE) luciferase, respectively, followed by culture for 3 hours, and then the medium is exchanged with FBS-free medium, followed by culture for 16 hours. After the culture, the cells were treated with each short exendin-4 analog, followed by culture for 6 hours, and then the level of luciferase, as a reporter gene, expressed by the activated GLP-1 receptor was quantified using a luminometer.

Figure 2A:
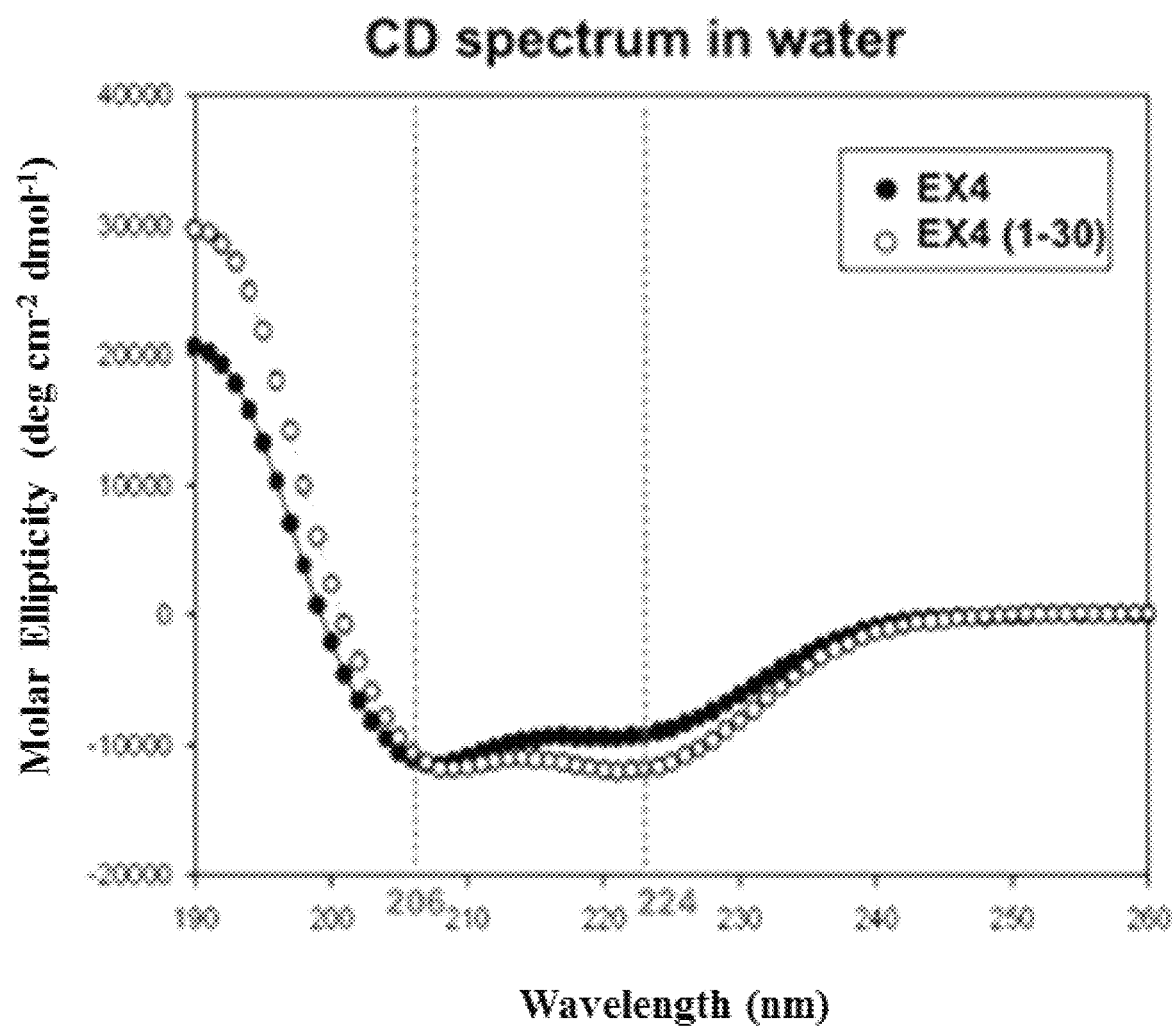
FIGS. 2a and 2b show CD spectra illustrating comparative analysis of the relationship between the activity on the GLP-1 receptor and the Ex-4 structure.
Figure 2B:
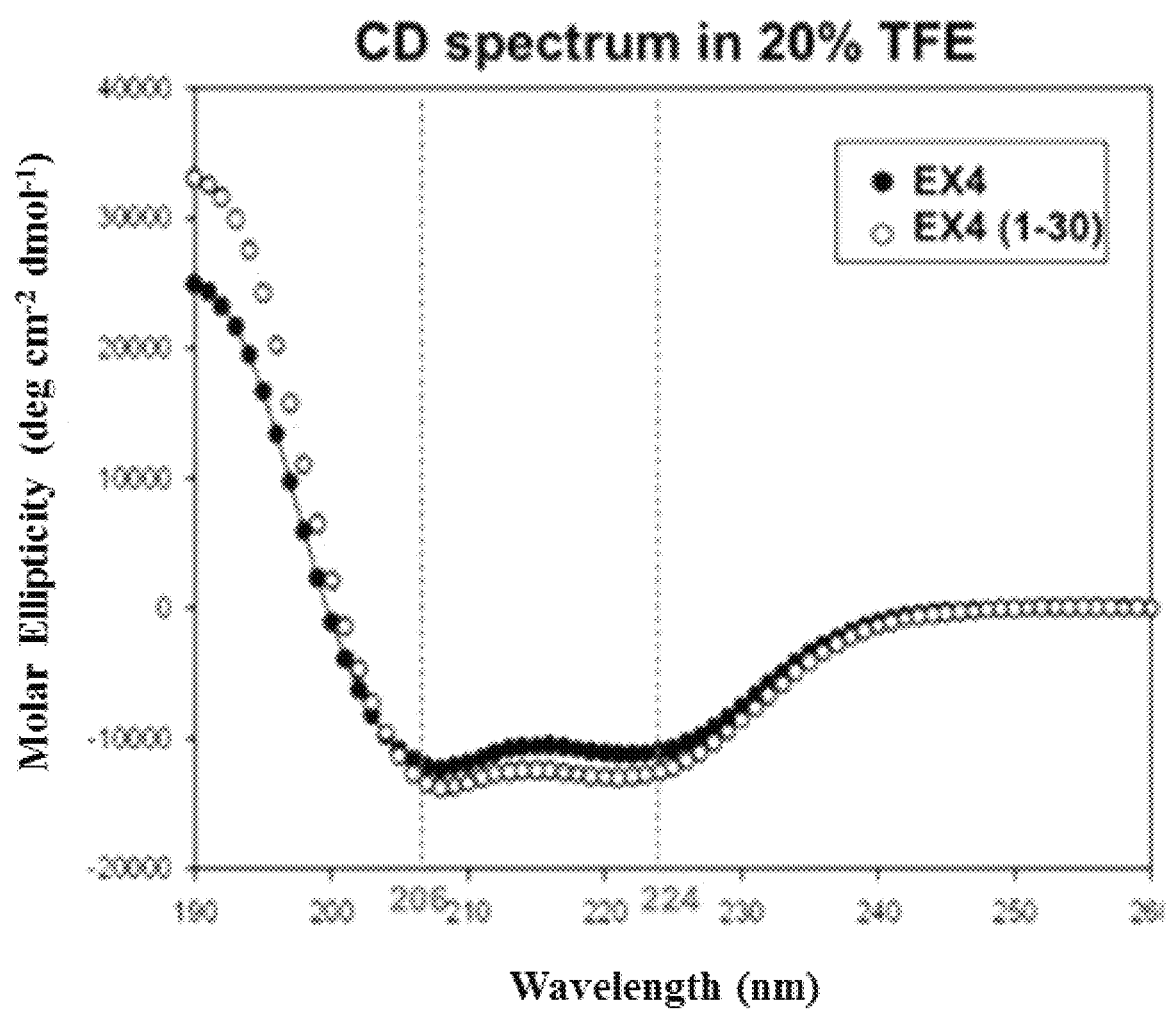
Figure 3A:
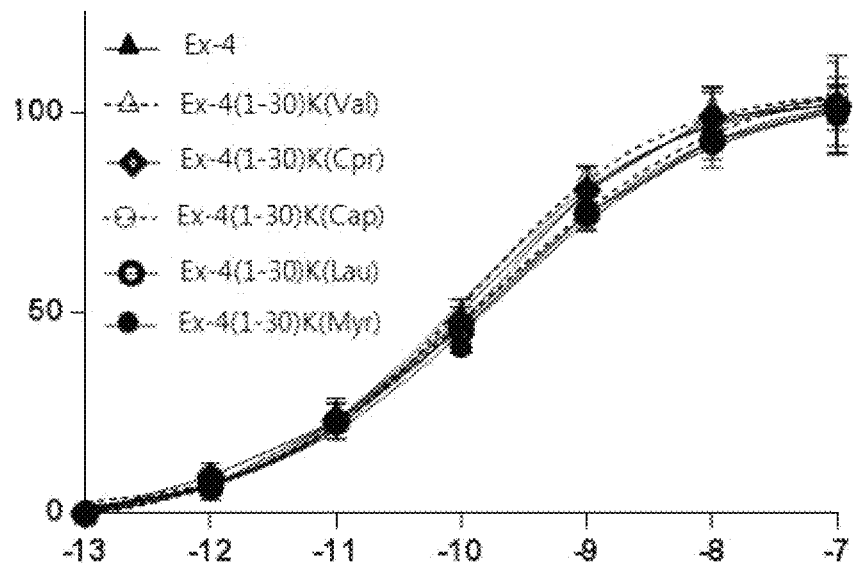
FIGS. 3a to 3c show percentages of remaining peptides 24 hours after treatment of Ex-4(1-30)-fatty acid conjugates with NEP24.11.
Figure 3B:
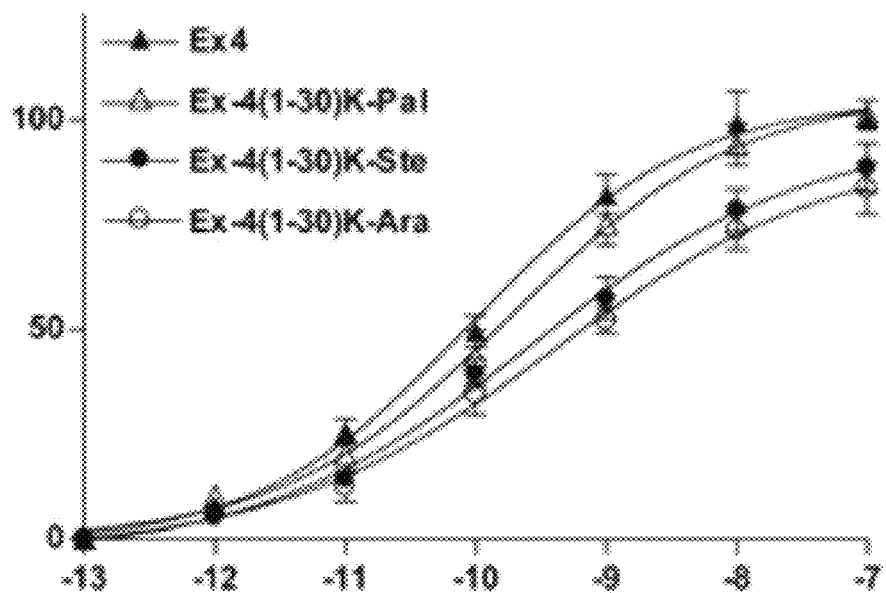
Figure 3C:
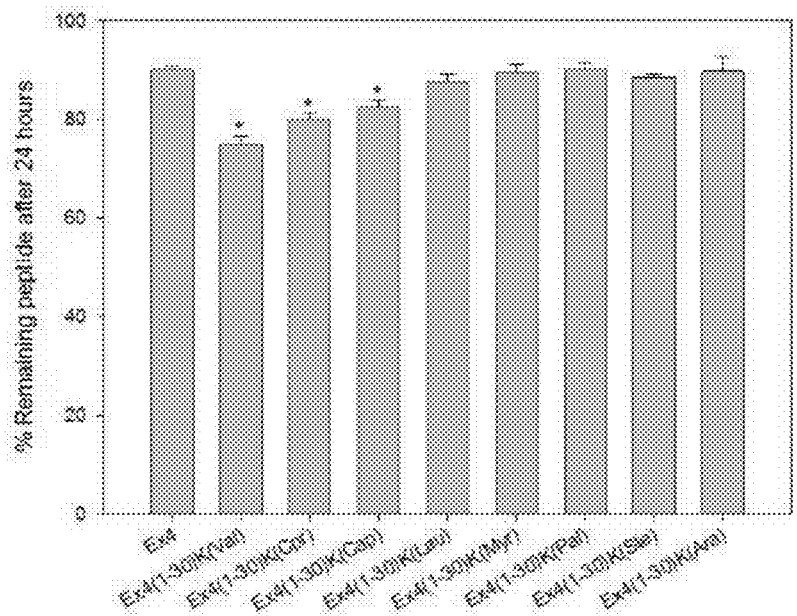
Figure 4:
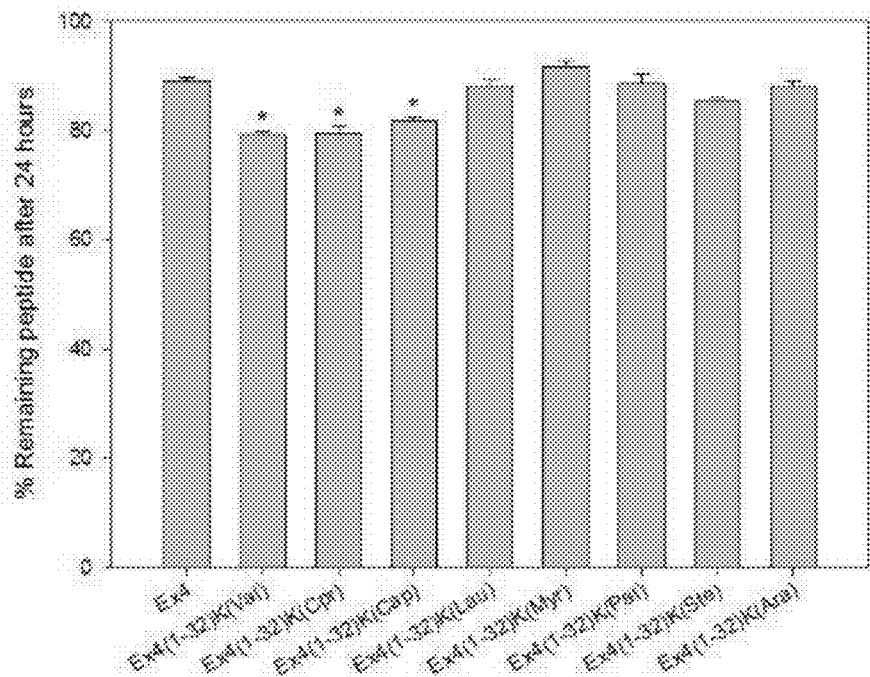
FIG. 4 shows percentage of remaining peptides 24 hours after treatment of Ex-4(1-32)-fatty acid conjugates with NEP24.11.

As a result, it was verified that the activity of analogs Ex4(1-30), Ex4(1-31), Ex4(1-32), Ex4(1-33), and Ex4(1-35) on the GLP-1 receptor showed similar patterns compared with Ex4 as a positive control. However, it was verified that Ex4(1-29) was 10-fold higher than exendin-4 with respect to the activity on the GLP-1 receptor (Table 2 and FIGS. 2a and 2b).

TABLE 2

| Peptide | Sequence | Ec50 (nM) |
|---|---|---|
| Ex4 SEQ ID NO: 1 | HGEGTFTSDL SKQMEEEAVR LFIEWLKNGG PSSGAPPPS | 0.103 |
| Ex4 (1-35) SEQ ID NO: 8 | HGEGTFTSDL SKQMEEEAVR LFIEWLKNGG PSSGA | 0.124 |
| Ex4 (1-33) SEQ ID ID: 7 | HGEGTFTSDL SKQMEEEAVR LFIEWLKNGG PSS | 0.238 |
| Ex4 (1-32) SEQ ID NO: 6 | HGEGTFTSDL SKQMEEEAVR LFIEWLKNGG PSS | 0.215 |
| Ex4 (1-31) SEQ ID NO: 5 | HGEGTFTSDL SKQMEEEAVR LFIEWLKNGG P | 0.355 |
| Ex4 (1-30) SEQ ID NO: 4 | HGEGTFTSDL SKQMEEEAVR LFIEWLKNGG | 0.265 |
| Ex4 (1-29) SEQ ID NO: 3 | HGEGTFTSDL SKQMEEEAVR LFIEWLKNG | 1.16 |

Example 2: Preparation of Short Exendin-4-Fatty Acid Conjugates and Analysis of their Effects Preparation of Short Exendin-4-Fatty Acid Conjugates and Comparative Test of their Activity and Stability For the improvement of stability of short exendin-4, short exendin-4 conjugates were prepared by conjugating several fatty acids to the C-terminal of exendin-4, and then their stability against NEP24.11 and their activity on GLP-1 receptor were compared. Test methods are the same as in example 1 above. As a result, it was verified that analogs Ex4(1-30)K-Cap and Ex4(1-30)K-Pal had excellent activity on GLP-1 receptor (Tables 3 and 4 and FIGS. 3a-3c and 4).

TABLE 3

| Peptide | Sequence | EC50 (nM) | $T^{1}/_{2}$ (h) |
|---|---|---|---|
| Ex4 SEQ ID NO: 1 | HGEGTFTSDL SKQMEEEAVR LFIEWLKNGG PSSGAPPPS | 0.103 | >96 |
| Ex4(1-30)K(Val) SEQ ID NO: 9 | HGEGTFTSDL SKQMEEEAVR LFIEWLKNGG K-Valeric acid (C6) | 0.132 | 52.5 |

TABLE 3-continued

| Peptide | Sequence | EC50 (nM) | $T^{1/2}$ (h) |
|---|---|---|---|
| Ex(1-30)K(Cpr) SEQ ID NO: 10 | HGEGTFTSDL SKQMEEEAVR LFIEWLKNGG K-Caprylic acid (C8) | 0.206 | 60.8 |
| Ex4(1-30)K(Cap) SEQ ID NO: 11 | HGEGTFTSDL SKQMEEEAVR LFIEWLKNGG K-Capric acid (C10) | 0.218 | >96 |
| Ex(1-30)K(Lau) SEQ ID NO: 12 | HGEGTFTSDL SKQMEEEAVR LFIEWLKNGG K-Lauric acid (C12) | 0.403 | >96 |
| Ex4(1-30)K(Myr) SEQ ID NO: 13 | HGEGTFTSD SKQMEEEAVR LFIEWLKNGG K-Myristic acid (C14) | 0.453 | >96 |
| Ex4(1-30)K(Pal) SEQ ID NO: 14 | HGEGTFTSD SKQMEEEAVR LFIEWLKNGG K-Palmitic acid (C16) | 0.412 | >96 |
| Ex4(1-30)K(Ste) SEQ ID NO: 15 | HGEGTFTSDL SKQMEEEAVR LFIEWLKNGG K-Stearic acid (C18) | 0.892 | >96 |
| Ex4(1-30)K(Ara) SEQ ID NO: 16 | HGEGTFTSDL SKQMEEEAVR LFIEWLKNGG K-Arachidic acid (C20) | 0.923 | >96 |

TABLE 4

| Peptide | Sequence | EC50 (nM) | $T^{1/2}$ (h) |
|---|---|---|---|
| Ex4 SEQ ID NO: 1 | HGEGTFTSDL SKQMEEEAVR LFIEWLKNGG PSSGAPPPS | 0.112 | >95 |
| Ex4(1-32)K(Val) SEQ ID NO: 17 | HGEGTFTSDL SKQMEEEAVR LFIEWLKNGG PS K-Valeric acid (C6) | 0.129 | 51.6 |
| Ex4(1-32)K(Cpr) SEQ ID NO: 18 | HGEGTFTSDL SKQMEEEAVR LFIEWLKNGG PS K-Caprylic acid (C8) | 0.189 | 70.9 |
| Ex4(1-32)K(Cap) SEQ ID NO: 19 | HGEGTFTSDL SKQMEEEAVR LFIEWLKNGG PS K-Capric acid (C10) | 0.207 | >96 |
| Ex4(1-32)K(Lau) SEQ ID NO: 20 | HGEGTFTSDL SKQMEEEAVR LFIEWLKNGG PS K-Lauric acid (C12) | 0.443 | >96 |
| Ex4(1-32)K(Myr) SEQ ID NO: 21 | HGEGTFTSDL SKQMEEEAVR LFIEWLKNGG PS K-Myristic acid (C14) | 0.432 | >96 |
| Ex4(1-32)K(Pal) SEQ ID NO: 22 | HGEGTFTSDL SKQMEEEAVR LFIEWLKNGG PS K-Palmitic acid (C16) | 0.406 | >96 |
| Ex4(1-32)K(Ste) SEQ ID NO: 23 | HGEGTFTSDL SKQMEEEAVR LFIEWLKNGG PS K-Stearic acid (C18) | 0.789 | >96 |
| Ex4(1-32)K(Ara) SEQ ID NO: 24 | HGEGTFTSDL SKQMEEEAVR LFIEWLKNGG PS K-Arachidic acid (C20) | 0.911 | >96 |

Figure 5:
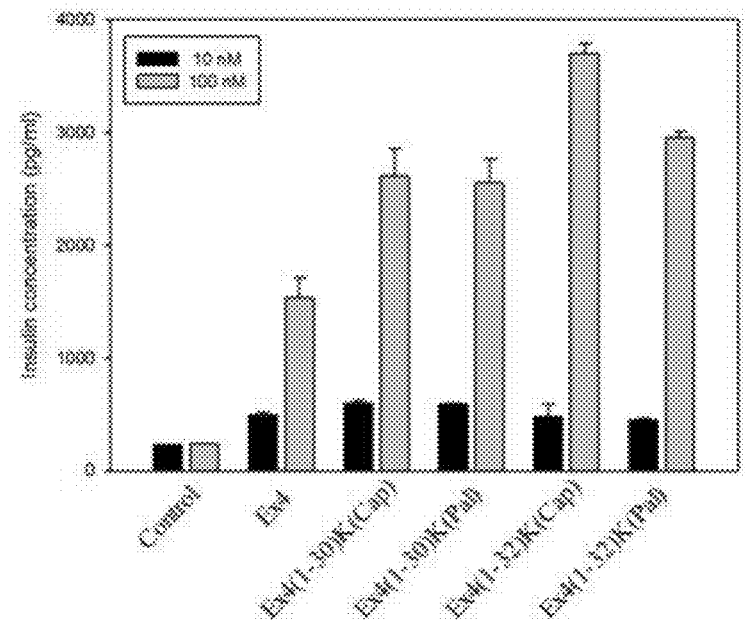
FIG. 5 shows insulin secretion degrees of short exendin-4-fatty acid conjugates.

Evaluation of Insulin Secretion of Short Exendin-4-Fatty Acid Conjugates on Pancreas β Cells The degrees of insulin secretion of the prepared analogs for INS-1 pancreatic β-cells extracted from rats were investigated. The cells were treated with 10 nM and 100 nM of exendin-4 and its analogs in 11.1 mM glucose-containing KRH buffer, and then the concentration of insulin secreted after 12 hours was quantified using ELISA. As a result, it was verified that all the short exendin-4-fatty acid conjugates showed increased degrees of insulin secretion compared with exendin-4, and specifically, Ex4(1-32)K(Cap) showed the highest degree of insulin secretion (FIG. 5).

Evaluation of Lipolysis Degrees of Short Exendin-4-Fatty Acid Conjugates on Adipocytes After preadiocytes 3T3-L1 were differentiated into adipocytes, the lipolysis degrees of short exendin-4-fatty acid conjugates were measured. 3T3-L1 ($3 \times 10^4$ cells/ml) were cultured on a 24-well cell culture plate for 24 hours, and then the medium was exchanged with a medium containing 10% fetal bovine serum (FBS), 3-Isobutyl-1-methylxanthine (IBMX), and dexamethasone, followed by culture for 48 hours. After that, the medium was exchanged with a medium containing 10% FBS and insulin, and the cells were cultured until 14 days while the medium was exchanged with a medium with the same composition for every 2-3 days, thereby inducing the differentiation into adipocytes. After the differentiated adipocytes were treated with short exendin-4-fatty acid conjugates, the amount of hydrogen peroxide ($H_2O_2$) induced from glycerol discharged out of cells was quantified.

Figure 6:
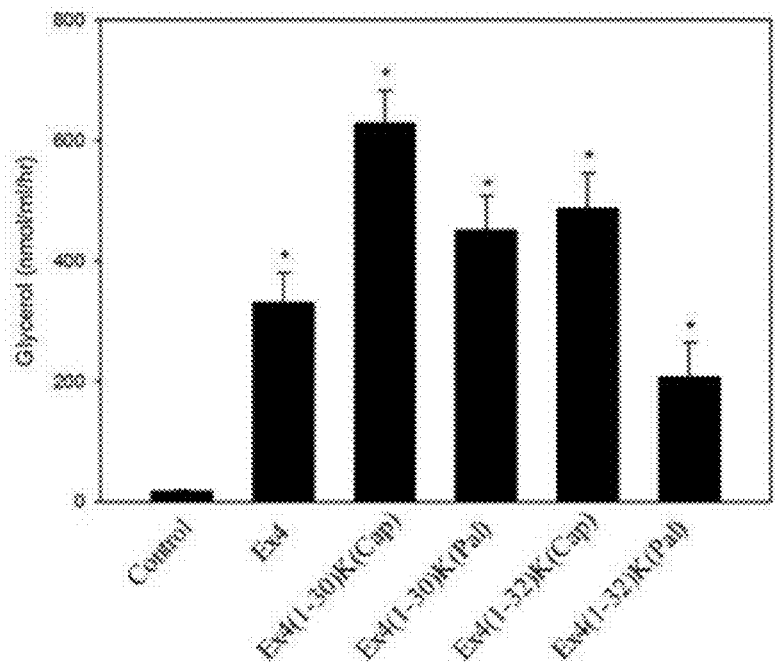
FIG. 6 shows lipolysis degrees of short exendin-4-fatty acid conjugates on adipocytes.

As a result, it was verified that all the analogs promoted the lipolysis of adipocytes compared with exendin-4 (FIG. 6).

Figure 7A:
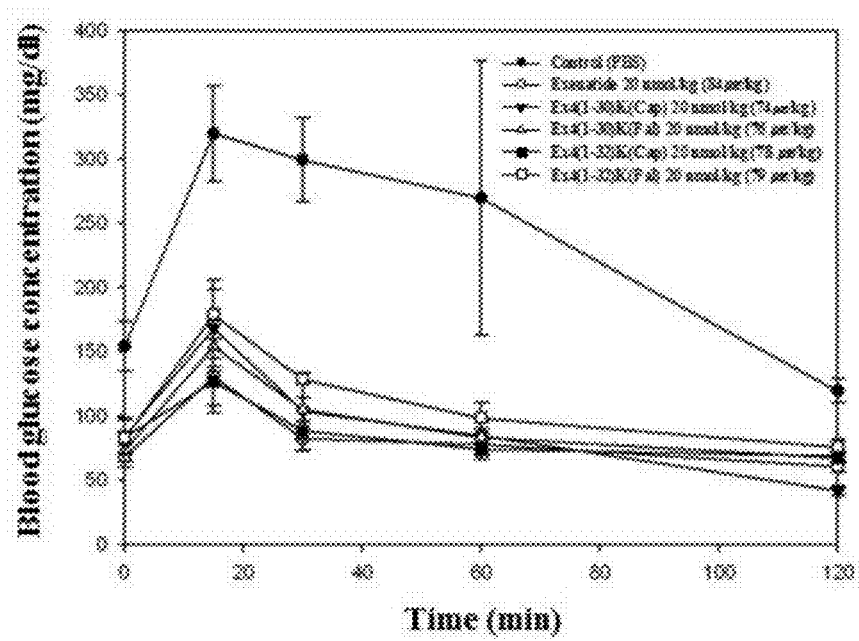
FIGS. 7a and 7b show results confirming in vivo glucose tolerance effects of four kinds of short exendin-4-fatty acid conjugates.
Figure 7B:
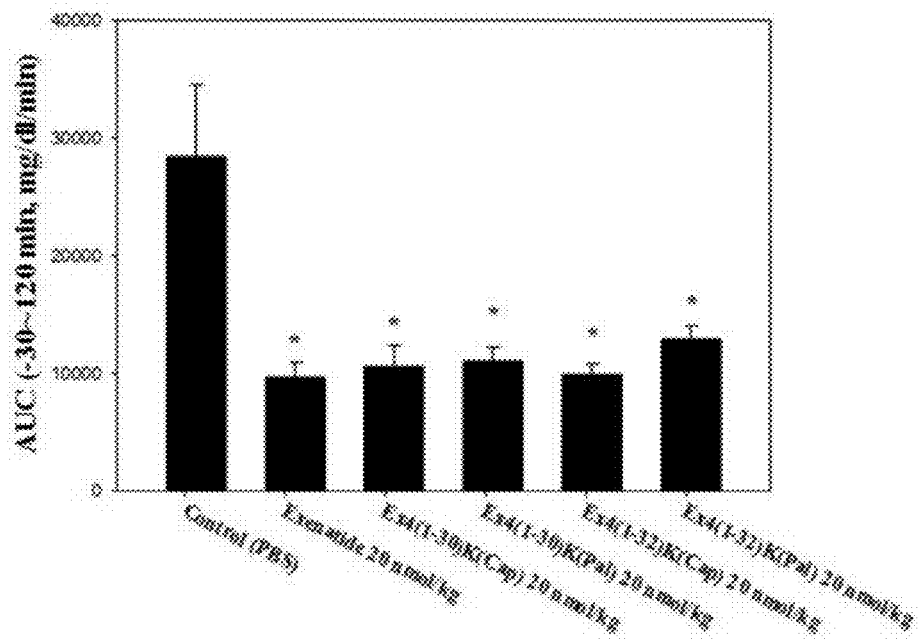

Glucose Tolerance Test of Short Exendin-4-Fatty Acid Conjugates Using Diabetes Model Mice After male db/db mice (6-12 week aged) were fasted for 18 hours, the mice were subcutaneously administered with four kinds of short exendin-4-fatty acid conjugates, Ex4(1-30)K-Pal, Ex4(1-30)K-Cap, Ex4(1-32)K-Pal, and Ex4(1-32)K-Cap at a concentration of 20 nmol/kg for each, and after 30 minutes, abdominally administered with glucose (1.5 g/kg). After 0, 15, 30, 60, and 120 minutes, the blood was collected from the end of the tail of the mice, and then the blood glucose was measured using a blood glucose monitor (Accu-check, Roche, Germany), thereby checking the glucose tolerance ability. As a result, it was verified that all the four kinds of conjugates had a significant glucose tolerance similar to that of exenatide as a positive control (FIGS. 7a and 7b).

Figure 8A:
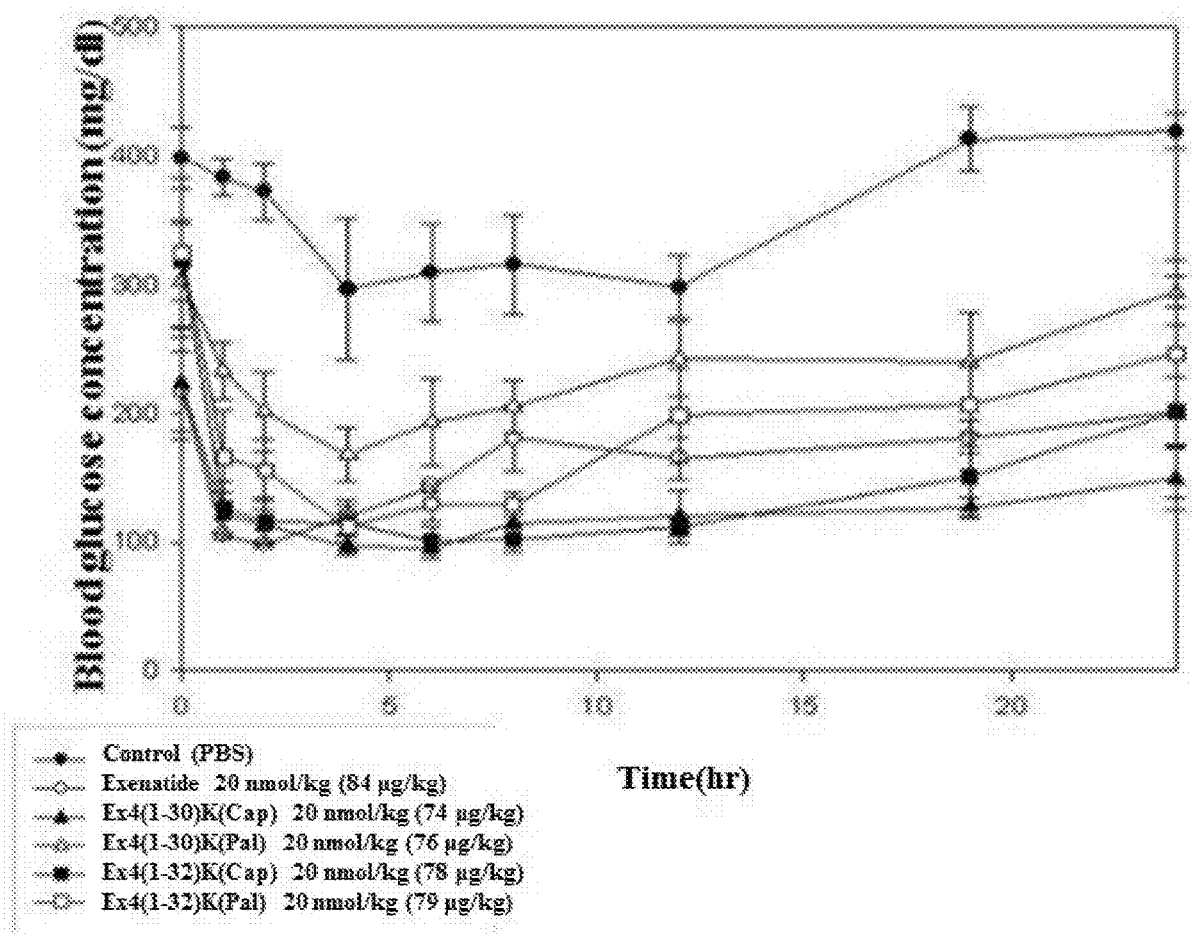
FIGS. 8a and 8b show results confirming in vivo 24-hour antidiabetic effects of four kinds of short exendin-4-fatty acid conjugates.
Figure 8B:
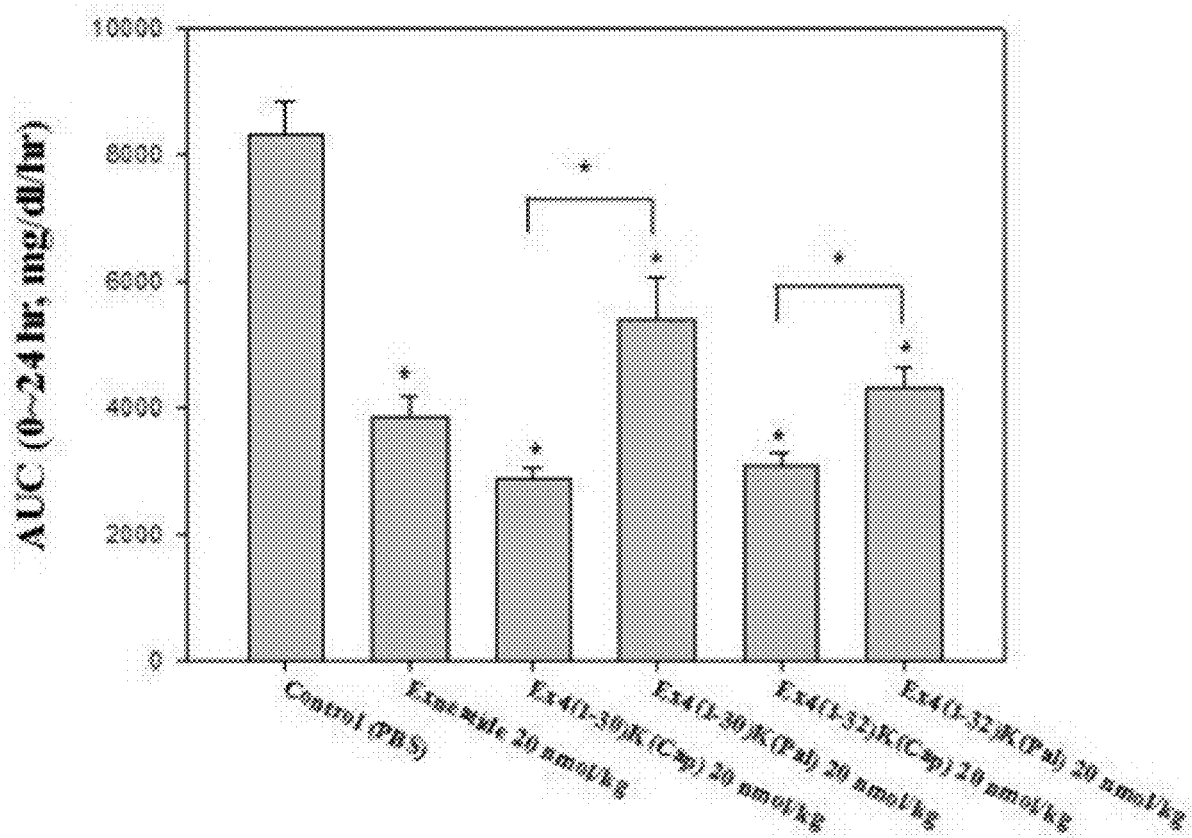

Antidiabetic Effect Test of Short-Exendin-4-Fatty Acid Conjugates Using Diabetic Model Mice After male db/db mice (6-12 week aged) were subcutaneously administered with four kinds of short exendin-4-fatty acid conjugates, Ex4(1-30)K-Pal, Ex4(1-30)K-Cap, Ex4(1-32)K-Pal, and Ex4(1-32)K-Cap at a concentration of 20 nmol/kg for each, and then, at hour 0, 1, 2, 4, 6, 8, 12, 19, and 24, the blood was collected from the end of the tail of the mice to measure the blood glucose using a blood glucose monitor. As a result, it was verified that all the four kinds of conjugates showed a significant blood glucose lowering effect similar to that of exenatide as a positive control, and especially, Ex4(1-30)K-Cap and Ex4(1-32)K-Cap showed a more excellent blood glucose lowering effect than Ex4(1-30)K-Pal and Ex4(1-32)K-Pal (FIGS. 8a and 8b).

Figure 9A:
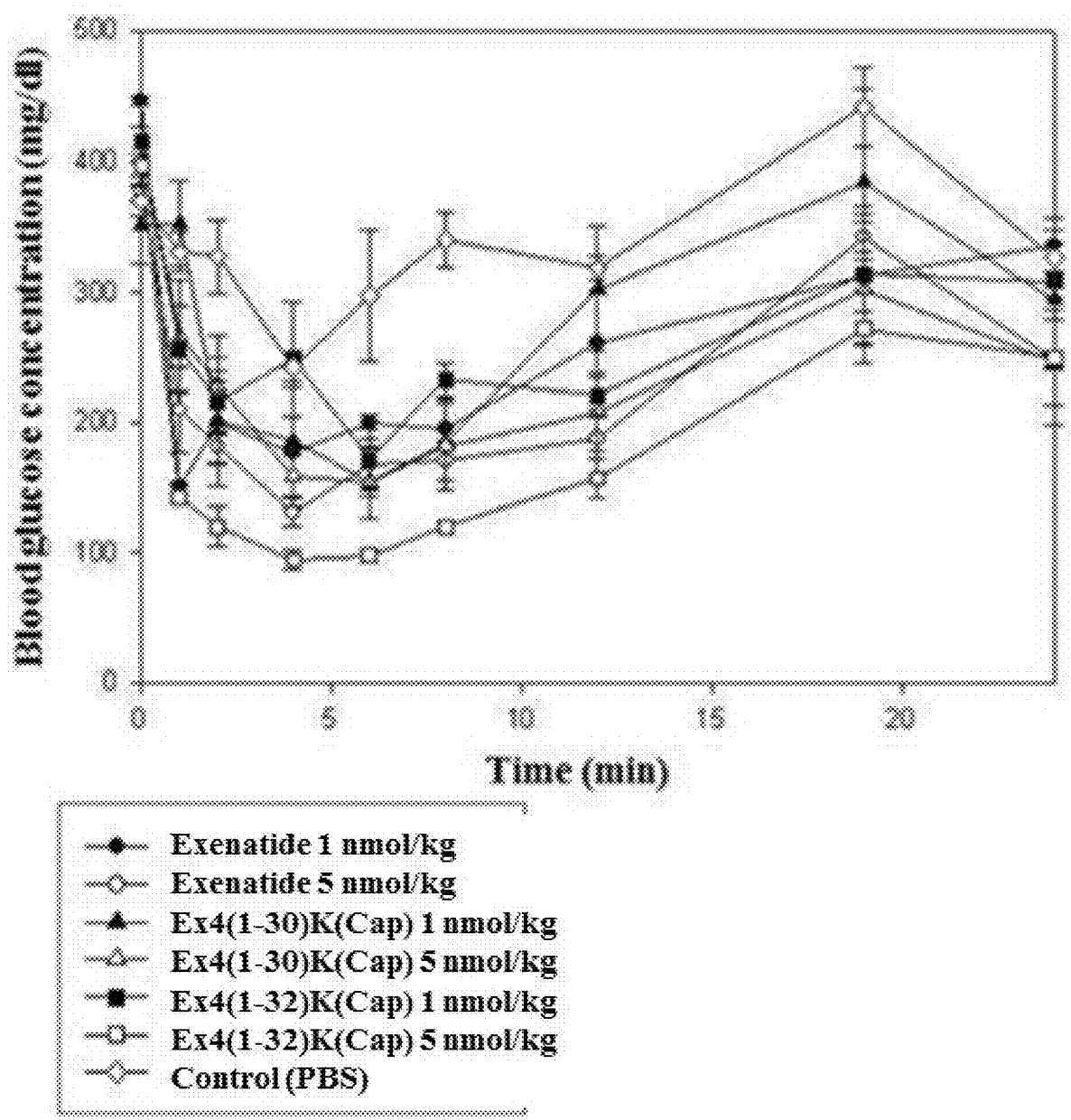
FIGS. 9a and 9b show results confirming in vivo 24-hour concentration-dependent antidiabetic effects of four kinds of short exendin-4-fatty acid conjugates.
Figure 9B:
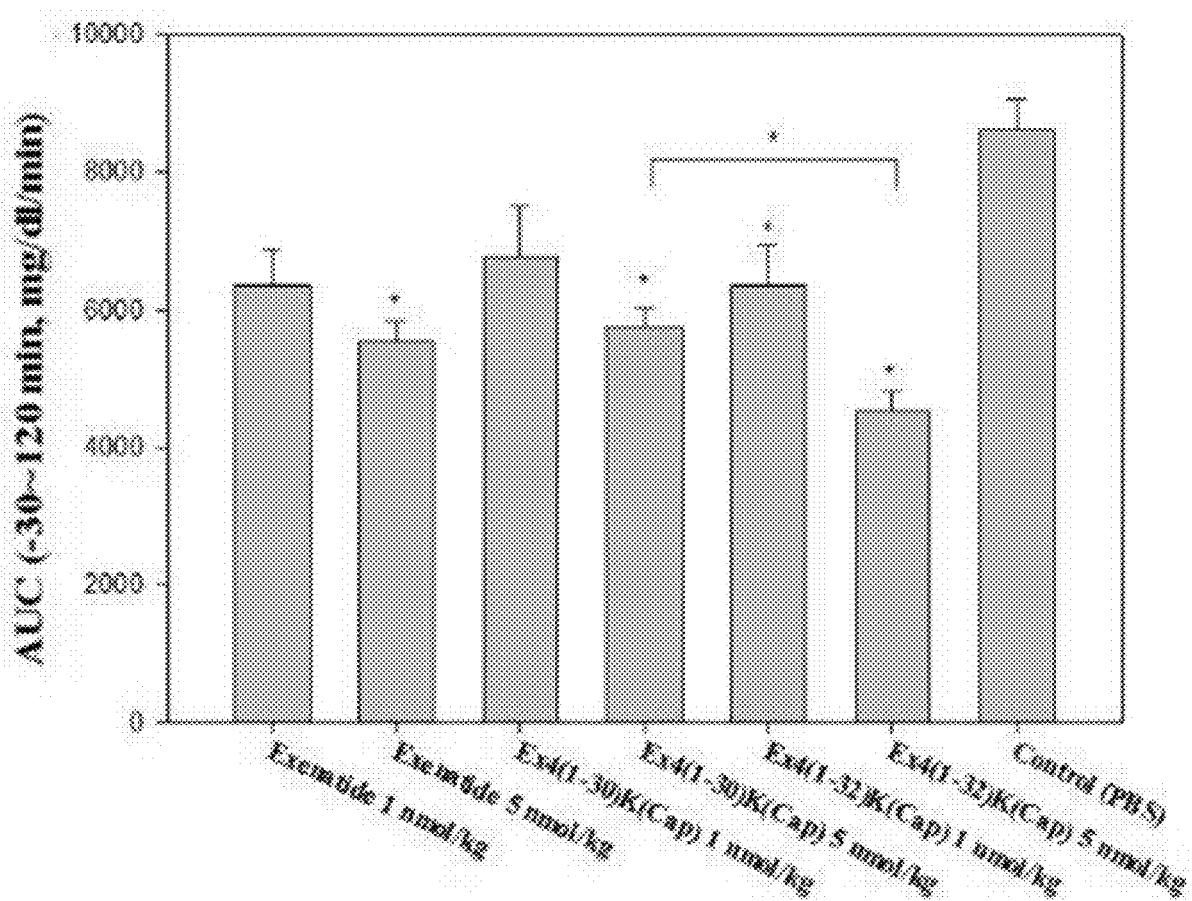
Figure 10A:
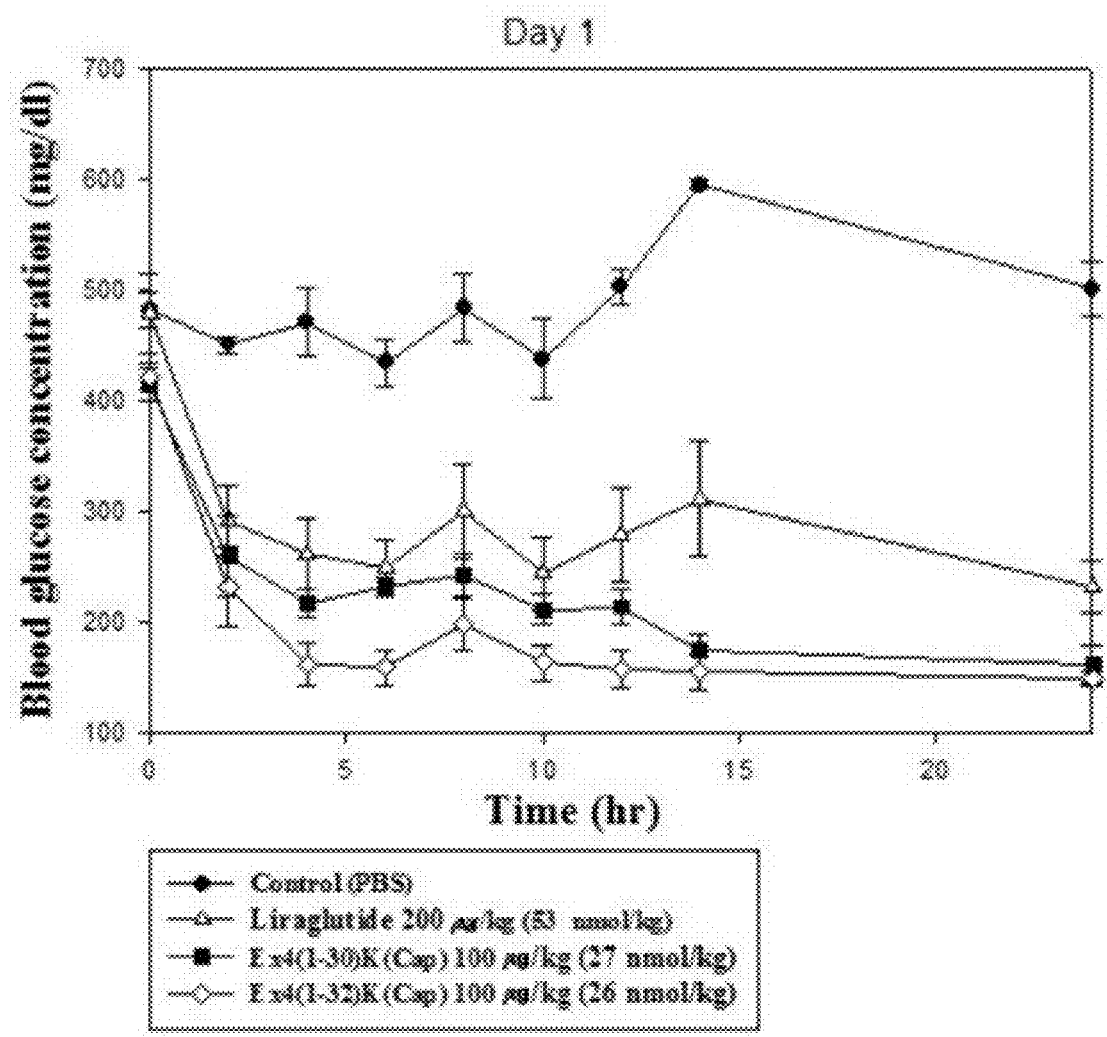
FIGS. 10a and 10b show blood glucose measurement results on day 1 in the effect comparison test of liraglutide and short exendin-4-fatty acid conjugates.
Figure 10B:
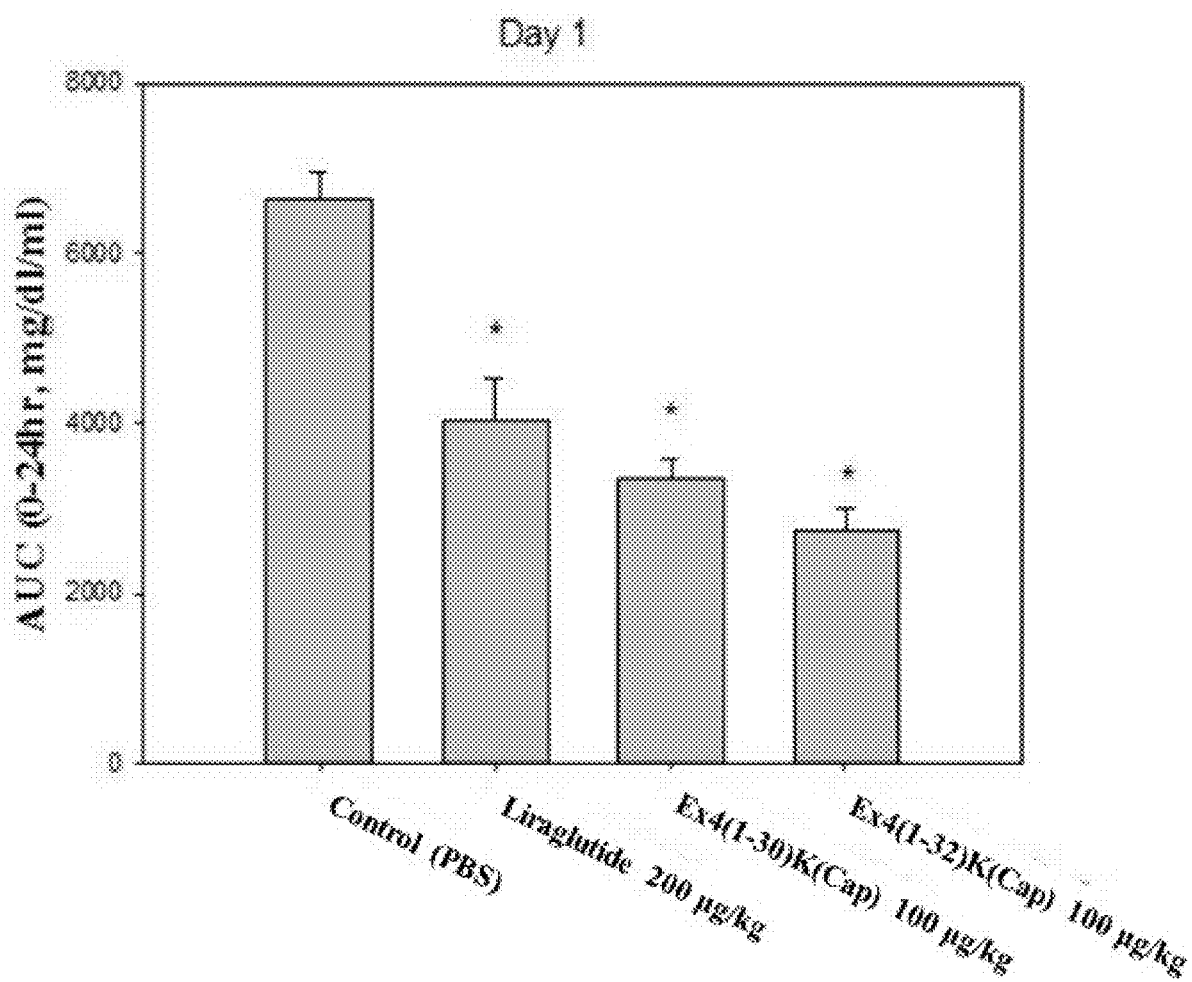
Figure 11A:
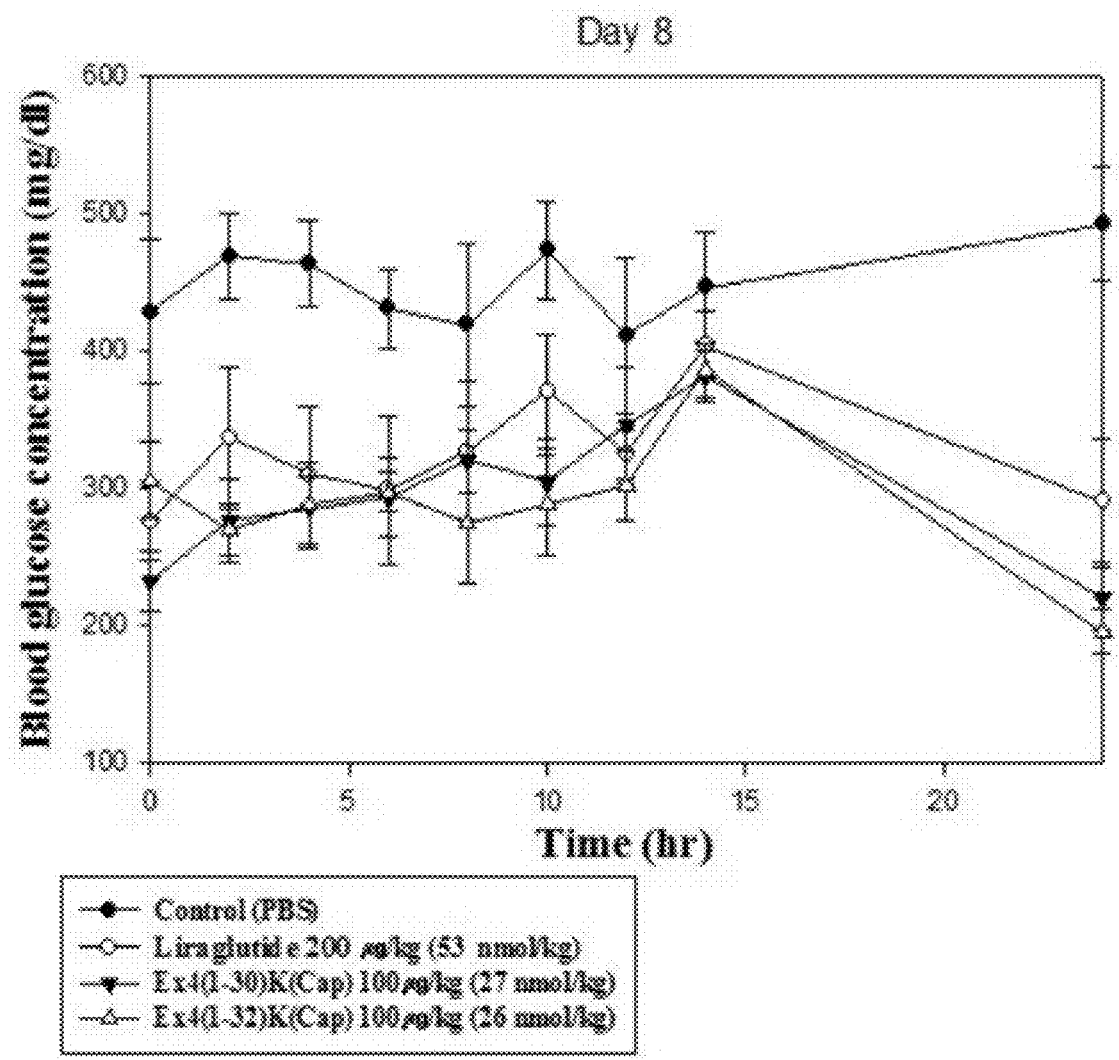
FIGS. 11a and 11b show blood glucose measurement results on day 8 in the effect comparison test of liraglutide and short exendin-4-fatty acid conjugates.
Figure 11B:
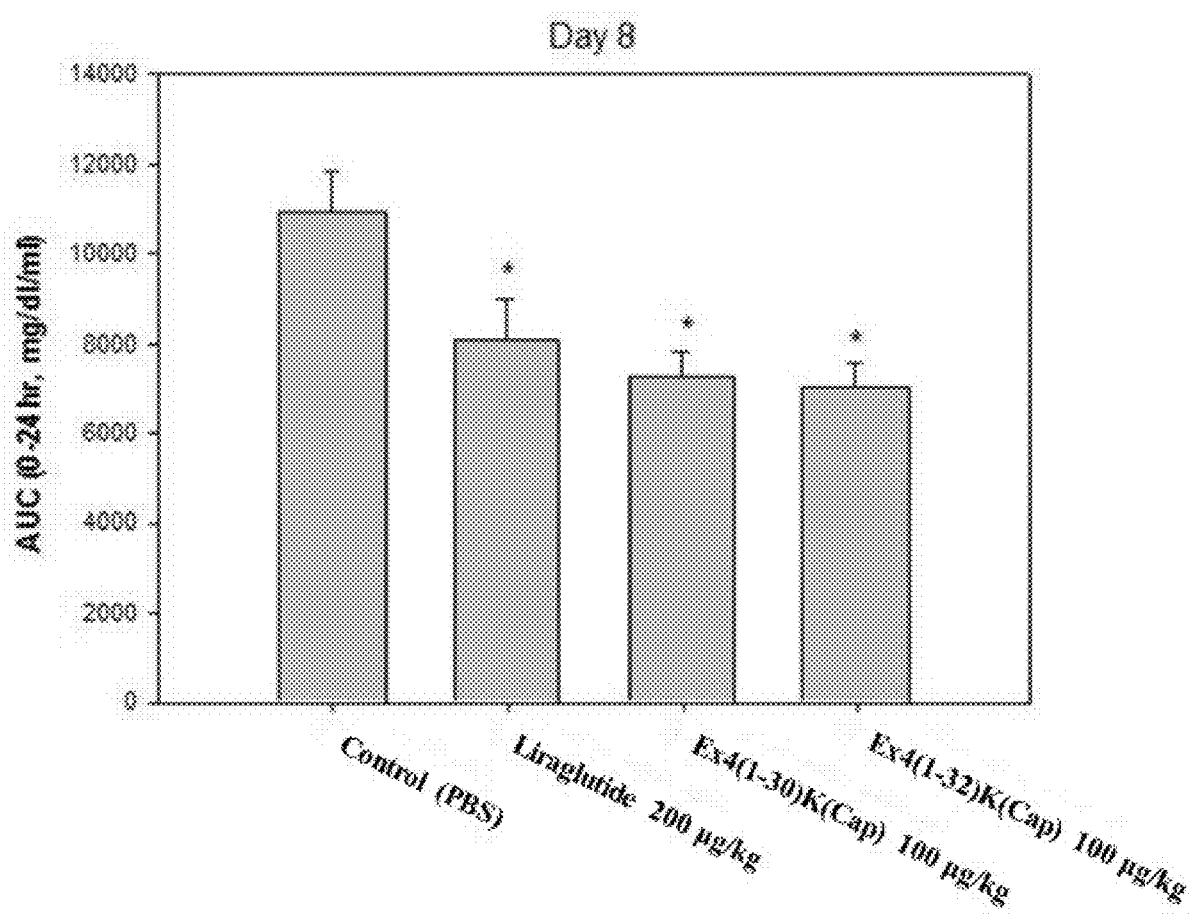
Figure 12A:
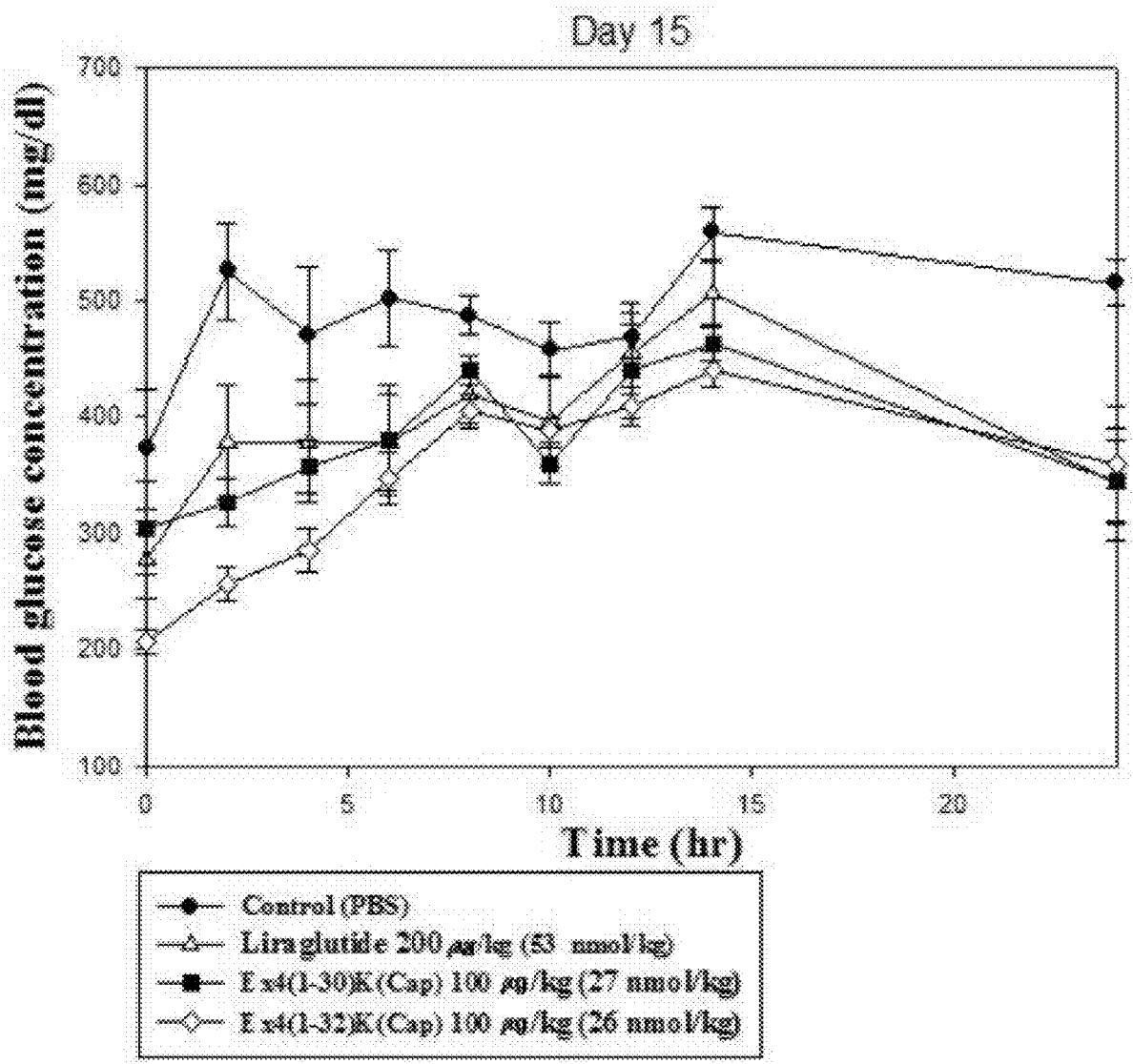
FIGS. 12a and 12b show blood glucose measurement results on day 15 in the effect comparison test of liraglutide and short exendin-4-fatty acid conjugates.
Figure 12B:
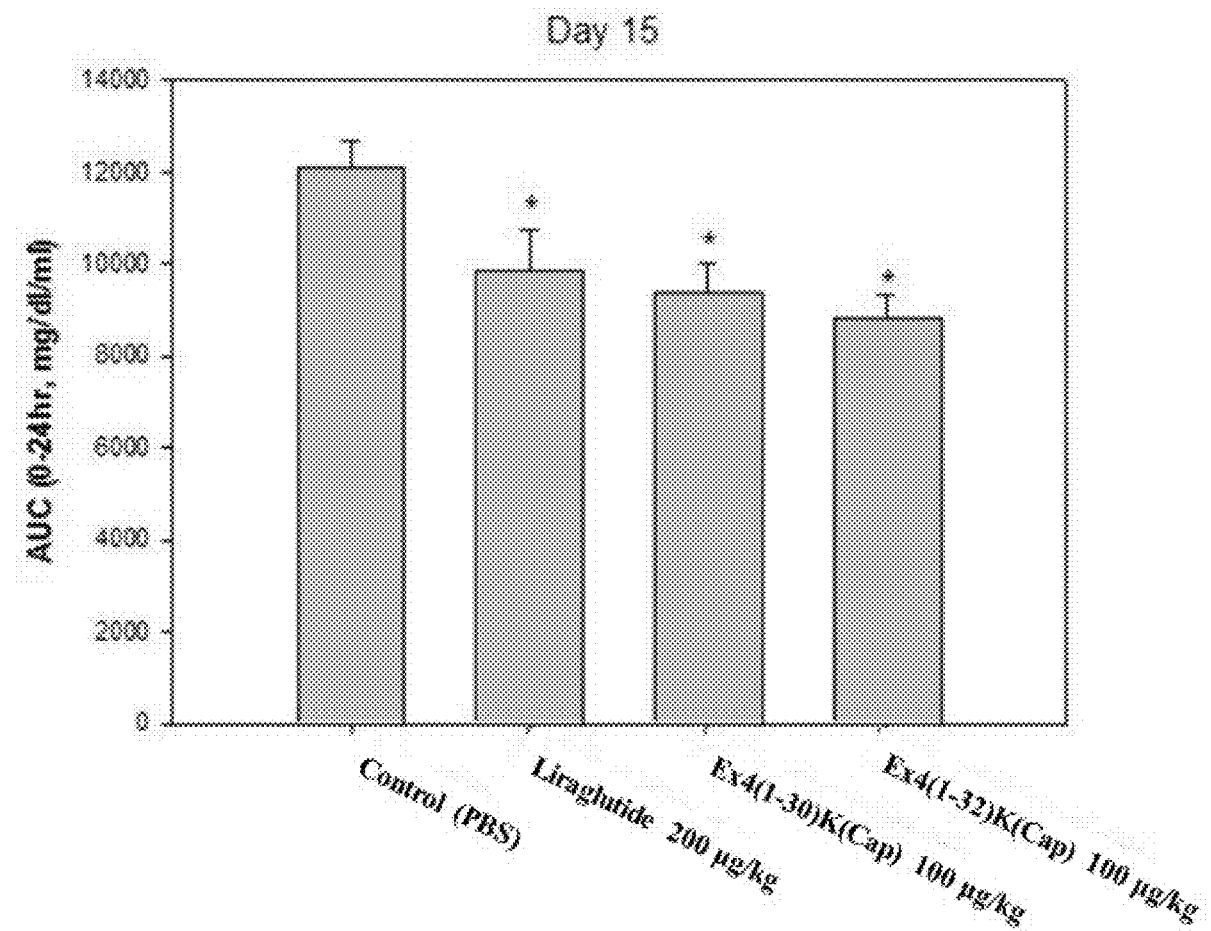

Comparative Test of Concentration-Dependent Effect of Short Exendin-4-Fatty Acid Conjugates Using Diabetes Model Mice Four kinds of short exendin-4-fatty acid conjugates with two concentrations were prepared. After male db/db mice (6-12 week aged) were subcutaneously administered with Ex4(1-30)K-Pal, Ex4(1-30)K-Cap, Ex4(1-32)K-Pal, and Ex4(1-32)K-Cap at concentrations of 1 nmol/kg and 5 nmol/kg for each, and then, at hour 0, 1, 2, 4, 6, 8, 12, 19, and 24, the blood was collected from the end of the tail of the mice to measure the blood glucose using a blood glucose monitor. As a result, all the four kinds of conjugates showed a concentration-dependent blood glucose lowering effect similar to that of the positive control, exenatide (FIGS. 9a and 9b).

Comparative Test of Effect of Short Exendin-4-Fatty Acid Conjugates Using Diabetes Model Mice The male db/db mice (6-12 week aged) were subcutaneously administered with 200 μg/kg liraglutide, 100 μg/kg Ex4(1-30)K-Cap, and 100 μg/kg Ex4(1-32)K-Cap. After 1, 8, and 15 days, for the observation of the blood glucose lowering effect, at hour 0, 1, 2, 4, 6, 8, 12, 19, and 24, the blood was collected from the end of the tail of the mice to measure the blood glucose using a blood glucose monitor. As a result, it was verified that, at all the hours, Ex4(1-30)K-Cap and Ex4(1-32)K-Cap(C) showed a similar or more excellent effect compared with liraglutide (AUC comparison), and showed an equal or lower glucose sugar value at hour 24, compared with liraglutide. This test verified that Ex4(1-30)K-Cap and Ex4(1-32)K-Cap can have efficacy duration similar to that of liraglutide (FIGS. 10a to 12b).

Figure 13A:
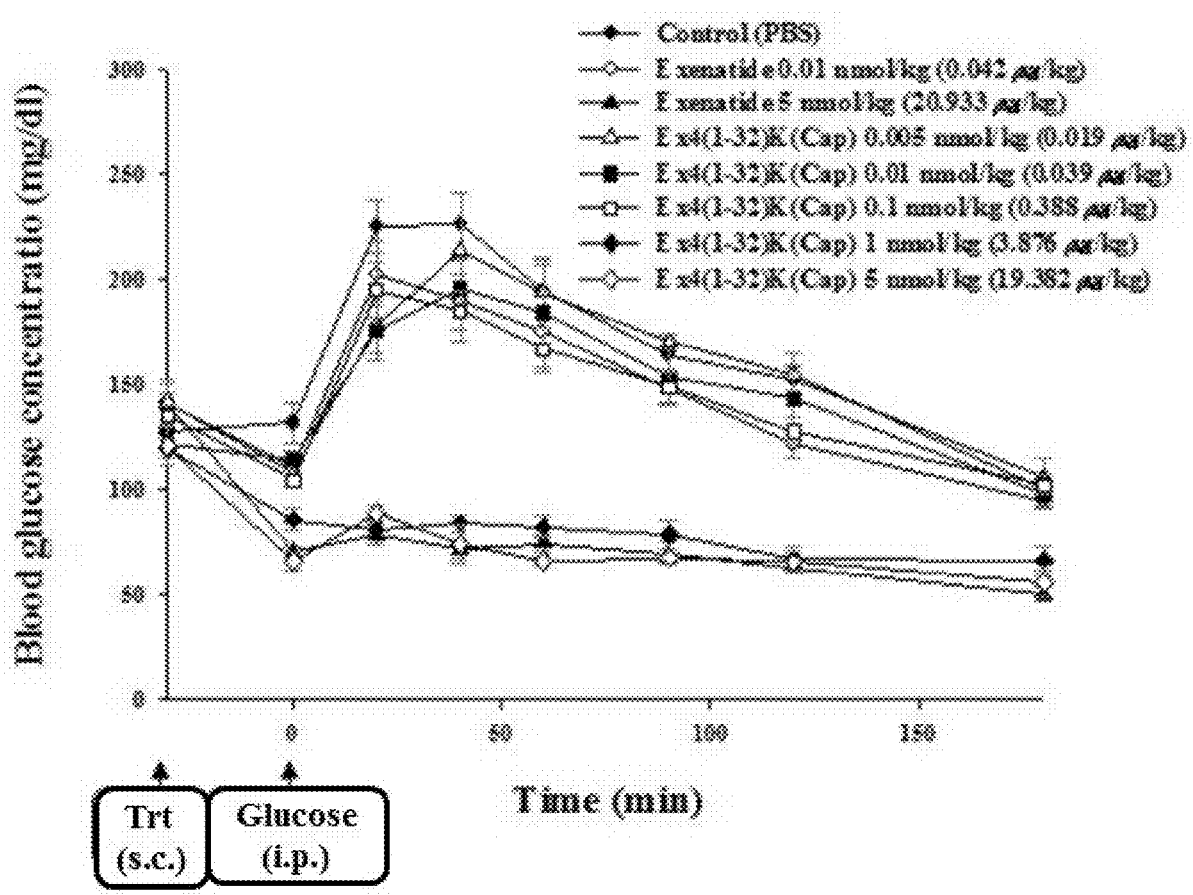
FIGS. 13a and 13b show the blood glucose lowering effect by subcutaneous administration of Ex4(1-32)K(Cap) using diabetic model mice.
Figure 13B:
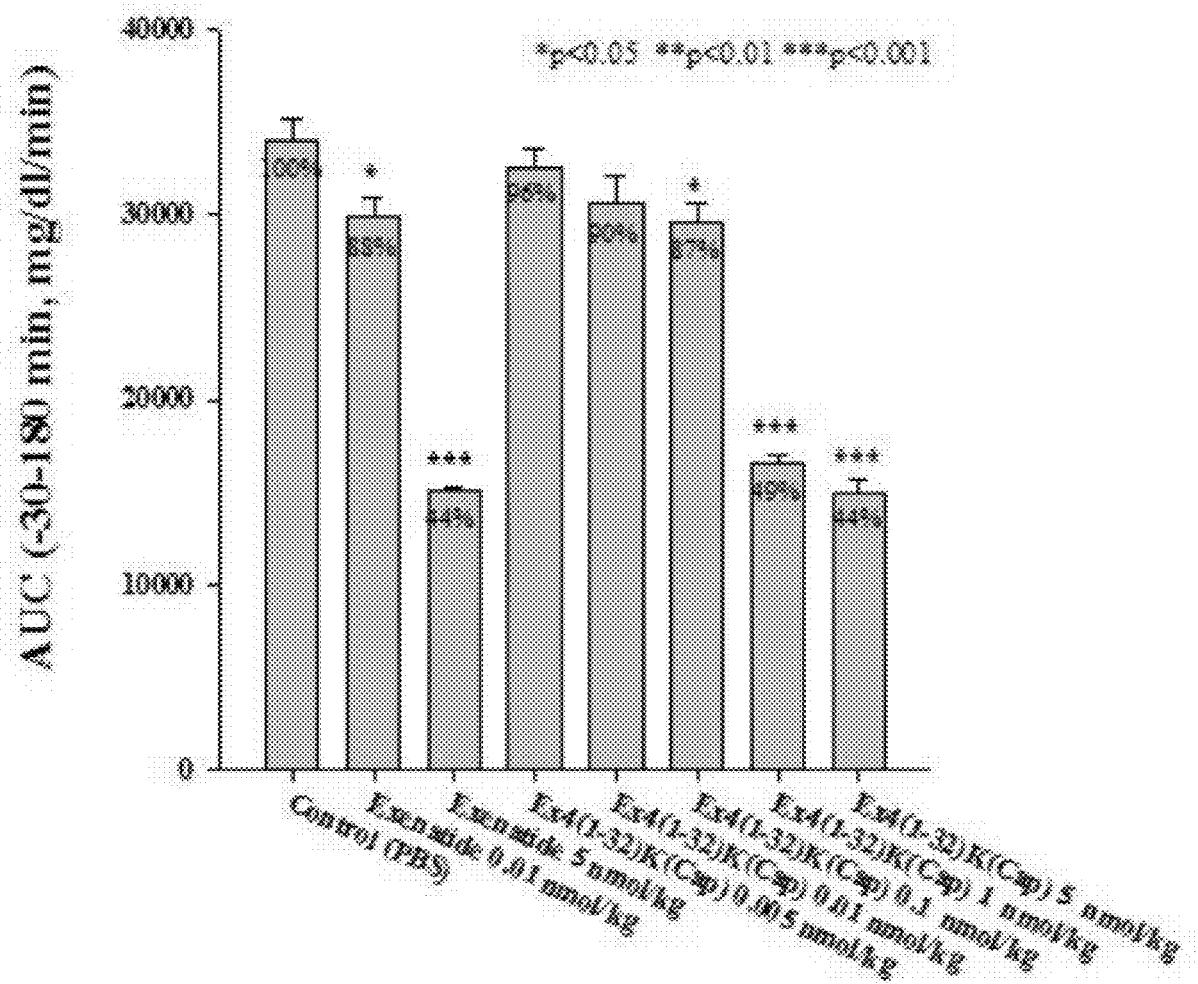

Example 3: Characterization of Ex4(1-32)K-Cap (Subcutaneous) Glucose Tolerance Test of Ex4(1-32)K(Cap) Using Diabetic Model Mice After male db/db mice (6-12 week aged) were fasted for 18 hours, the fasted diabetic model mice were (subcutaneously) administered with the short exenatide-fatty acid conjugate Ex4(1-32)K(Cap) at concentrations of 0.005 nmol/kg, 0.01 nmol/kg, 0.1 nmol/kg, 1 nmol/kg, and 5 nmol/kg, and then after 30 minutes, abdominally administered with glucose (1.5 g/kg). After 0, 20, 40, 60, 90, 120, and 180 minutes, the blood was collected from the end of the tail of the mice to check the blood glucose using a blood glucose monitor. As a result, it was verified that Ex4(1-32)K(Cap) showed a concentration-dependent blood glucose lowering effect (FIGS. 13a and 13b).

Figure 14A:
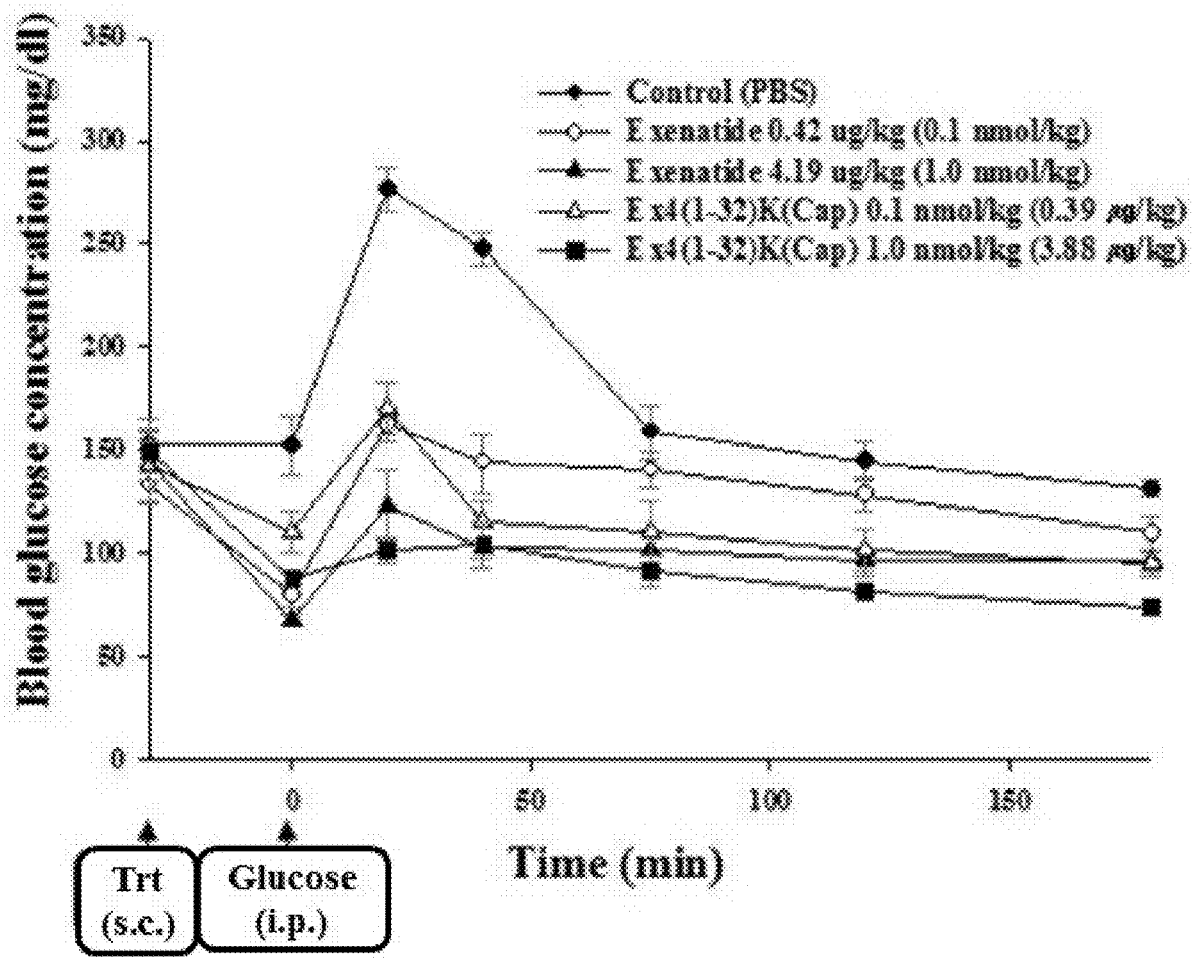
FIGS. 14a and 14b show glucose tolerance by subcutaneous administration of Ex4(1-32)K(Cap) using diabetic model mice.
Figure 14B:
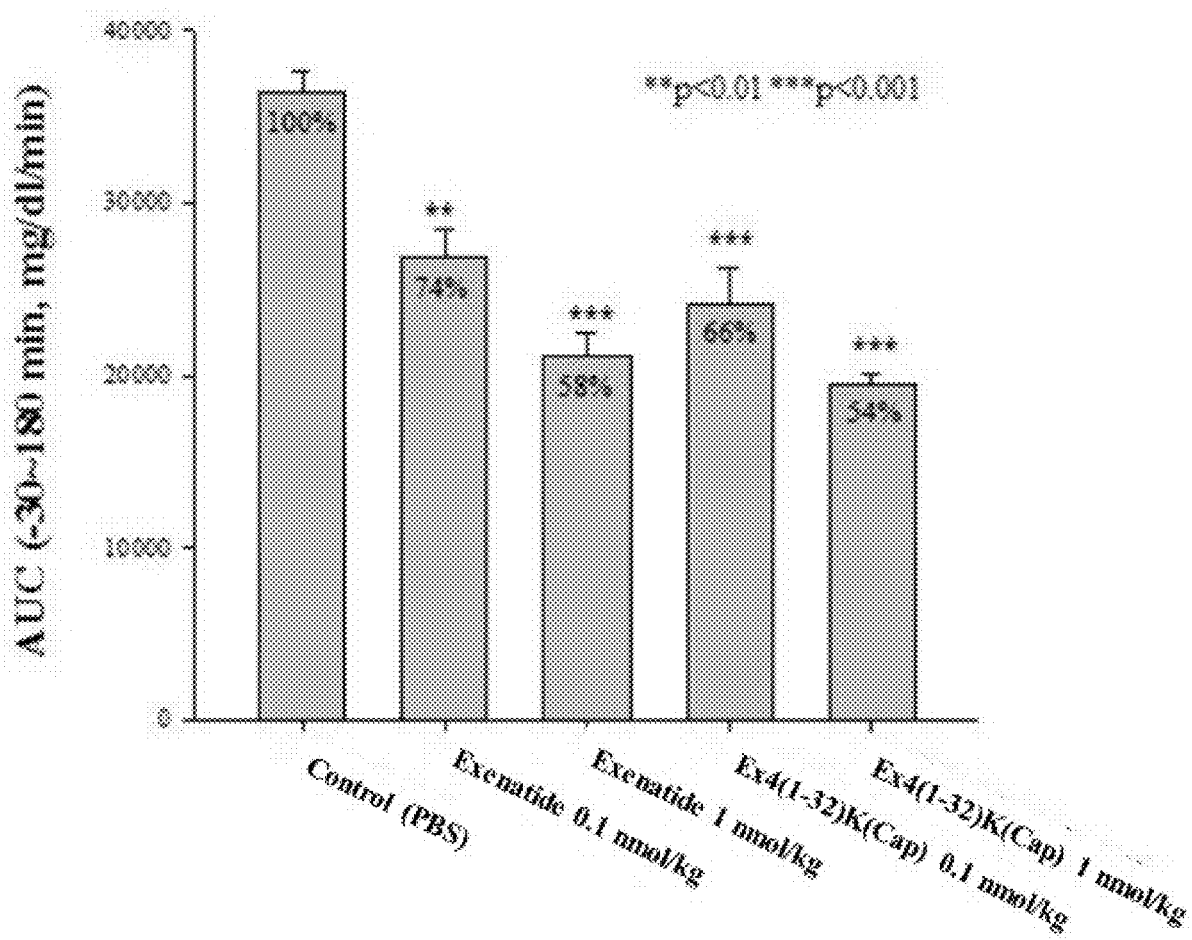

For the comparison with exenatide as a positive control, the fasted mice were (subcutaneously) administered with Ex4(1-32)K(Cap) and exenatide at concentrations of 0.1 nmol/kg and 1 nmol/kg for each, and then after 30 minutes, abdominally administered with glucose (1.5 g/kg). After 0, 20, 40, 75, 120, and 180 minutes, the blood was collected from the end of the tail of the mice, and then the blood glucose was measured using a blood glucose monitor to check the glucose tolerance ability. As a result, it was verified that Ex4(1-32)K(Cap) had a concentration-dependent blood glucose lowering effect, and significant glucose tolerance similar to that of exenatide (FIGS. 14a and 14b).

Figure 15A:
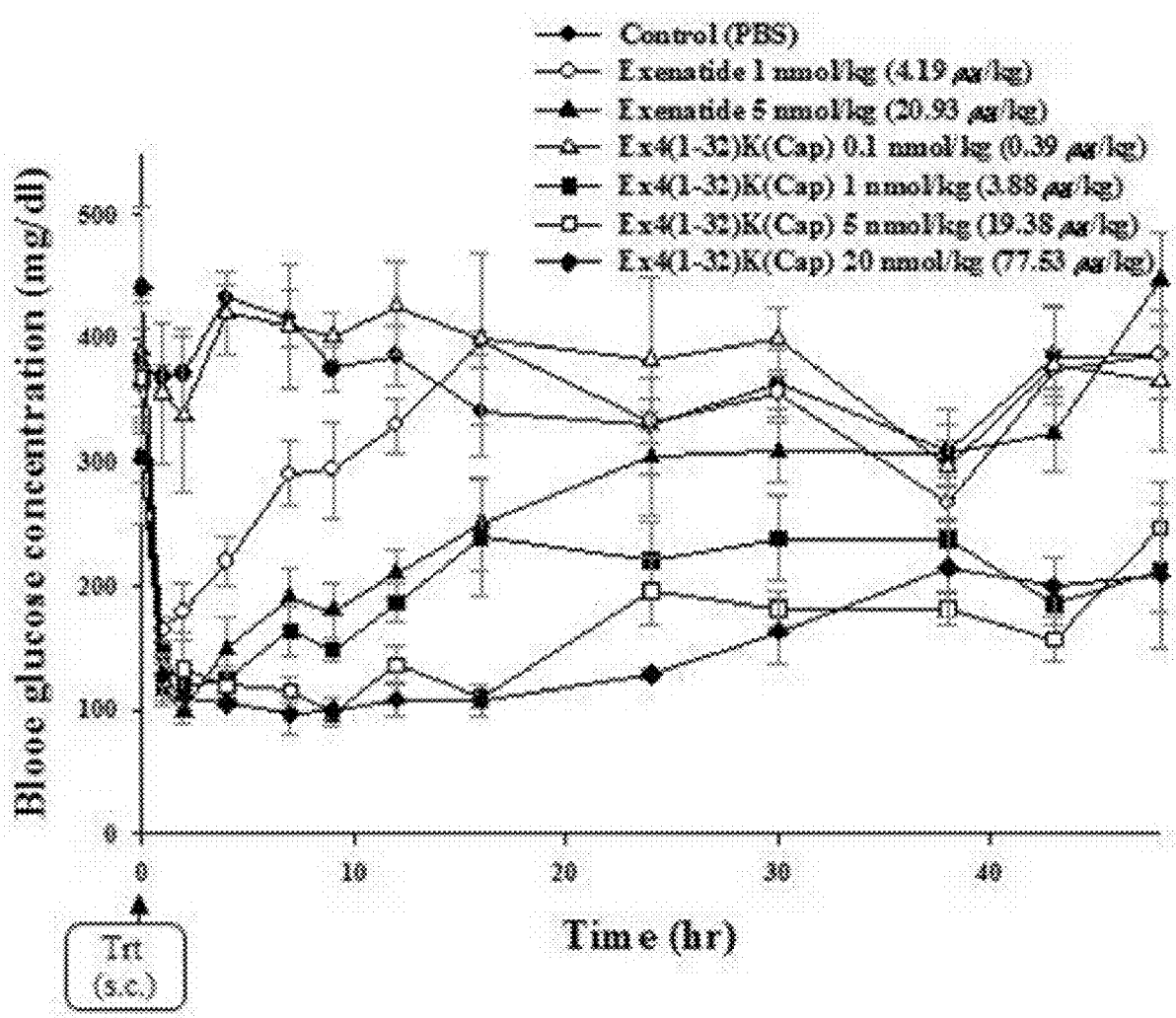
FIGS. 15a and 15b show the long-time blood glucose lowering effect by subcutaneous administration of Ex4(1-32)K(Cap) using diabetic model mice.
Figure 15B:
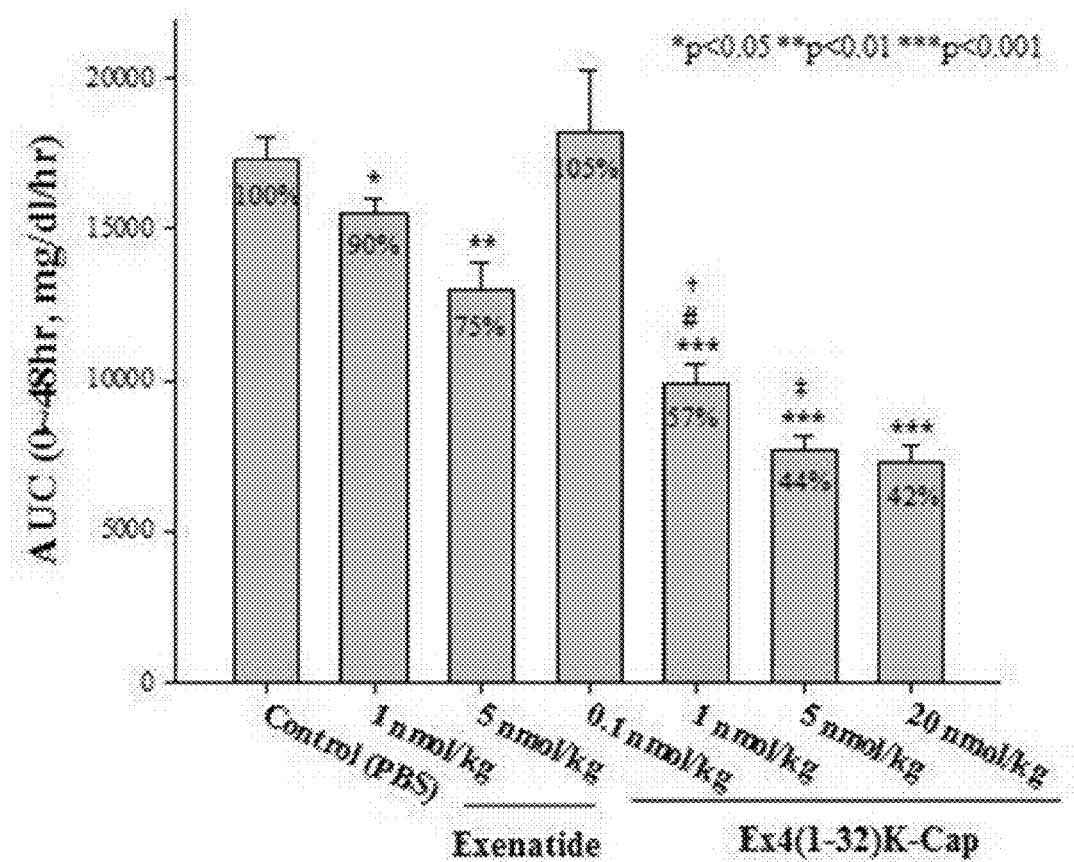

(Subcutaneous) Antidiabetic Effect Test of Ex4(1-32)K(Cap) Using Diabetic Model Mice The male db/db mice (6-12 week aged) were (subcutaneously) administered with the short exenatide-fatty acid conjugate, Ex4(1-32)K(Cap), at concentrations of 0.1 nmol/kg, 1 nmol/kg, 5 nmol/kg, and 20 nmol/kg, and, for the comparison with exenatide as a positive control, exenatide at concentrations of 1 nmol/kg and 5 nmol/kg, and then at hour 0, 1, 2, 4, 7, 9, 12, 16, 24, 38, 43, and 48, the blood was collected from the end of the tail of the mice to check the blood glucose lowering effect. As a result, it was verified that Ex4(1-32)K(Cap) had a concentration-dependent blood glucose lowering effect, and, when administered at the same doses, 1 nmol/kg and 5 nmol/kg, exenatide as a positive control showed the recovery to the initial blood glucose within 24 hours, whereas Ex4(1-32)K(Cap) showed the blood glucose lowering remaining effect for 48 hours, indicating a more excellent blood glucose lowering effect (FIGS. 15a and 15b).

Figure 16A:
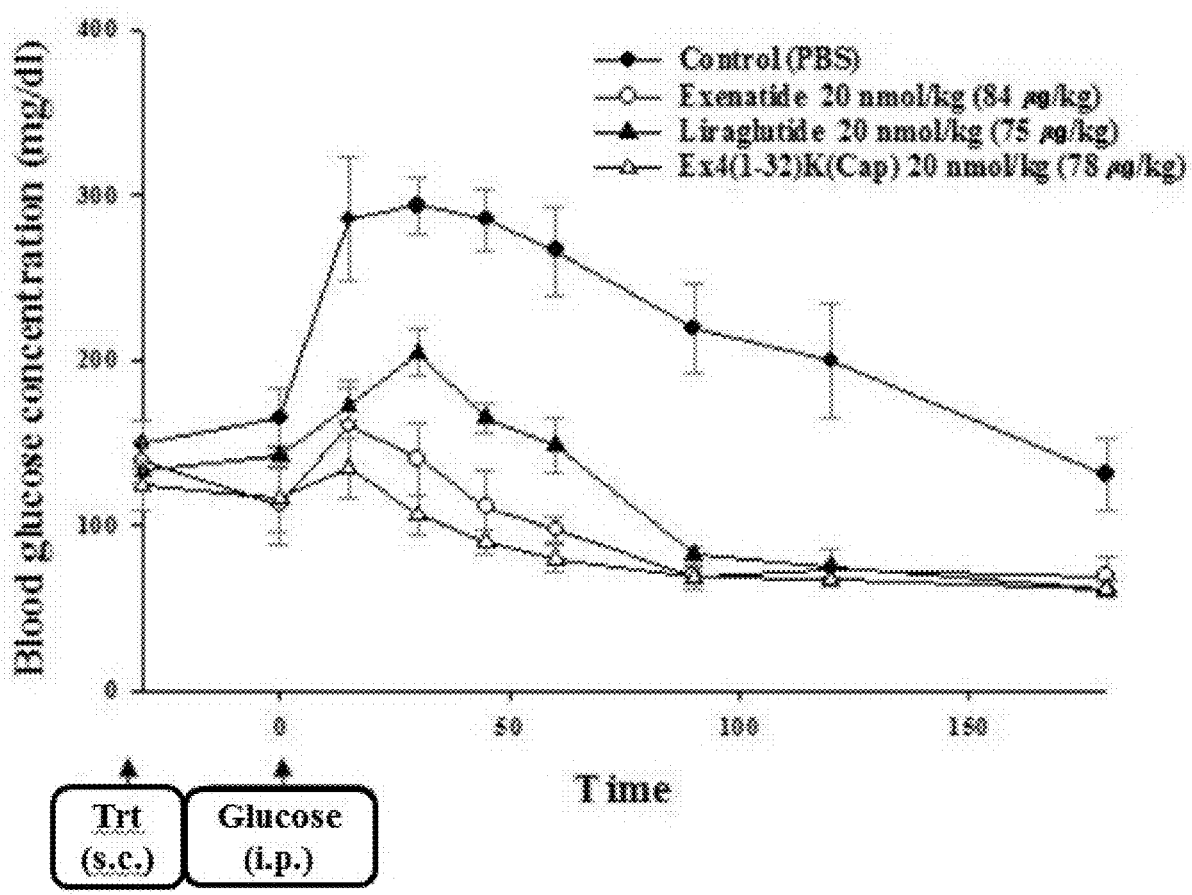
FIGS. 16a and 16b show glucose tolerance by subcutaneous administration of Ex4(1-32)K(Cap) using diabetic model mice, compared with exenatide and liraglutide.
Figure 16B:
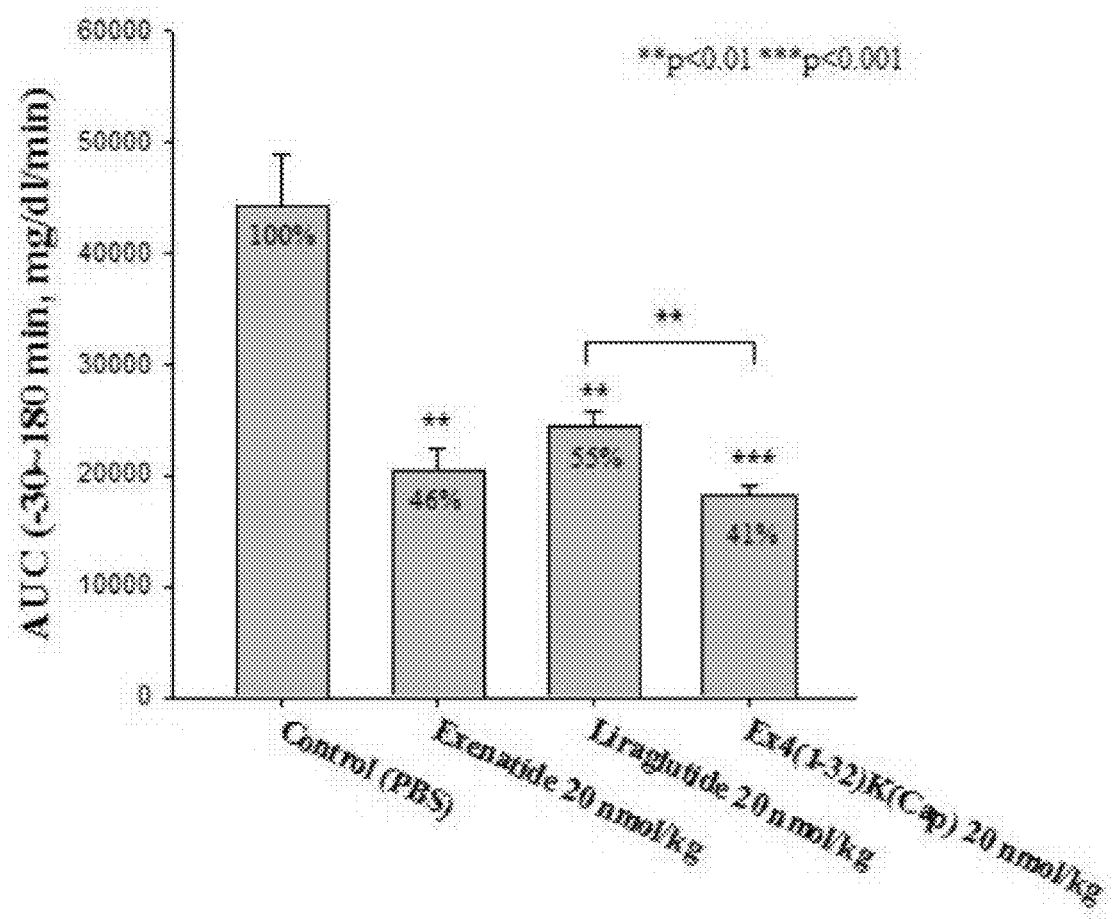

Comparative Test of (Subcutaneous) Effect of Ex4(1-32)K(Cap) Using Diabetic Model Mice For the comparison of the blood glucose lowering effect between the exenatide analog and liraglutide, the db/db mice fasted for 18 hours were subcutaneously administered with the short exenatide-fatty acid conjugate Ex4(1-32)K(Cap) as positive control, exenatide, and liraglutide at a concentration of 20 nmol/kg for each, and then abdominally administered with glucose (1.5 g/kg). After 0, 20, 40, 60, 90, 120, and 180 minutes, the glucose tolerance ability of the drugs was checked. As a result, it was verified that Ex4(1-32)K(Cap) had significant glucose tolerance similar to those of exenatide as a positive control and liraglutide (FIGS. 16a and 16b).

Figure 17A:
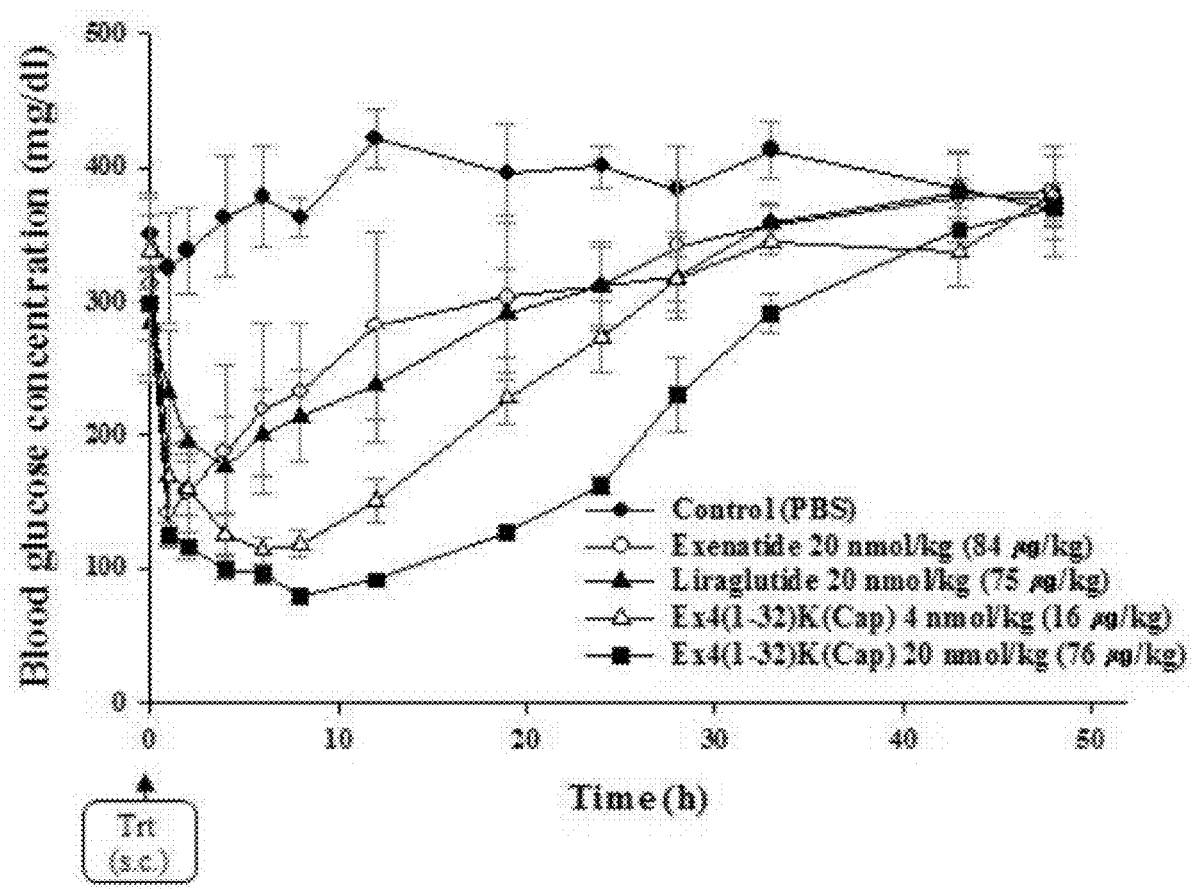
FIGS. 17a and 17b show the blood glucose lowering effect by subcutaneous administration of Ex4(1-32)K(Cap) using diabetic model mice, compared with exenatide and liraglutide.
Figure 17B:
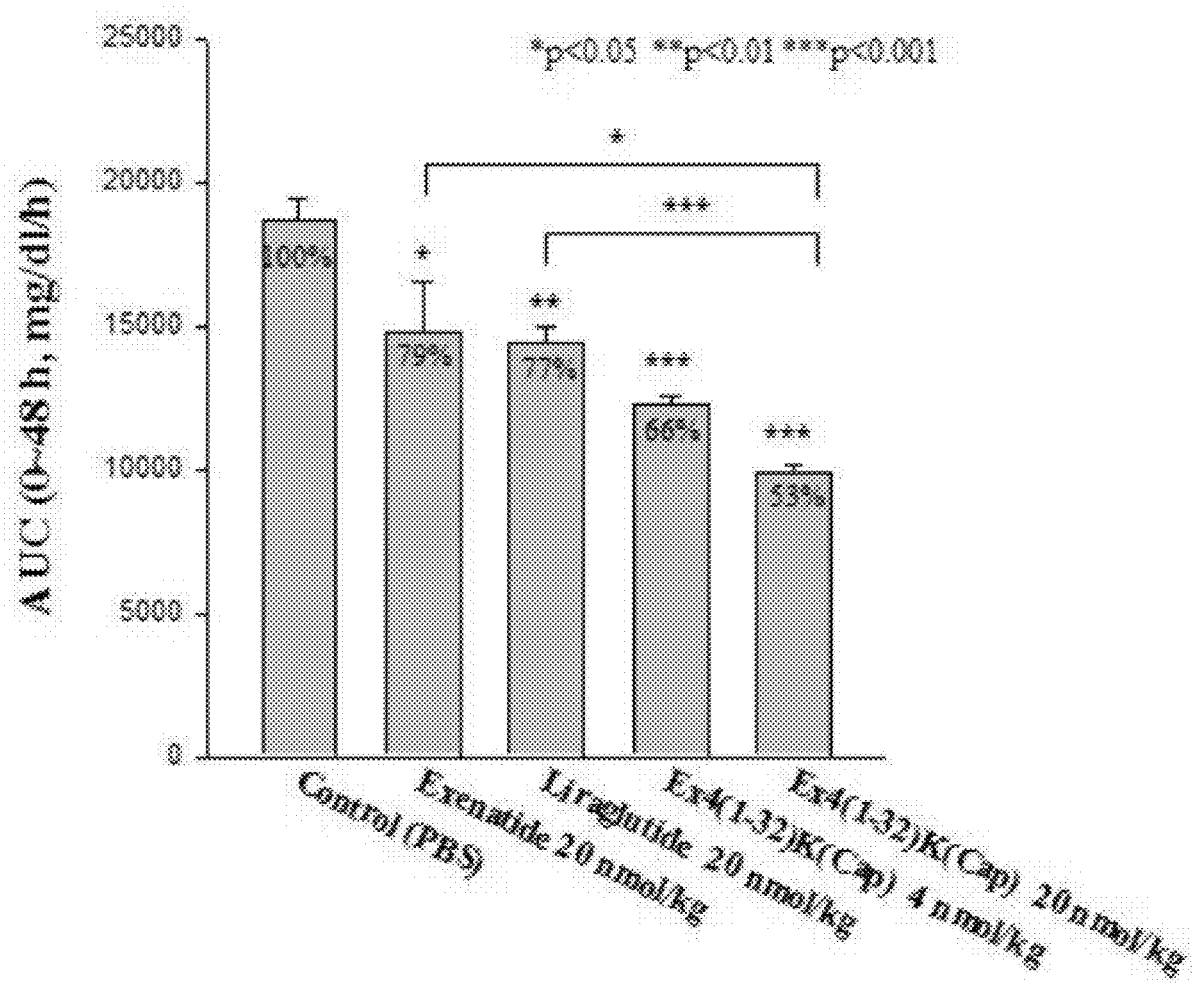

For the comparison with exenatide and liraglutide as positive controls, diabetic model mice were subcutaneously administered with the short exenatide-fatty acid conjugate Ex4(1-32)K(Cap) at concentrations of 4 nmol/kg and 20 nmol/kg, and exenatide and liraglutide at a concentration of 20 nmol/kg for each, and then, after 0, 1, 2, 4, 6, 8, 12, 19, 24, 28, 33, 43, and 48 hours, the blood glucose lowering effect was checked. As a result, it was verified that Ex4(1-32)K(Cap) showed a more excellent blood glucose lowering effect than exenatide and liraglutide as positive controls (FIGS. 17a and 17b).

Comparative Test of (Oral) Effect of Ex4(1-32)K(Cap) Using Diabetic Model Mice

Figure 18A:
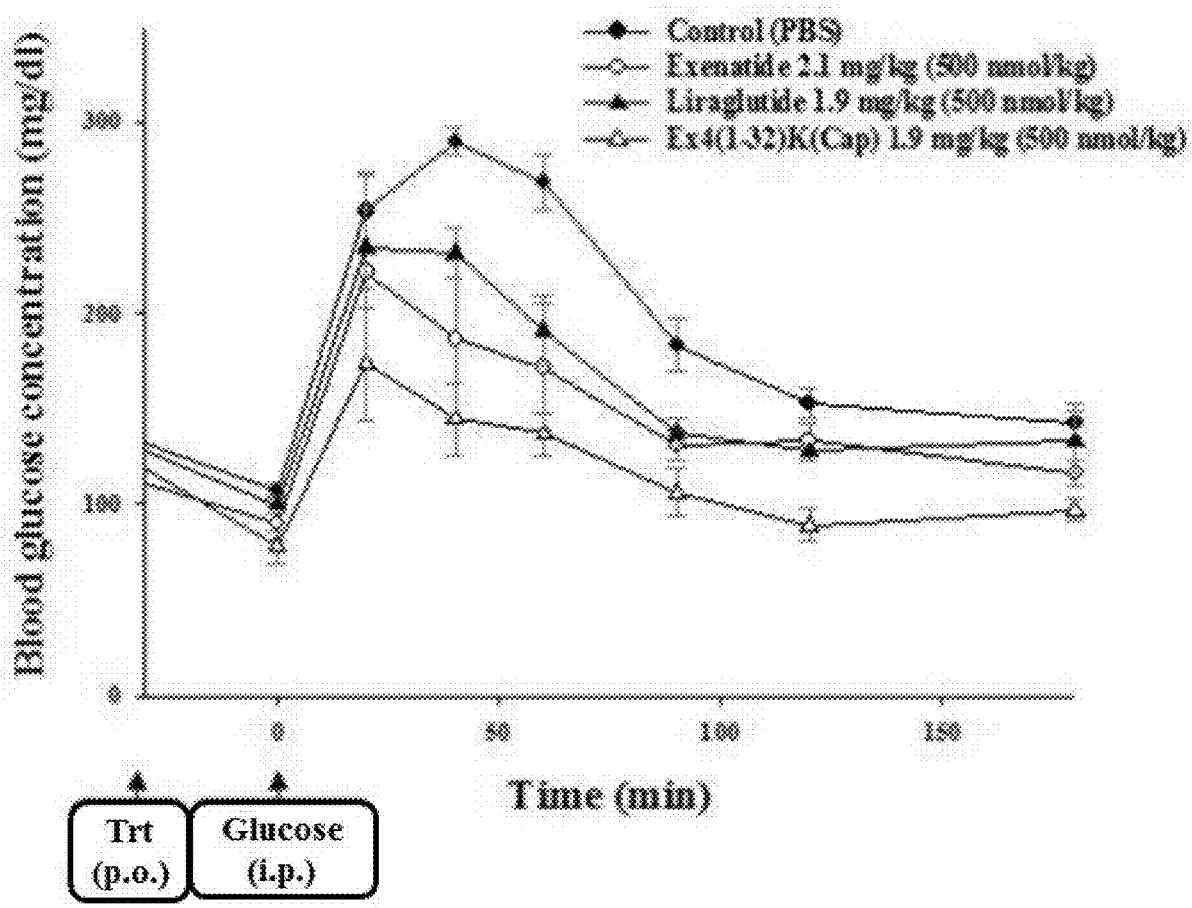
FIGS. 18a and 18b show glucose tolerance by oral administration of Ex4(1-32)K(Cap) using diabetic model mice, compared with exenatide and liraglutide.
Figure 18B:
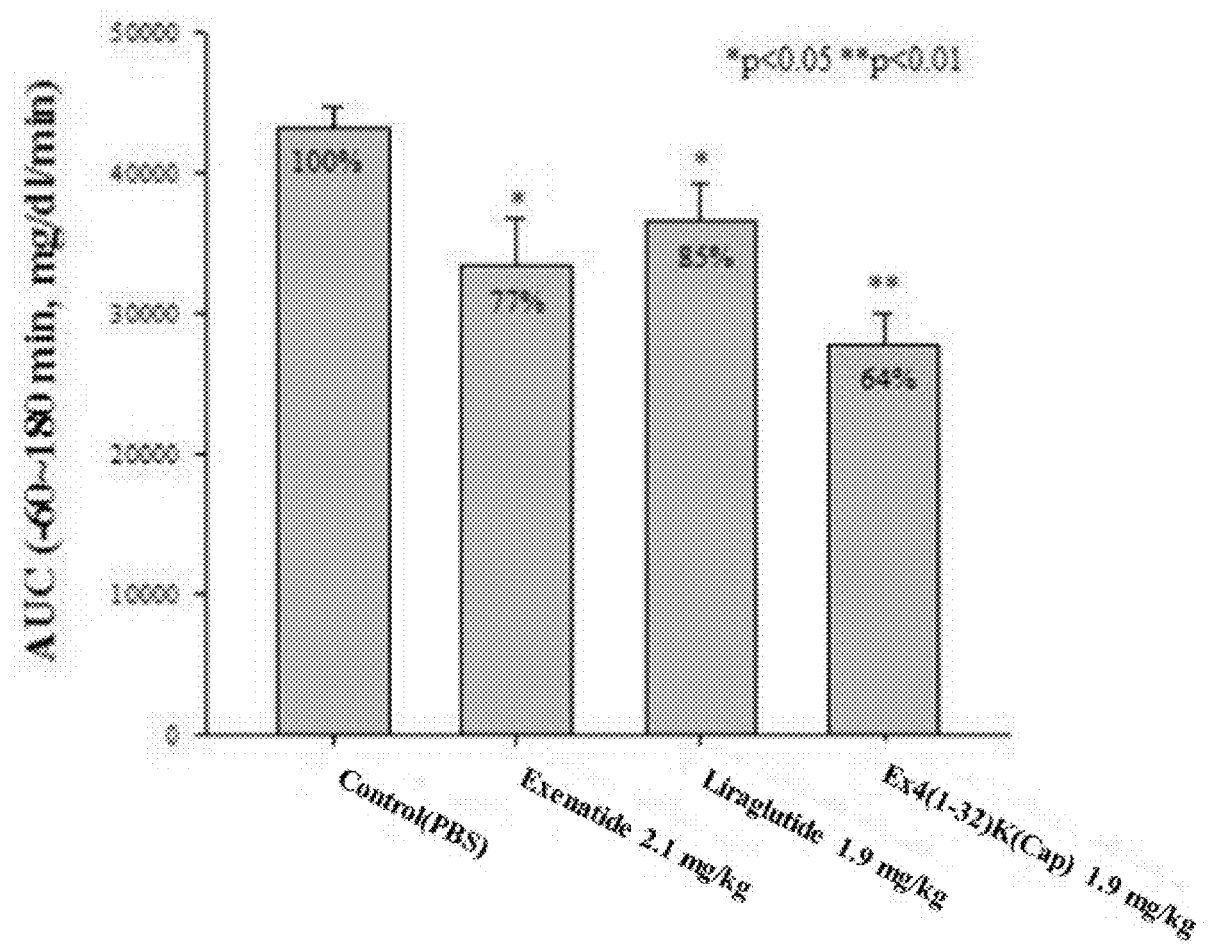

The ob/ob mice (6-12 week aged) fasted for 18 hours were (orally) administered with the short exenatide-fatty acid conjugate Ex4(1-32)K(Cap) at a concentration of 1.9 mg/kg (500 nmol/kg), and then abdominally administered with glucose. After 0, 20, 40, 60, 90, 120, and 180 minutes, the glucose tolerance ability of the drugs was checked. As a result, it was verified that Ex4(1-32)K(Cap) had significant glucose tolerance, which was more excellent than that of liraglutide as a positive control at the time of oral administration (FIGS. 18a and 18b).

(Oral) Glucose Tolerance Test of Ex4(1-32)K(Cap) Using Diabetic Model Mice

Figure 19A:
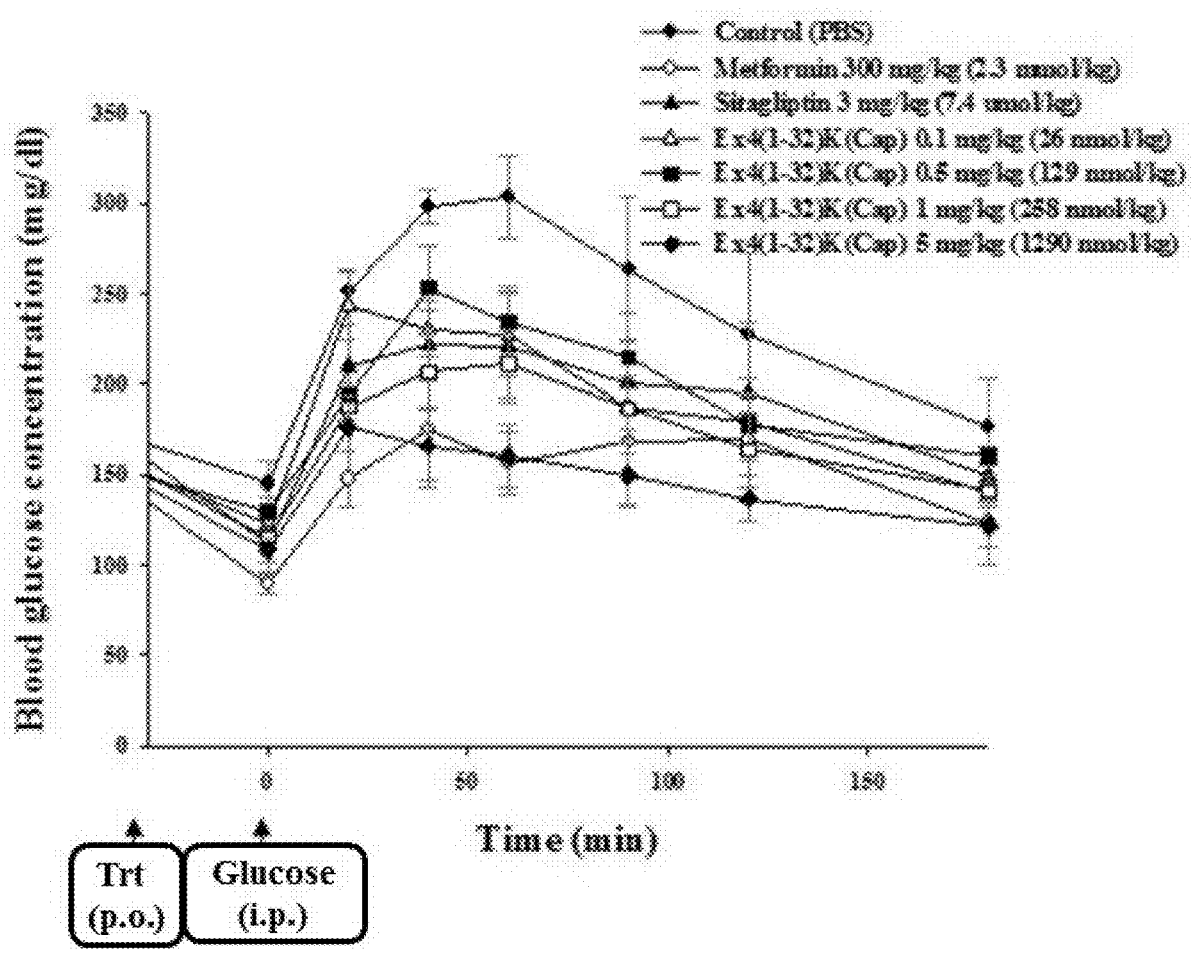
FIGS. 19a and 19b show the blood glucose lowering effect by oral administration of Ex4(1-32)K(Cap) using diabetic model mice.
Figure 19B:
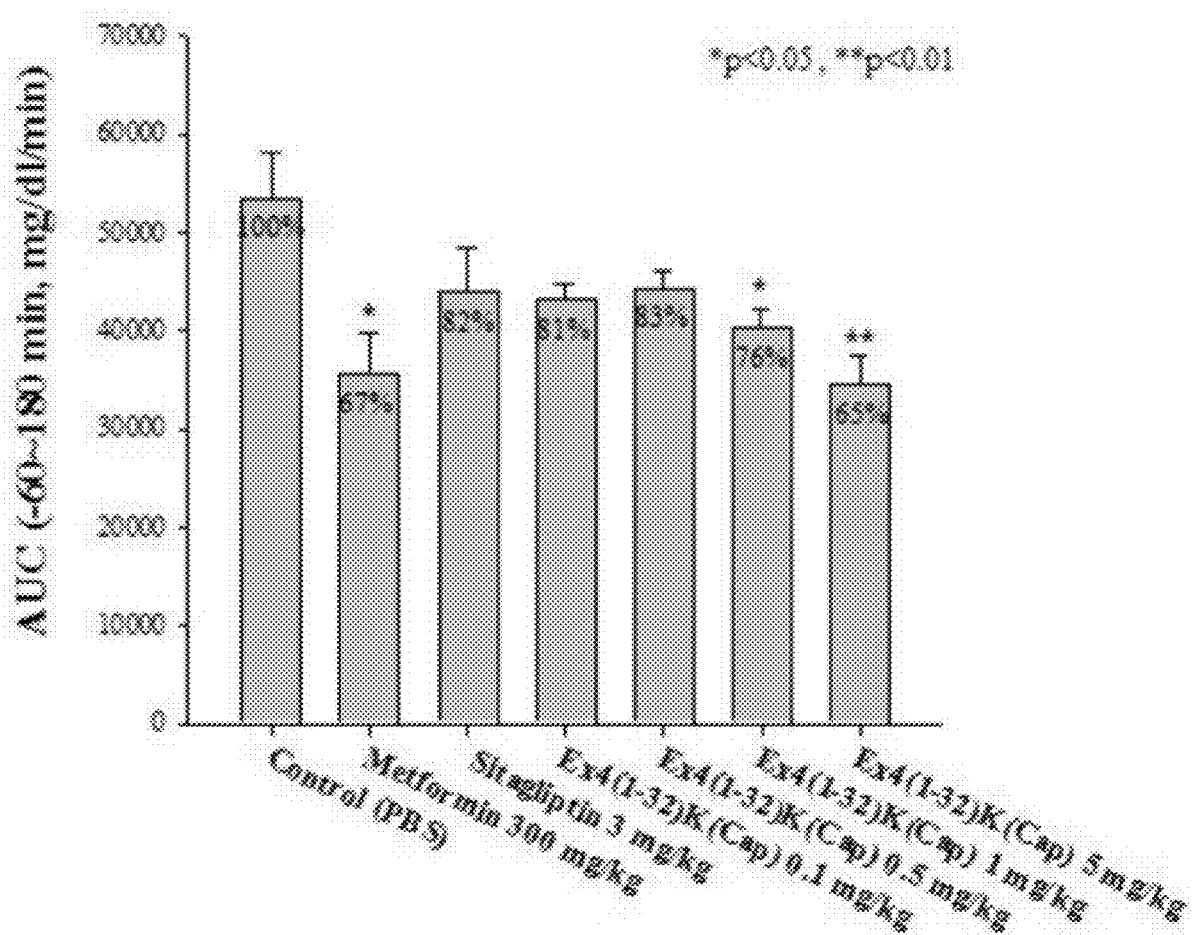

The ob/ob mice (6-12 week aged) fasted for 18 hours were (orally) administered with the short exenatide-fatty acid conjugate Ex4(1-32)K(Cap) at concentrations of 0.1 mg/kg, 0.5 mg/kg 1 mg/kg, and 5 mg/kg, and then abdominally administered with glucose. After 0, 20, 40, 60, 90, 120, and 180 minutes, the glucose tolerance ability of the drugs was checked. As a result, it was verified that Ex4(1-32)K(Cap) had a concentration-dependent blood glucose lowering effect (FIGS. 19a and 19b).

Figure 20A:
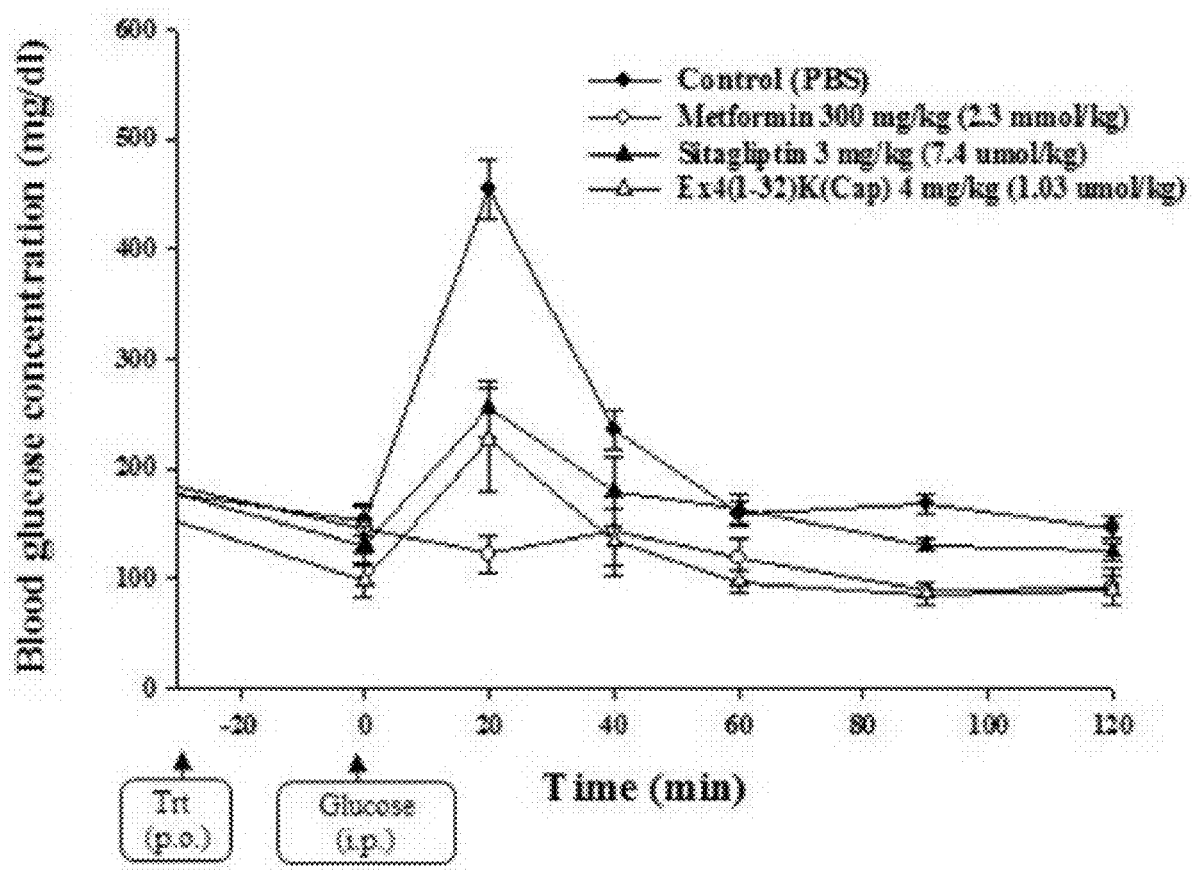
FIGS. 20a and 20b show the blood glucose lowering effect by oral administration of Ex4(1-32)K(Cap) using diabetic model mice, compared with metformin and sitagliptin.
Figure 20B:
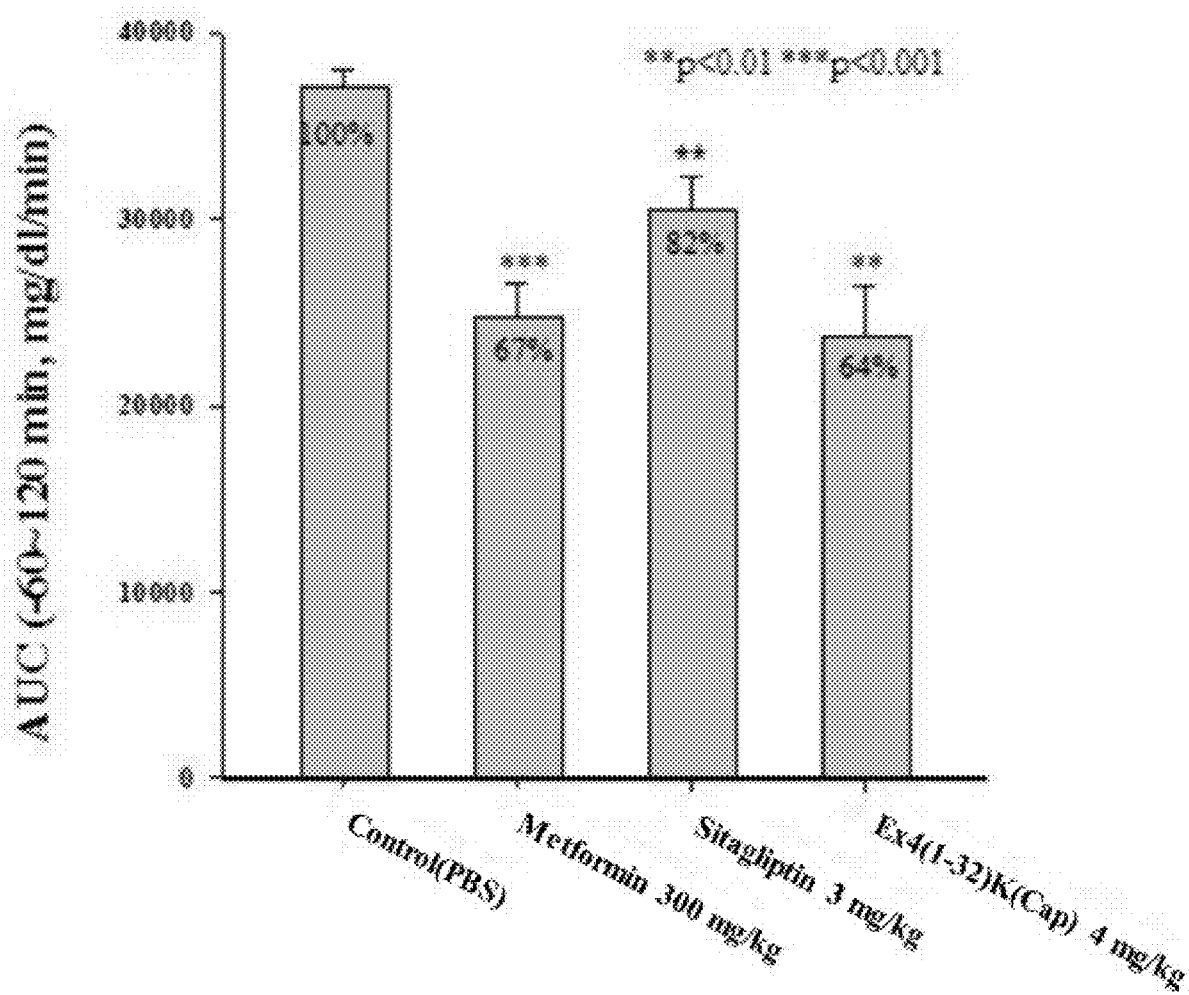

Comparative Test 2 of (Oral) Effect of Ex4(1-32)K(Cap) Using Diabetic Model Mice For the comparison with metformin and sitagliptin as positive controls, the db/db mice fasted for 18 hours were administered with the short exenatide-fatty acid conjugate Ex4(1-32)K(Cap) at a concentration of 4 mg/kg, metformin at 300 mg/kg and sitagliptin at 3 mg/kg, and then abdominally administered with glucose. After 0, 20, 40, 60, 90, 120, and 180 minutes, the glucose tolerance ability of the drugs was checked. As a result, it was verified that Ex4(1-32)K(Cap) had a significant glucose tolerance similar to those of metformin and sitagliptin (FIGS. 20a and 20b).

Figure 21A:
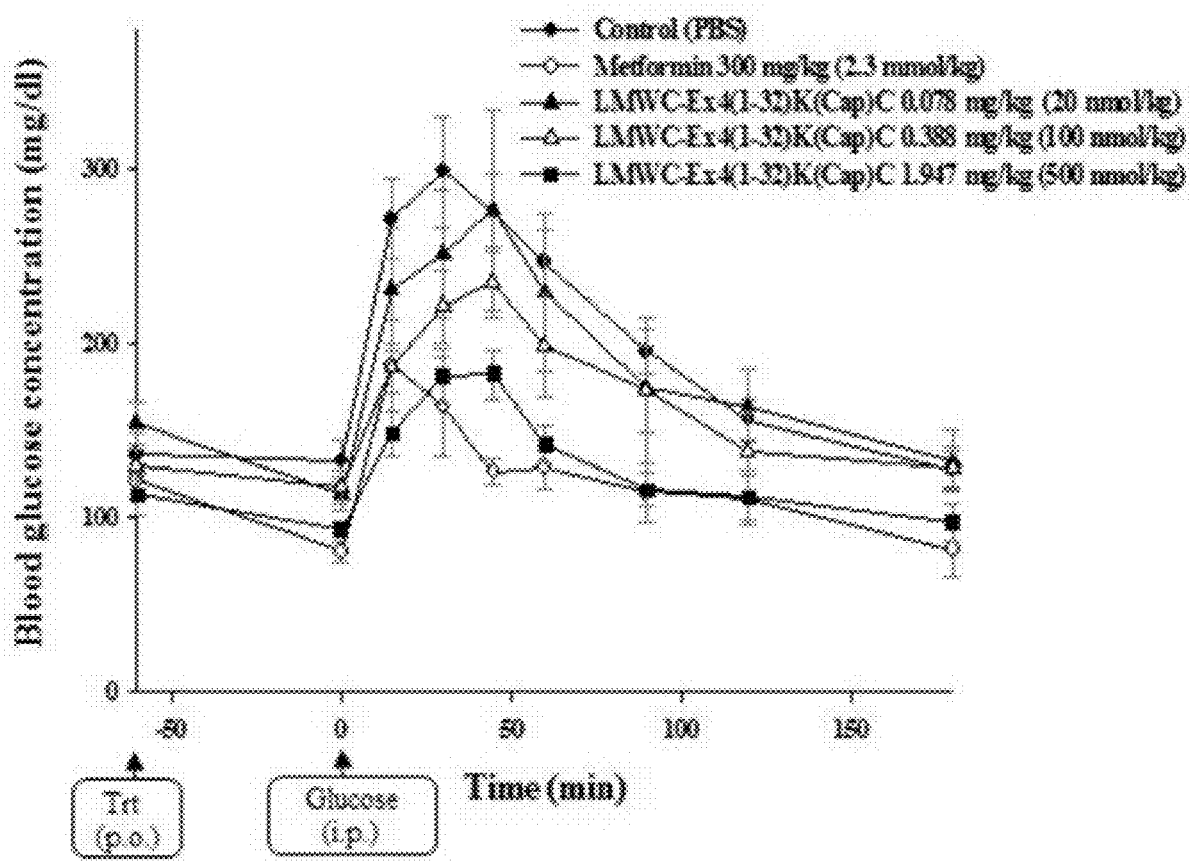
FIGS. 21a and 21b show glucose tolerance by oral administration of LMWC-Ex4(1-32)K(Cap) using diabetic model mice, compared with metformin.
Figure 21B:
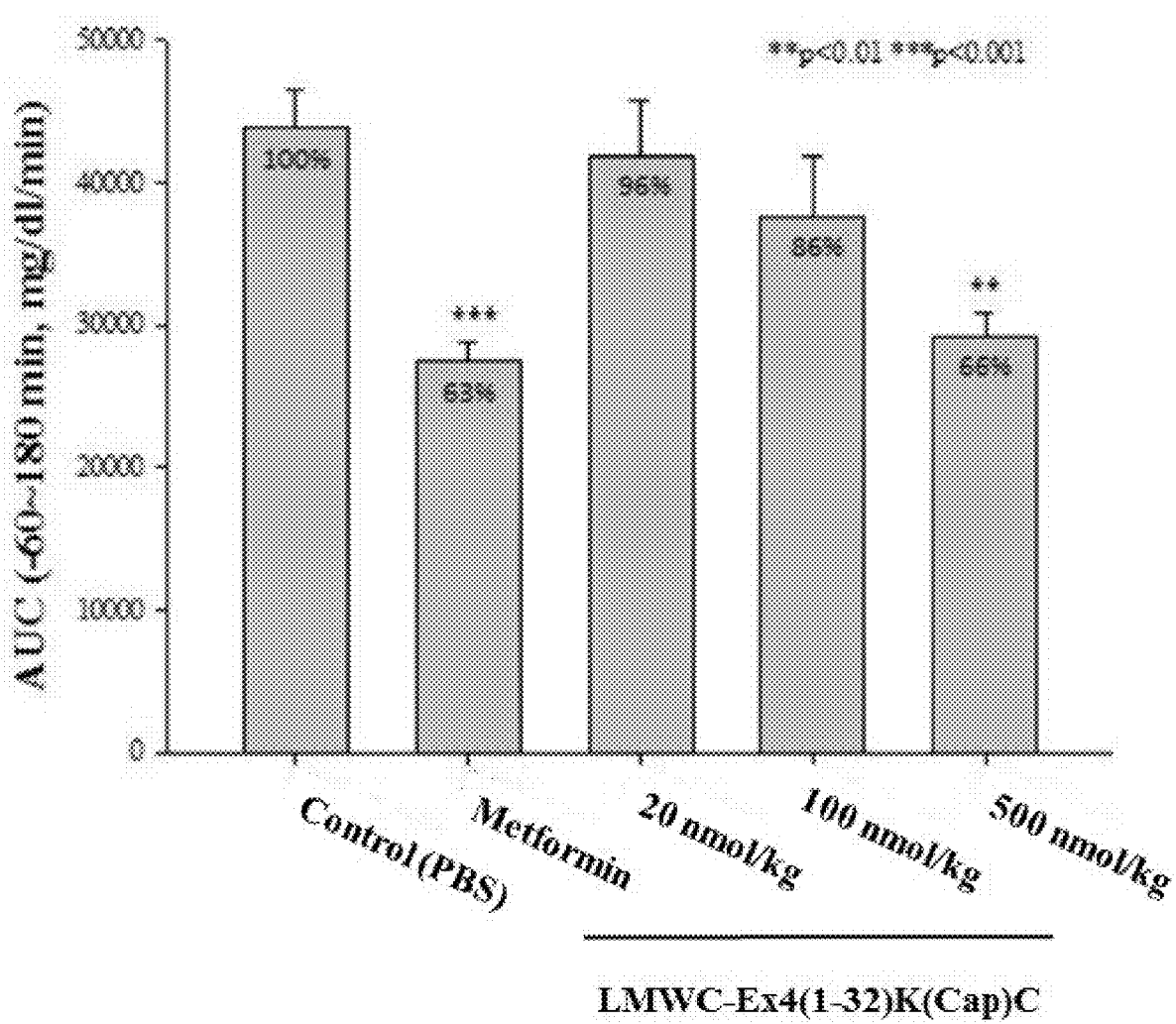

Example 4: Effect Analysis of LMWC-Ex4(1-32)K(Cap)C (Oral) Glucose Tolerance Test of LMWC-Ex4(1-32)K(Cap) Conjugate Using Diabetic Model Mice LMWC-Ex4(1-32)K(Cap)C was prepared by conjugating LMWC to the short exenatide-fatty acid conjugate Ex4(1-32)K(Cap). LMWC is a drug delivery that does not influence the activity of the C-terminal of exenatide analogs. LMWC-Ex4(1-32)K(Cap)C was administered at doses of 0.078 mg/kg (20 nmol/kg), 0.388 mg/kg (100 nmol/kg), and 1.947 mg/kg (500 nmol/kg), and glucose was administered. After 0, 20, 40, 60, 90, 120, and 180 minutes, the blood was collected from the end of the tail of the mice to check the glucose tolerance ability. As a result, it was verified that LMWC-Ex4(1-32)K(Cap)C, when orally administered at a dose of 1.947 mg/kg (500 nmol/kg), had significant glucose tolerance similar to that of metformin as a positive control (FIGS. 21a and 21b).

Figure 22A:
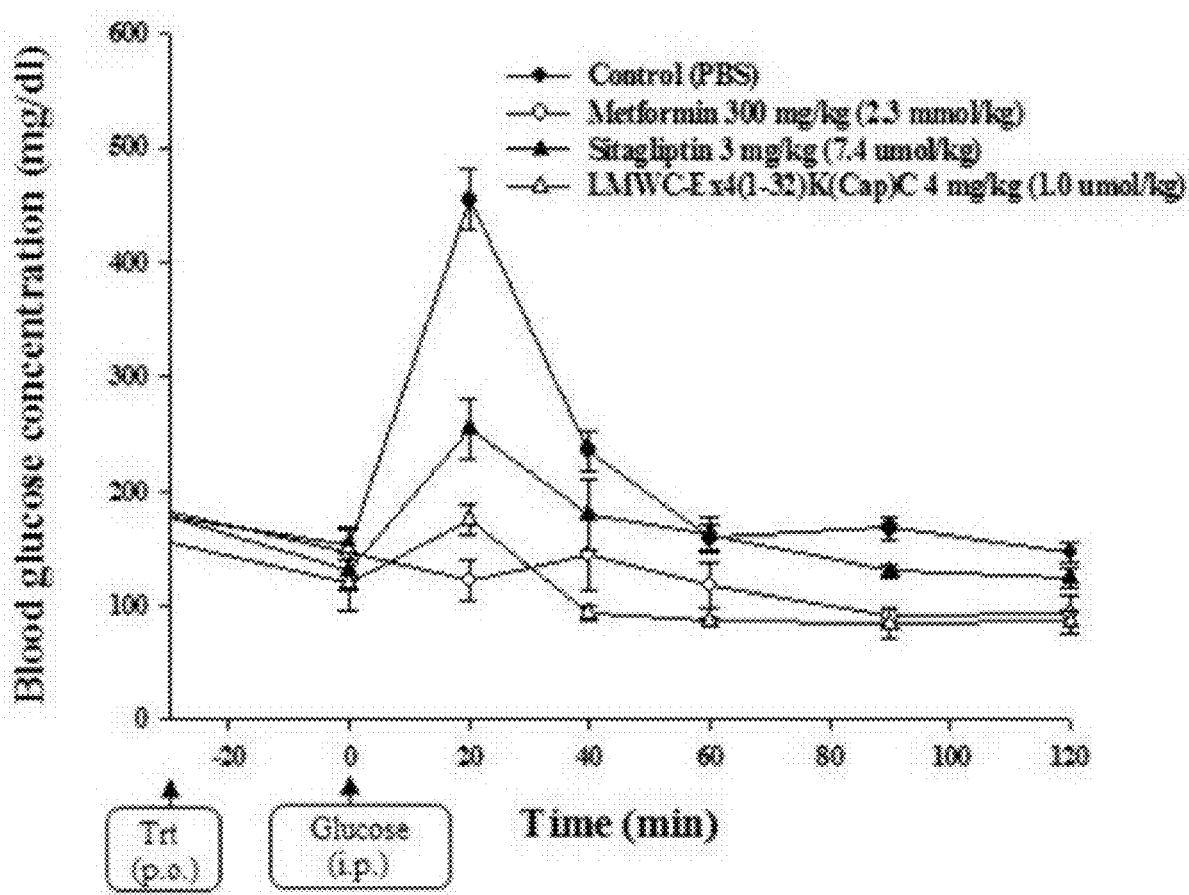
FIGS. 22a and 22b show glucose tolerance by oral administration of LMWC-Ex4(1-32)K(Cap) using diabetic model mice, compared with metformin and sitagliptin.
Figure 22B:
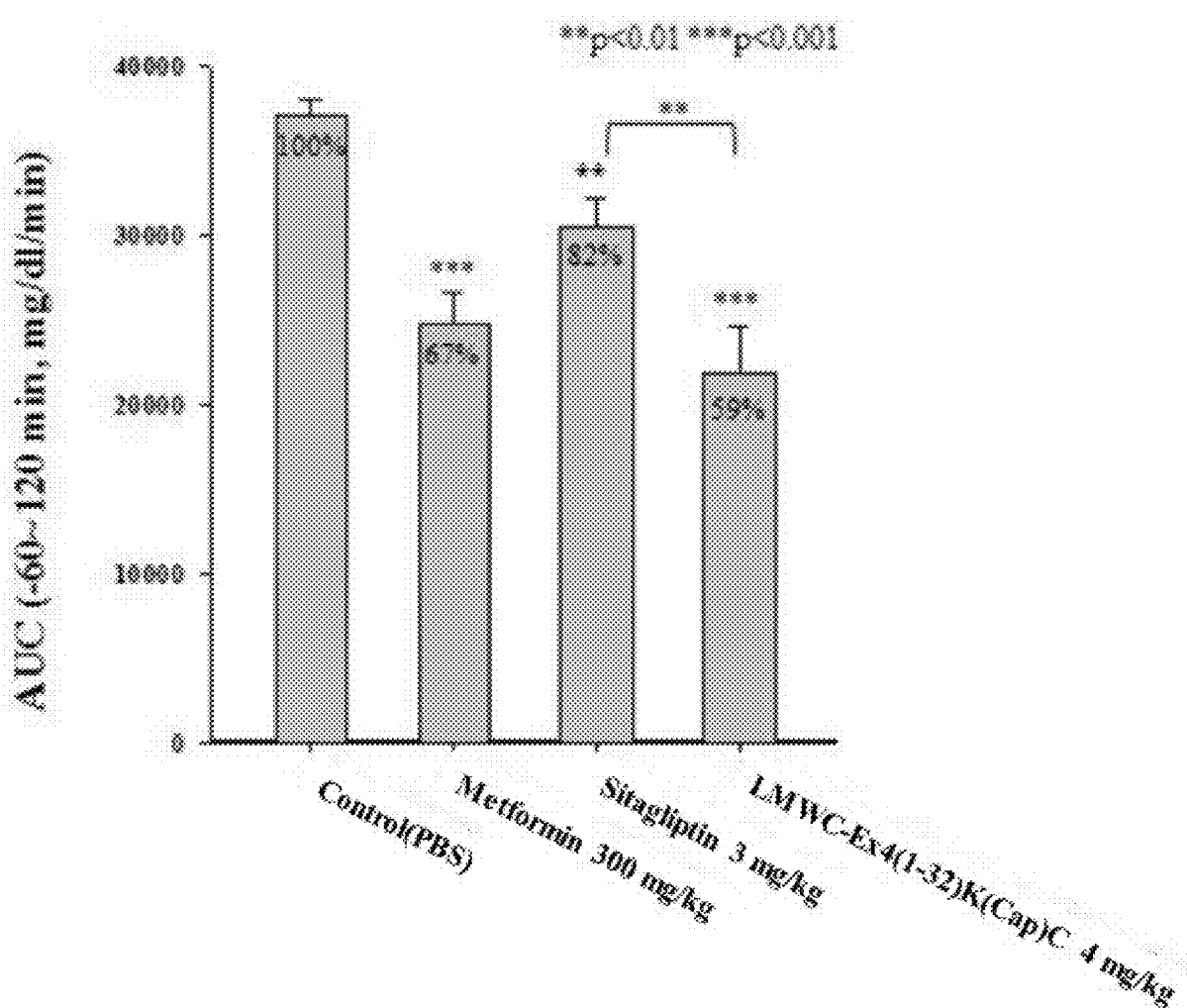

Comparative Test of (Oral) Effect of LMWC-Ex4(1-32)K(Cap) Conjugate Using Diabetic Model Mice For the comparison with metformin and sitagliptin as positive controls, the diabetic model mice fasted for 18 hours were (orally) administered with LMWC-Ex4(1-32)K(Cap)C, which was obtained by conjugating LMWC to Ex4(1-32)K(Cap), at a concentration of 4 mg/kg, and metformin at 300 mg/kg and sitagliptin at 3 mg/kg, and then, after 60 minutes, abdominally administered with glucose. After 0, 20, 40, 60, 90, 120, and 180 minutes, the blood was collected from the end of the tail of the mice to check the glucose tolerance ability. As a result, it was verified that LMWC-Ex4(1-32)K(Cap)C had significant glucose tolerance similar to that of metformin as a positive control, and more excellent that of sitagliptin as a positive control (FIGS. 22a and 22b).

Figure 23A:
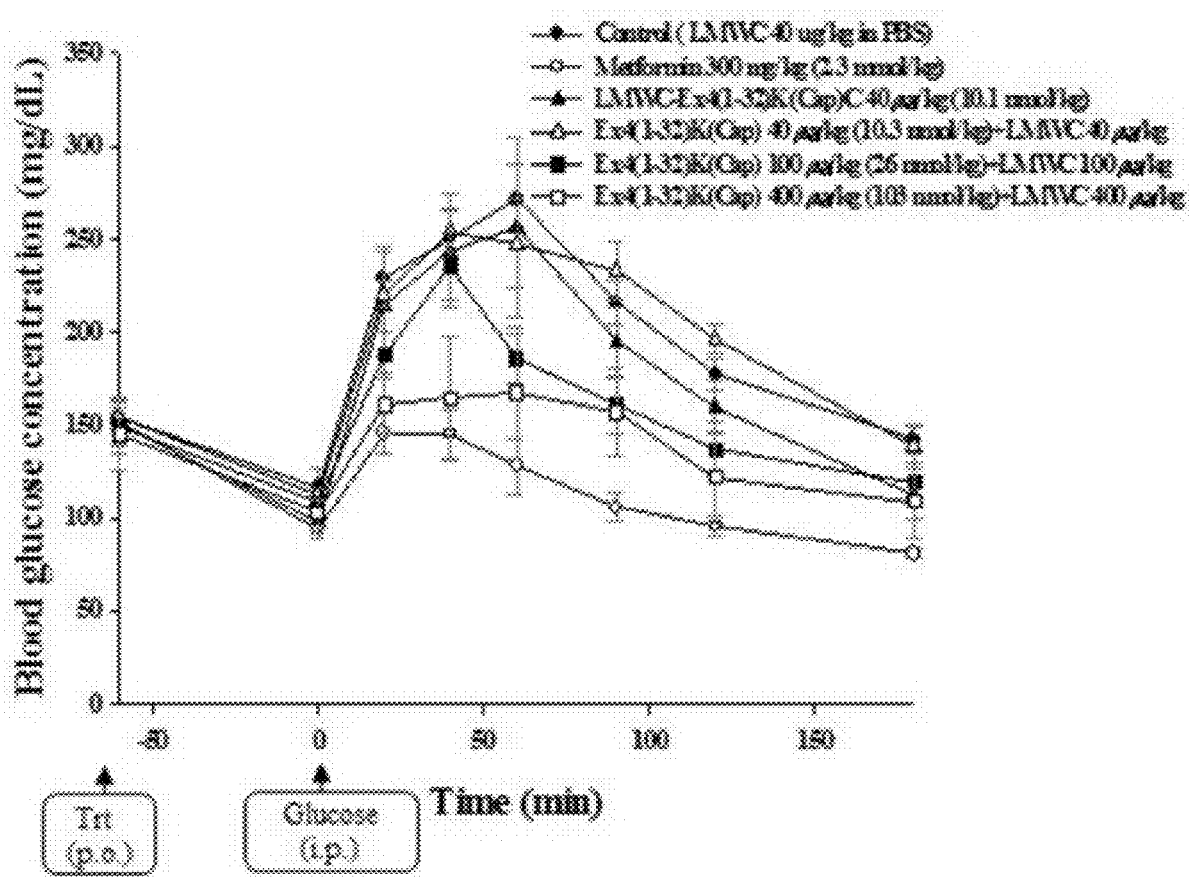
FIGS. 23a and 23b show blood glucose lowering effects by oral administration of LMWC-Ex4(1-32)K(Cap) or a mixture of Ex4(1-32)K(Cap) and LMWC using diabetic model mice, compared with metformin.
Figure 23B:
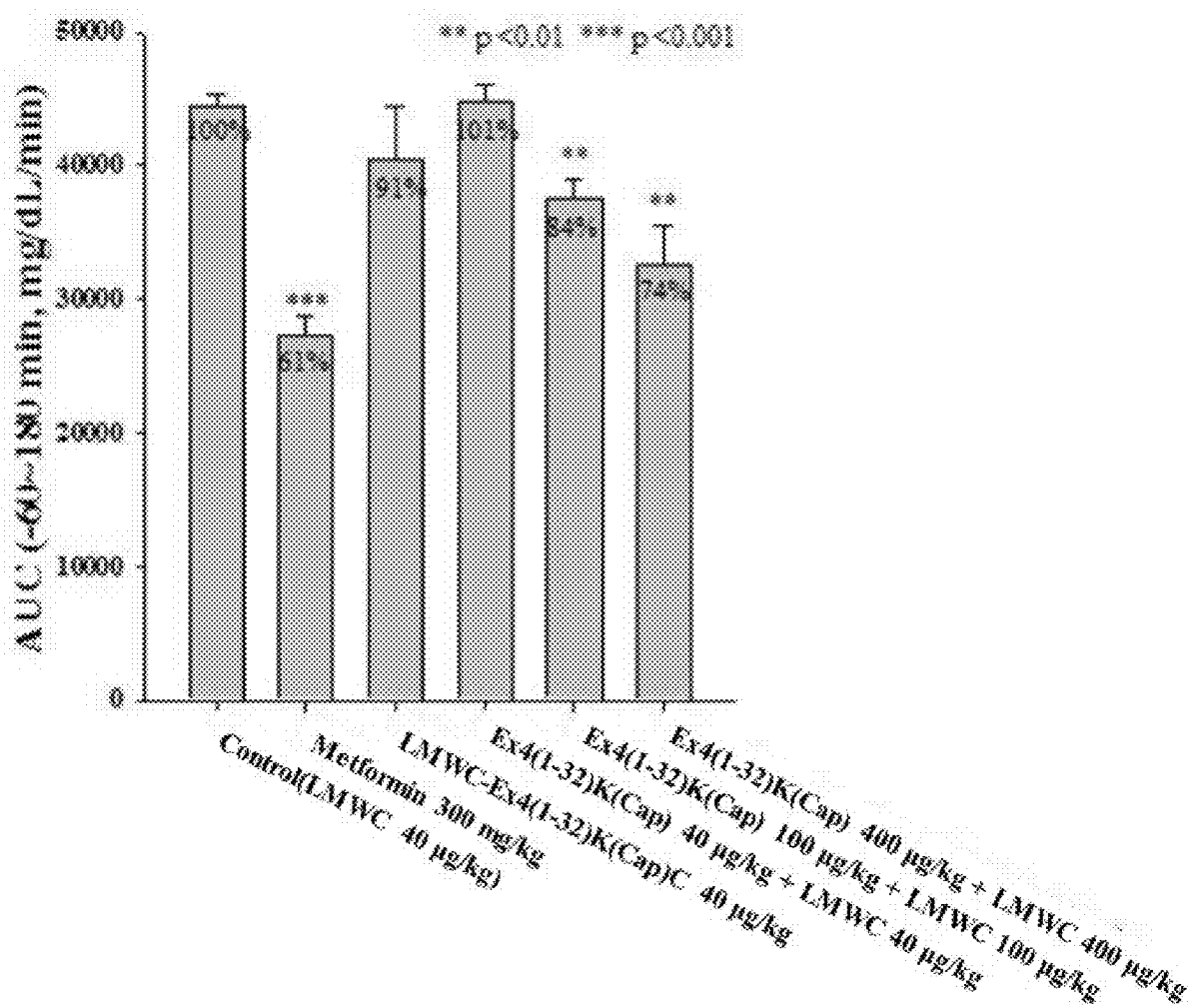

(Oral) Glucose Tolerance Test of Co-Administration of Ex4(1-32)K(Cap) and LMWC Using Diabetic Model Mice The db/db mice fasted for 18 hours were orally administered with a solution of the short exenatide-fatty acid conjugate Ex4(1-32)K(Cap) mixed with LMWC at the same doses of 40 µg/kg, 100 µg/kg, and 400 µg/kg, and then after 60 minutes, abdominally administered with glucose. After 0, 20, 40, 60, 90, 120, and 180 minutes, the glucose tolerance test of the drugs was carried out. As a result, it was verified that the co-administration of Ex4(1-32)K(Cap) and LMWC showed a concentration-dependent blood glucose lowering effect (FIGS. 23a and 23b).

Figure 24A:
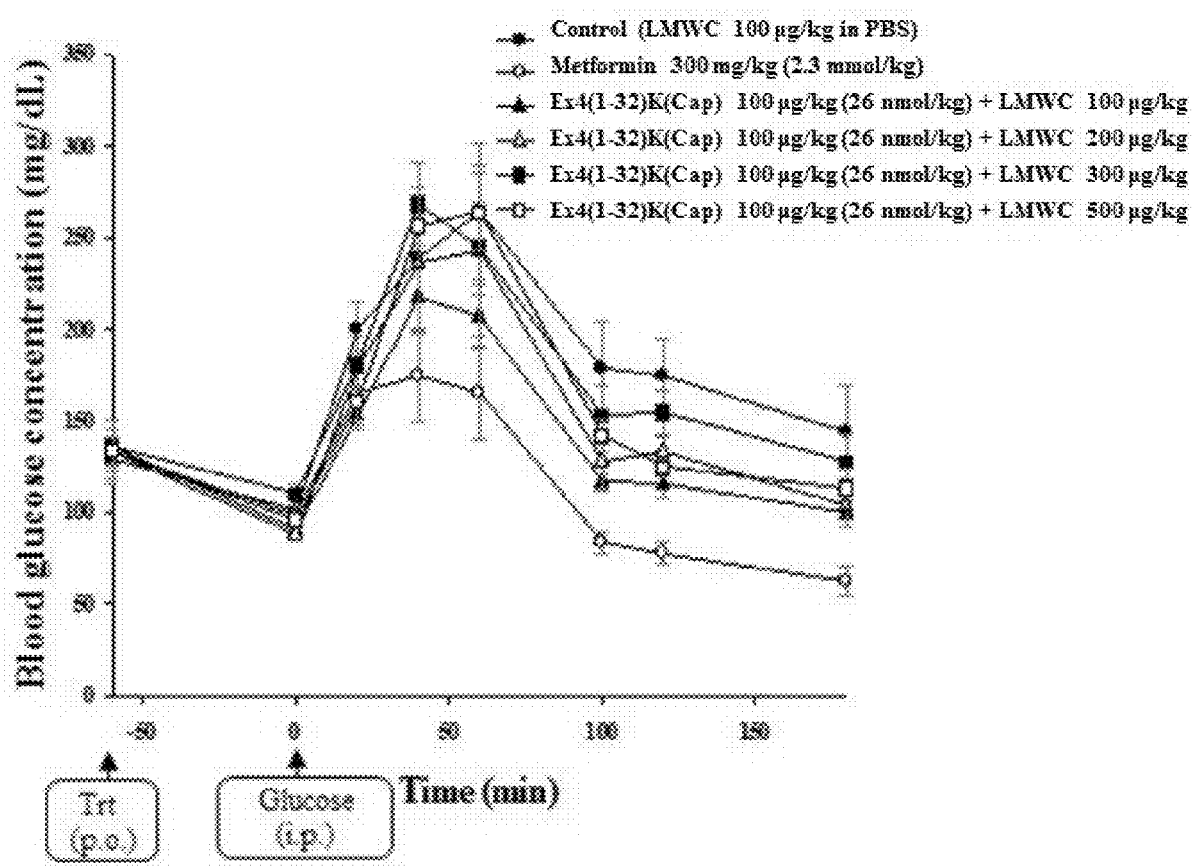
FIGS. 24a and 24b show blood glucose lowering effects by oral administration of Ex4(1-32)K(Cap) and LMWC (100 µg/kg, 200 µg/kg, 300 µg/kg, or 500 µg/kg) in mixture using diabetic model mice.
Figure 24B:
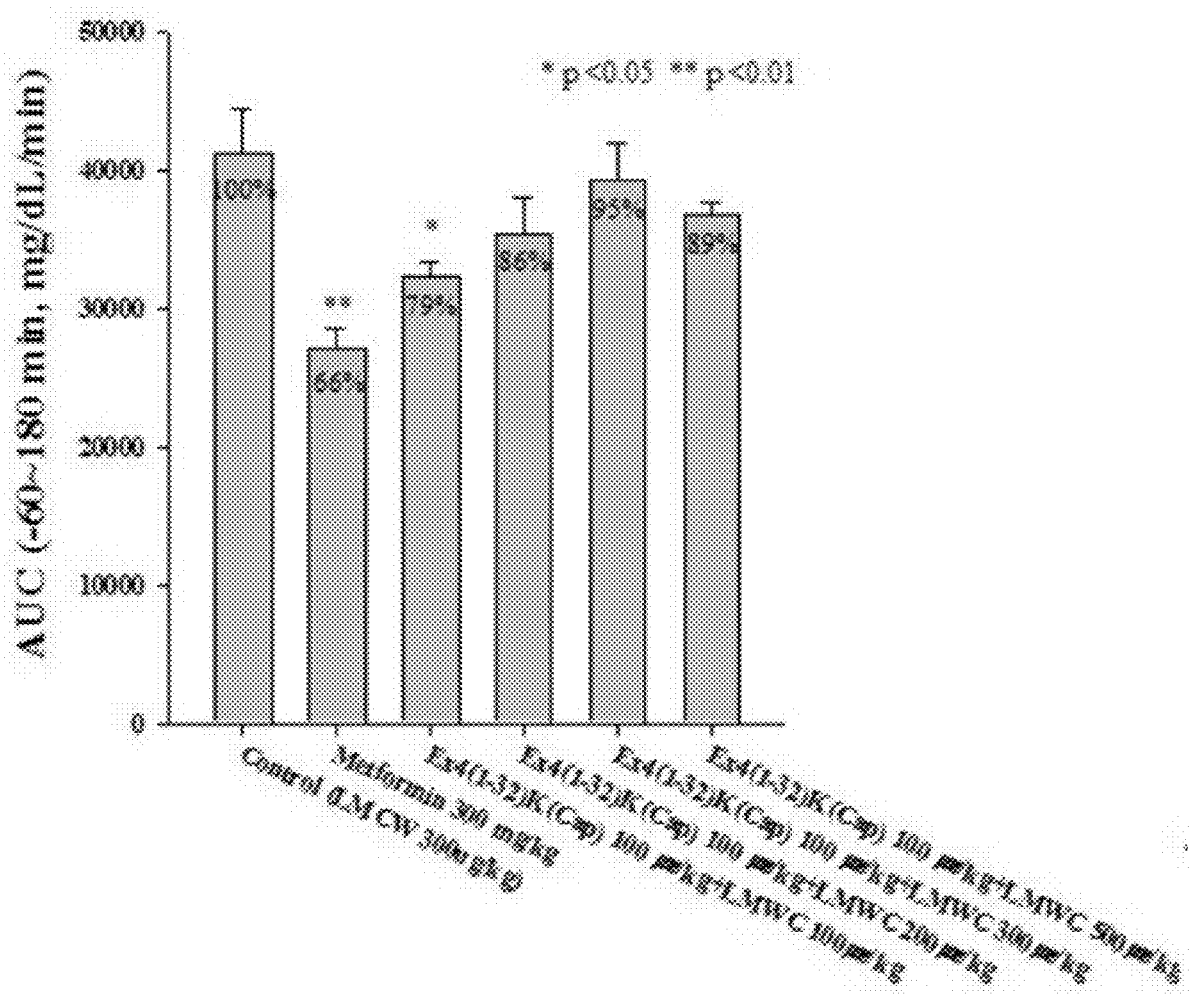

Comparative Test of (Oral) Effect of Co-Administration of Ex4(1-32)K(Cap) and LMWC Using Diabetic Model Mice In order to investigate the effect according to the amount of LMWC mixed in the (oral) administration of the short exenatide-fatty acid conjugate Ex4(1-32)K(Cap), the db/db mice fasted for 18 hours were orally administered with 100 µg/kg of Ex4(1-32)K(Cap) mixed with LMWC at doses of 100 µg/kg, 200 µg/kg, 300 µg/kg, and 500 µg/kg, and then after 60 minutes, abdominally administered with glucose. After 0, 20, 40, 60, 100, 120, and 180 minutes, the glucose tolerance test of the drugs was carried out. As a result, it was verified that the co-administration of Ex4(1-32)K(Cap) and LMWC showed a blood glucose lowering effect at a low dose of 100 µg/kg in the dose range of 100-500 µg/kg (FIGS. 24a and 24b).

Figure 25A:
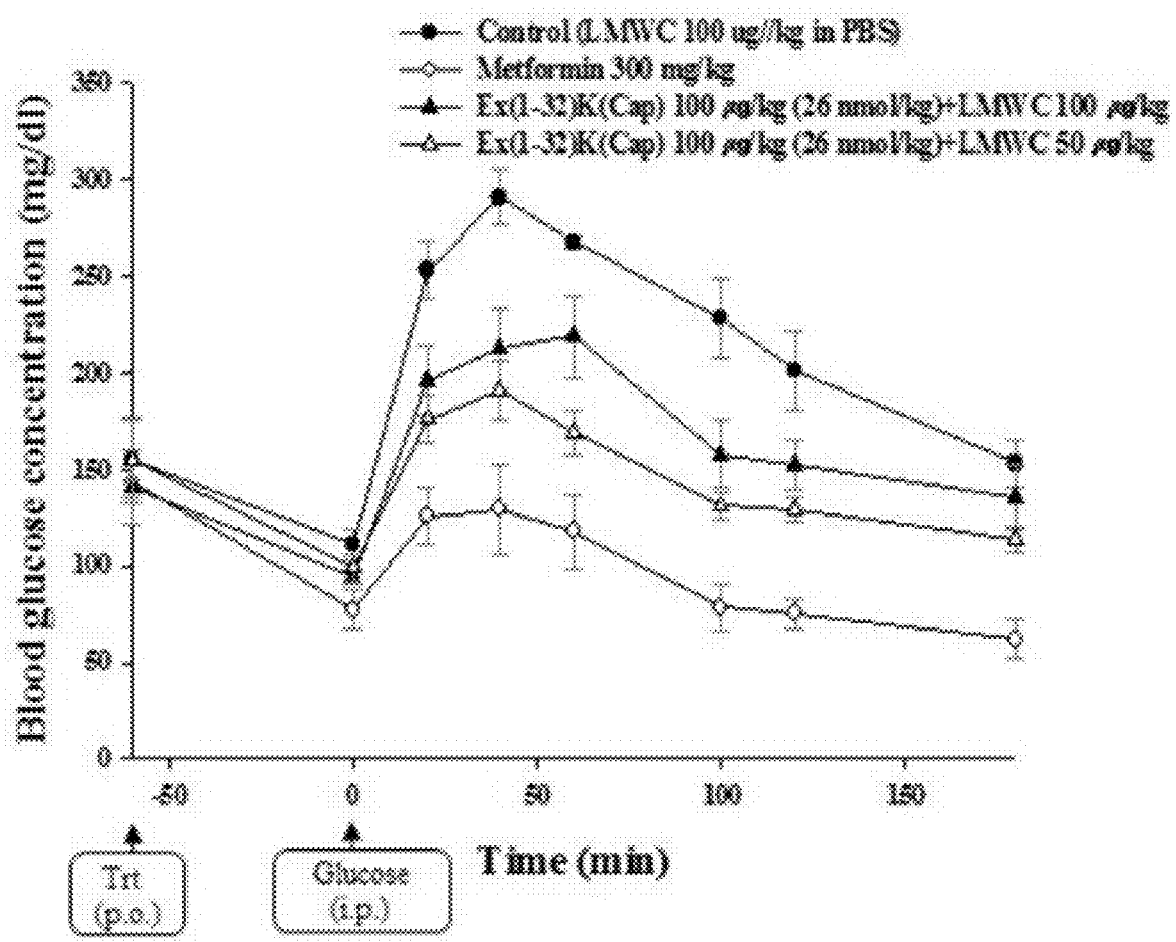
FIGS. 25a and 25b show blood glucose lowering effects by oral administration of Ex4(1-32)K(Cap) and LMWC (100 µg/kg or 50 µg/kg) in mixture using diabetic model mice.
Figure 25B:
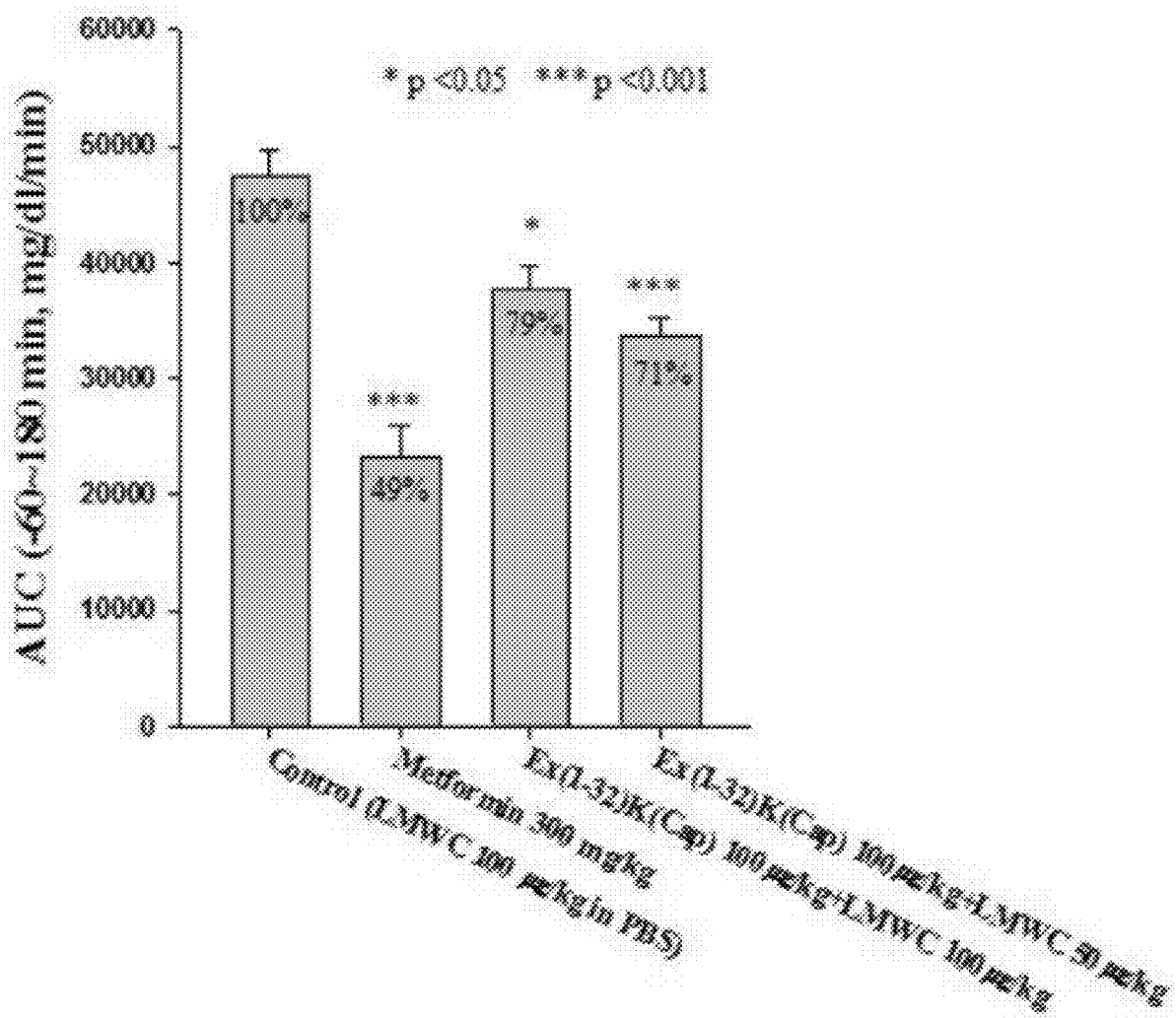

The db/db mice fasted for 18 hours were orally administered with Ex4(1-32)K(Cap) 100 µg/kg mixed LMWC at doses of 100 µg/kg and 50 µg/kg, and then after 60 minutes, abdominally administered with glucose. After 0, 20, 40, 60, 100, 120, and 180 minutes, the glucose tolerance test was carried out. As a result, it was verified that the co-administration of Ex4(1-32)K(Cap) and LMWC showed an additional blood glucose lowering effect in LMWC 50 µg/kg rather than LMWC 100 µg/kg (FIGS. 25a and 25b).

Figure 26A:
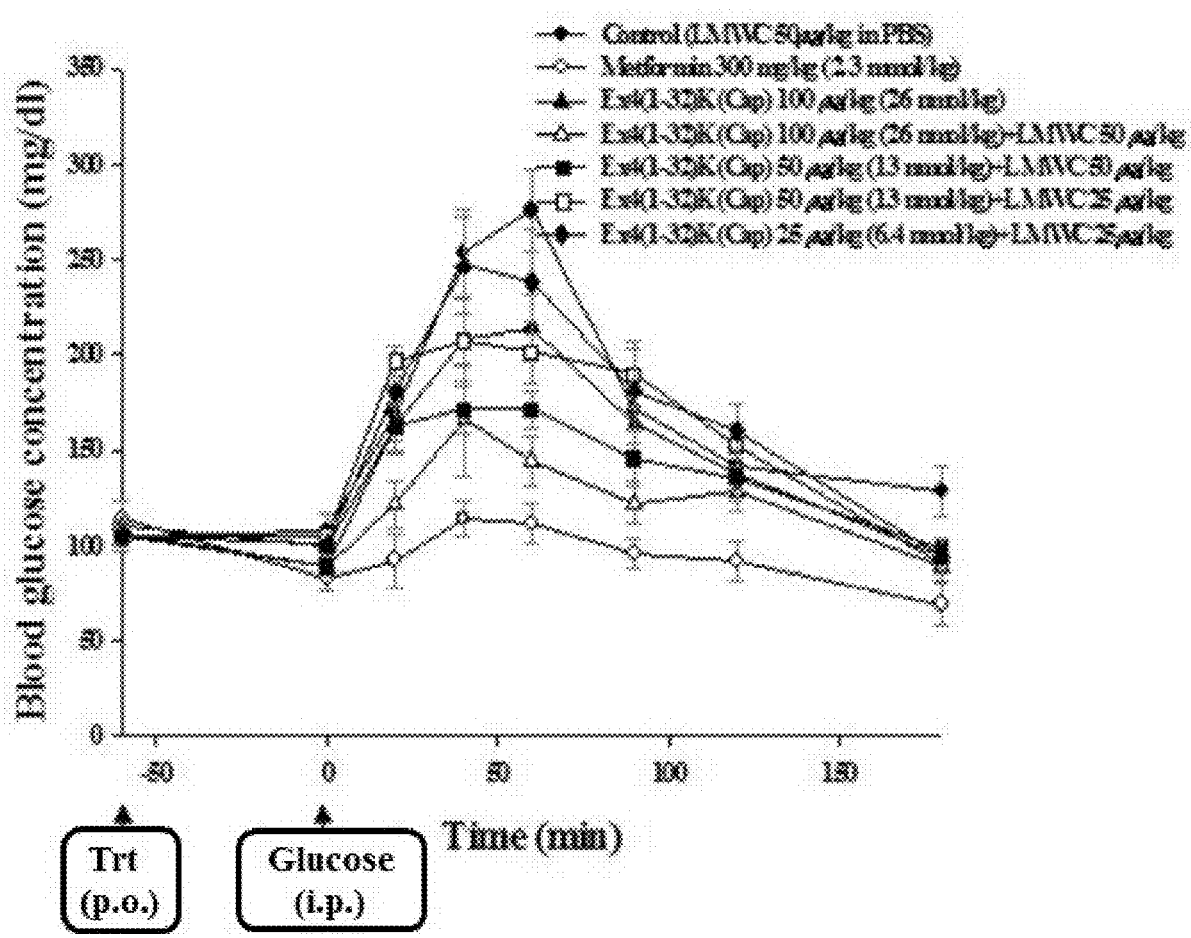
FIGS. 26a and 26b show glucose tolerance by oral administration of Ex4(1-32)K(Cap) (100 µg/kg) alone, and Ex4(1-32)K(Cap)(25, 50, or 100 µg/kg) and LMWC (50 µg/kg or 100 µg/kg) in mixture using diabetic model mice.
Figure 26B:
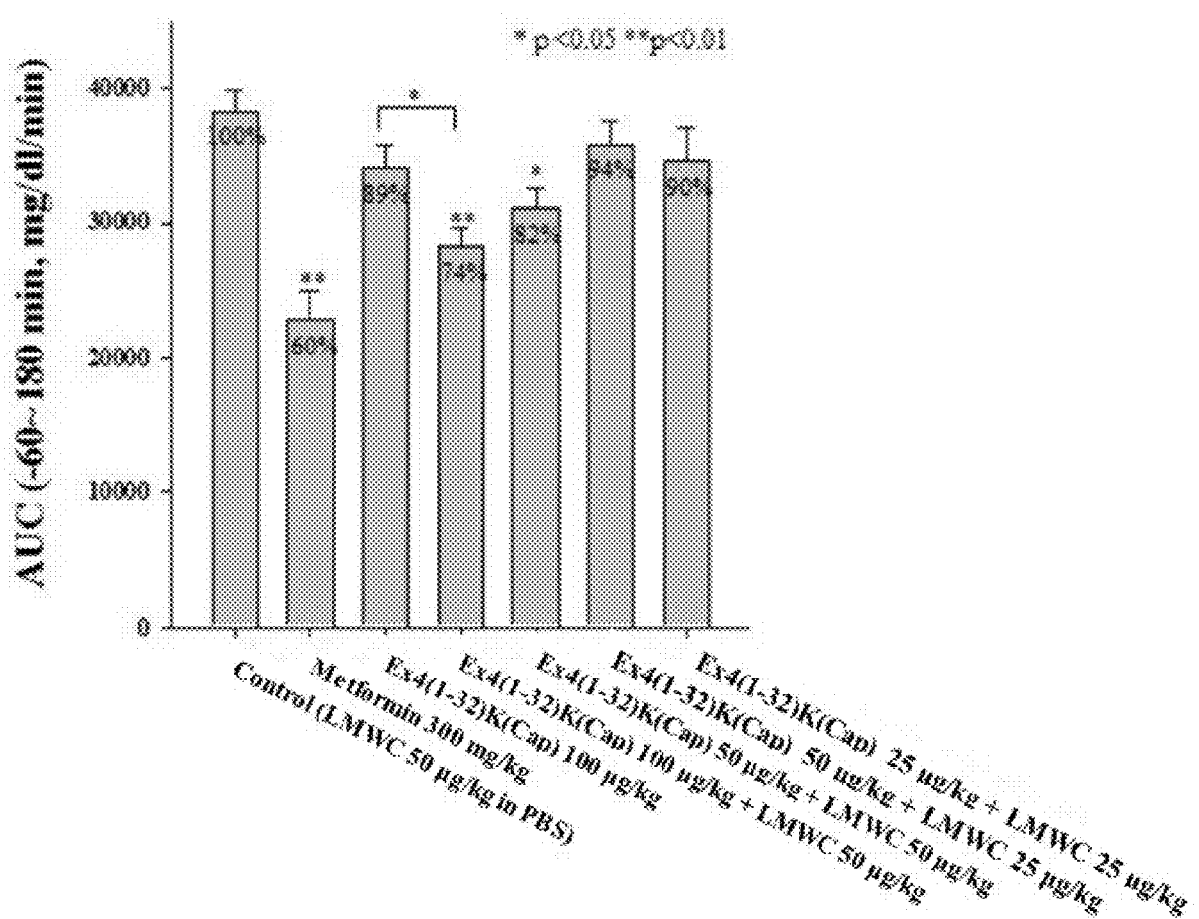

For the comparison between single administration of Ex4(1-32)K(Cap) 100 µg/kg and oral administration of the mixture with LMWC, the fasted diabetic model mice were orally administered with Ex4(1-32)K(Cap) 100 µg/kg, and Ex4(1-32)K(Cap) 25 µg/kg, 50 µg/kg, and 100 µg/kg plus LMWC 25 µg/kg and 50 µg/kg for each, and then after 60 minutes, abdominally administered with glucose. After 0, 20, 40, 60, 90, 120, and 180 minutes, the glucose tolerance test of the drugs was carried out. As a result, it was verified that the oral administration of the mixture of Ex4(1-32)K(Cap) 100 µg/kg and LMWC 50 µg/kg had a significant glucose tolerance, which was more excellent compared with the single administration of Ex4(1-32)K(Cap) 100 µg/kg, and for the additional blood glucose lowering effect at the time of (oral) administration of Ex4(1-32)K(Cap) to the fasted diabetic mice, the dose of LMWC mixed was required at minimum 50 µg/kg (FIGS. 26a and 26b).

Figure 27A:
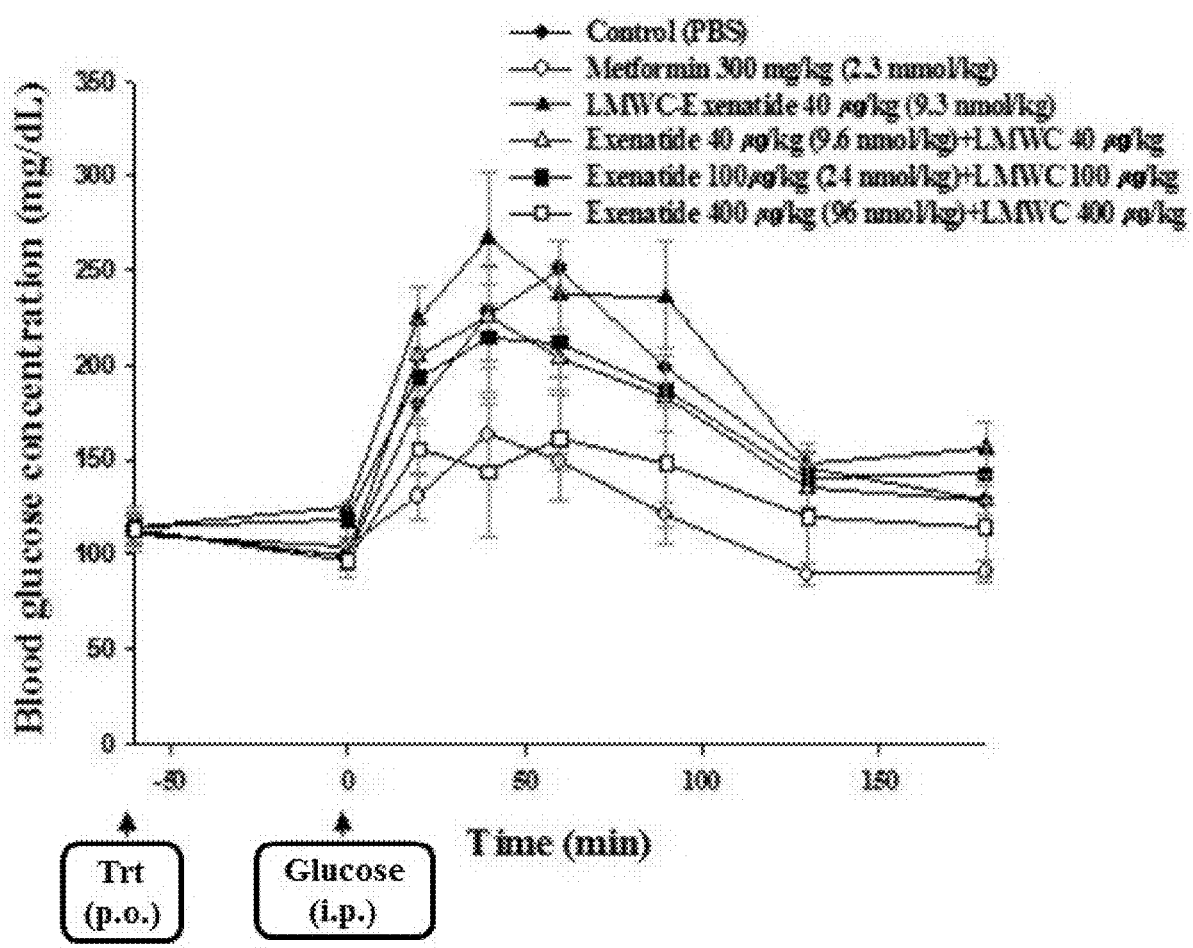
FIGS. 27a and 27b show blood glucose lowering effects by oral administration of exenatide mixed with LMWC at 40, 100, or 400 µg/kg for each using diabetic model mice.
Figure 27B:
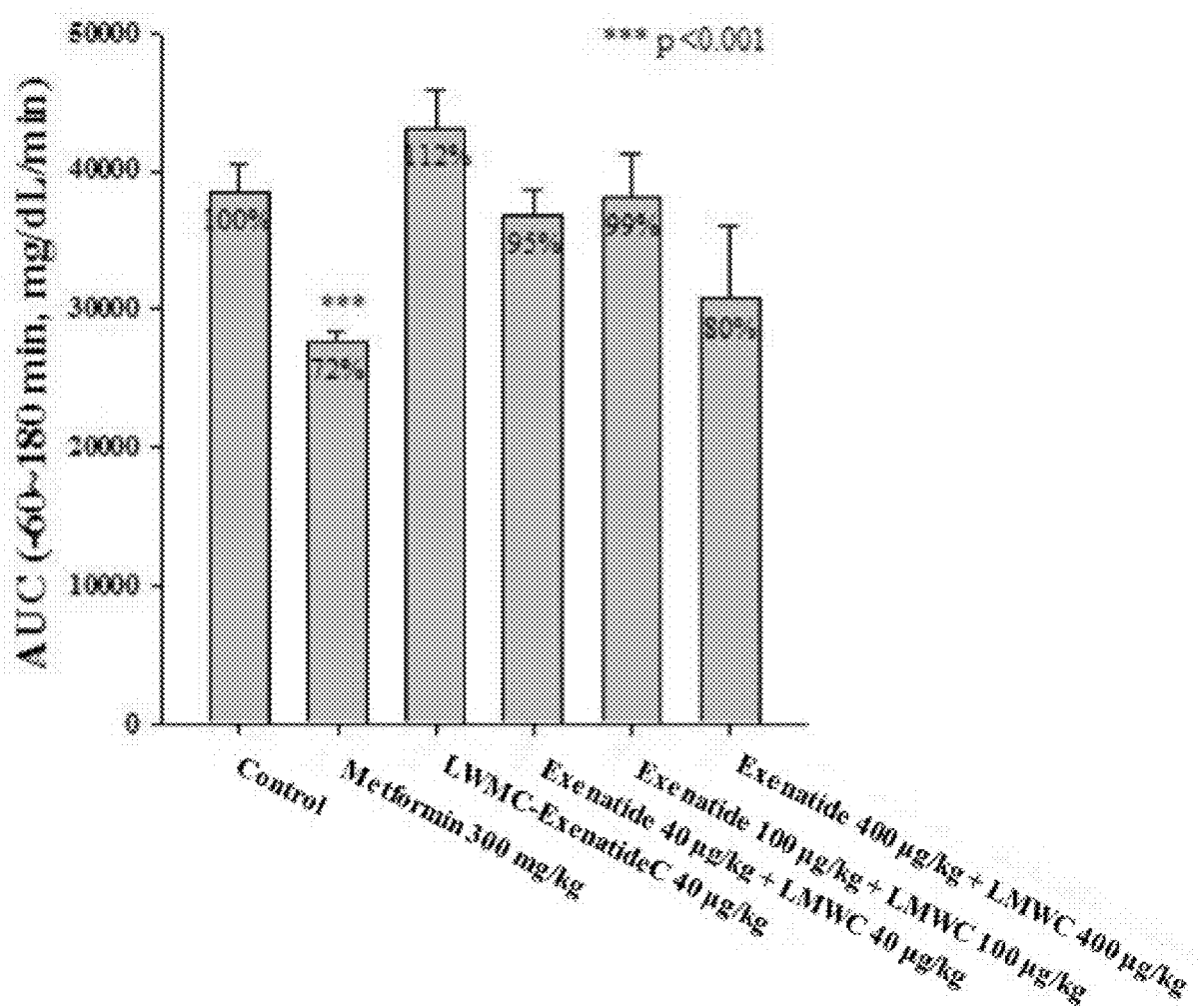

(Oral) Glucose Tolerance Test of Co-Administration of Exenatide and LMWC Using Diabetic Model Mice Mixture solutions of exenatide and LMWC mixed at the same doses of 40 µg/kg, 100 µg/kg, and 400 µg/kg were orally administered, and then after 60 minutes, glucose was abdominally administered. After 0, 20, 40, 60, 90, 120, and 180 minutes, the glucose tolerance test of the drugs was carried out. As a result, it was verified that the co-administration of exenatide and LMWC had a concentration-dependent blood glucose lowering effect (FIGS. 27a and 27b).

Figure 28A:
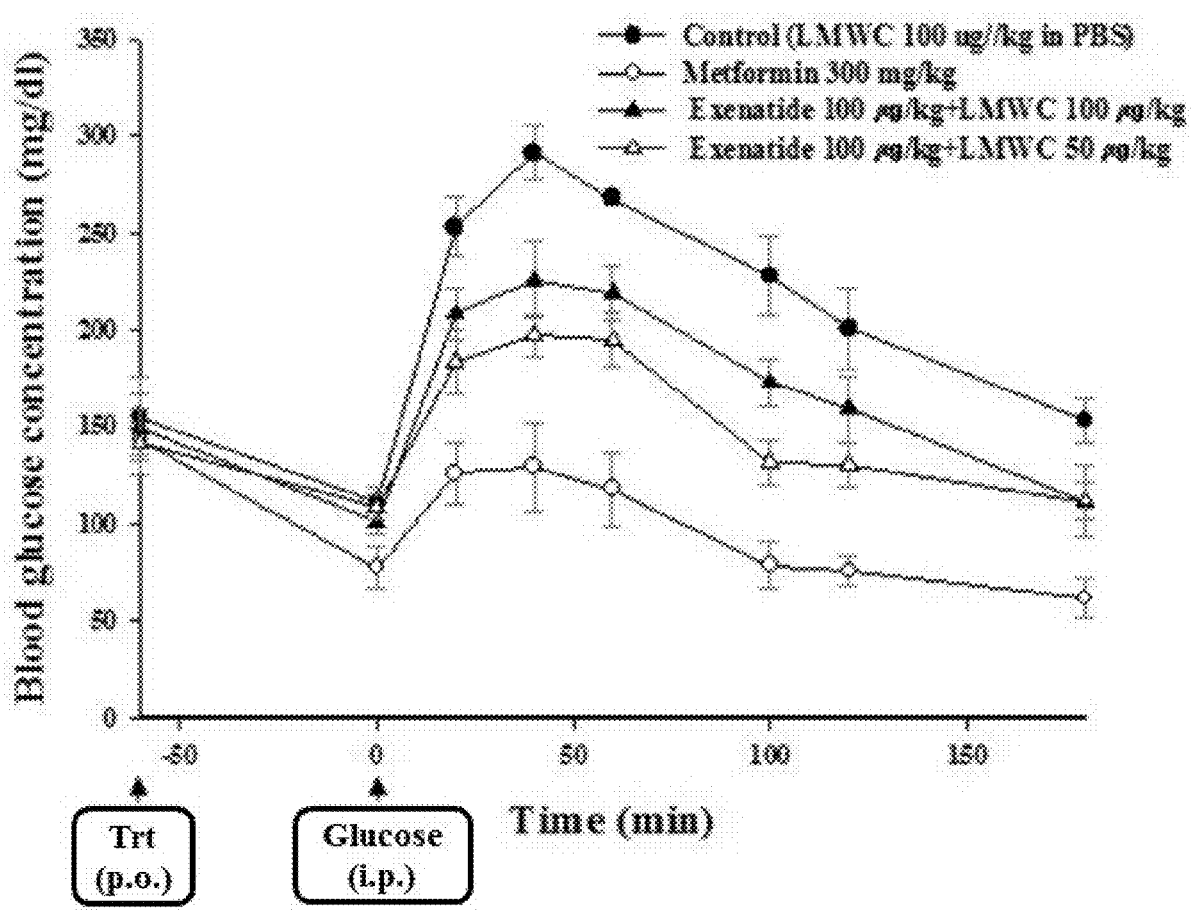
FIGS. 28a and 28b show blood glucose lowering effects by oral administration of exenatide (100 µg/kg) mixed with LMWC (50 µg/kg or 100 µg/kg) using diabetic model mice.
Figure 28B:
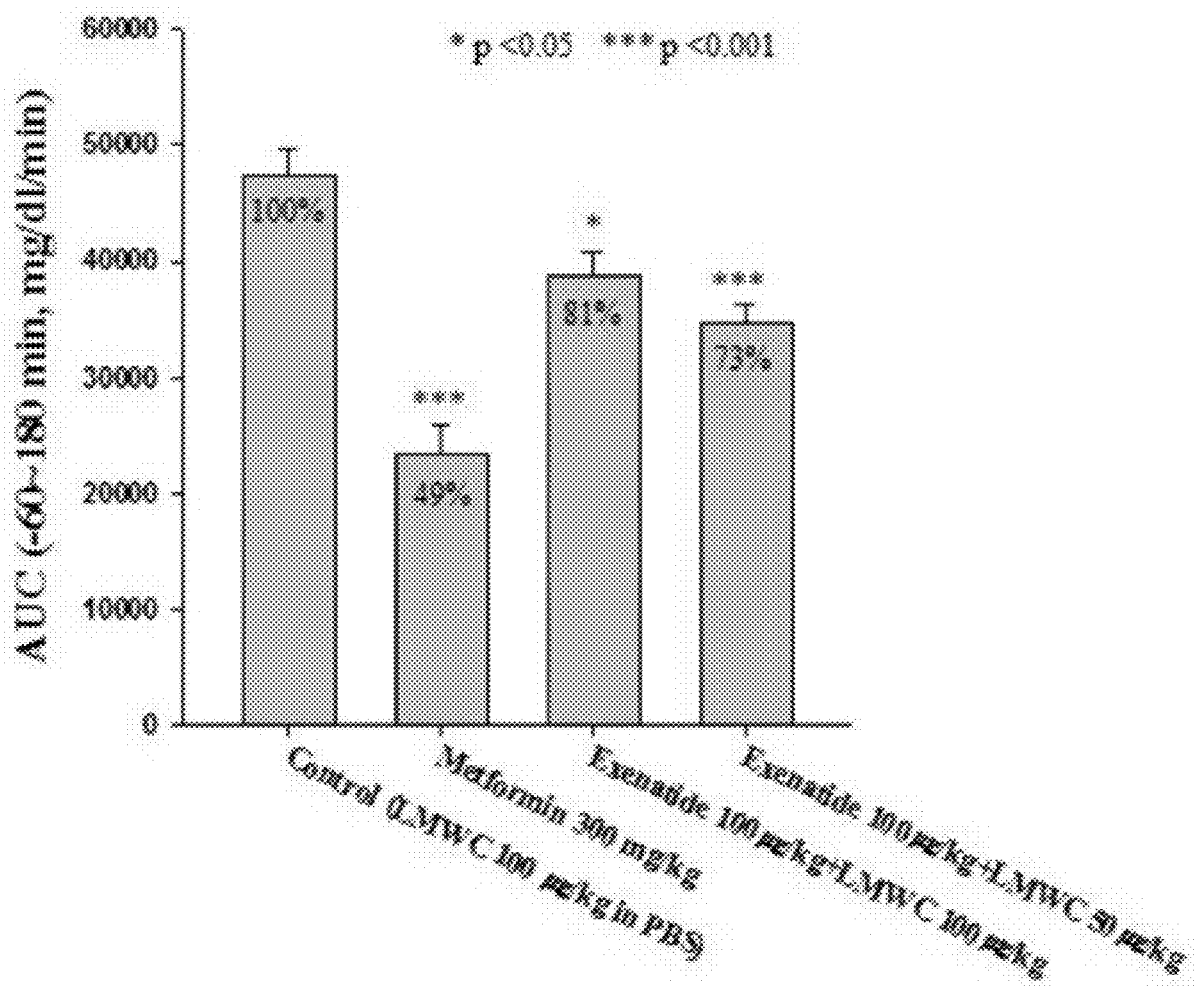

Comparative Test of (Oral) Effect of Co-Administration of Exenatide and LMWC Using Diabetic Model Mice The diabetic model mice fasted for 18 hours were orally administered with mixture solutions of exenatide 100 μg/kg mixed with LMWC at doses of 100 μg/kg and 50 μg/kg, and then after 60 minutes, glucose was abdominally administered. After 0, 20, 40, 90, 120, and 180 minutes, the glucose tolerance test of the drugs was carried out. As a result, it was verified that the co-administration of exenatide and LMWC showed an additional blood glucose lowering effect in LMWC 50 μg/kg rather than LMWC 100 μg/kg (FIGS. 28a and 28b).

Figure 29A:
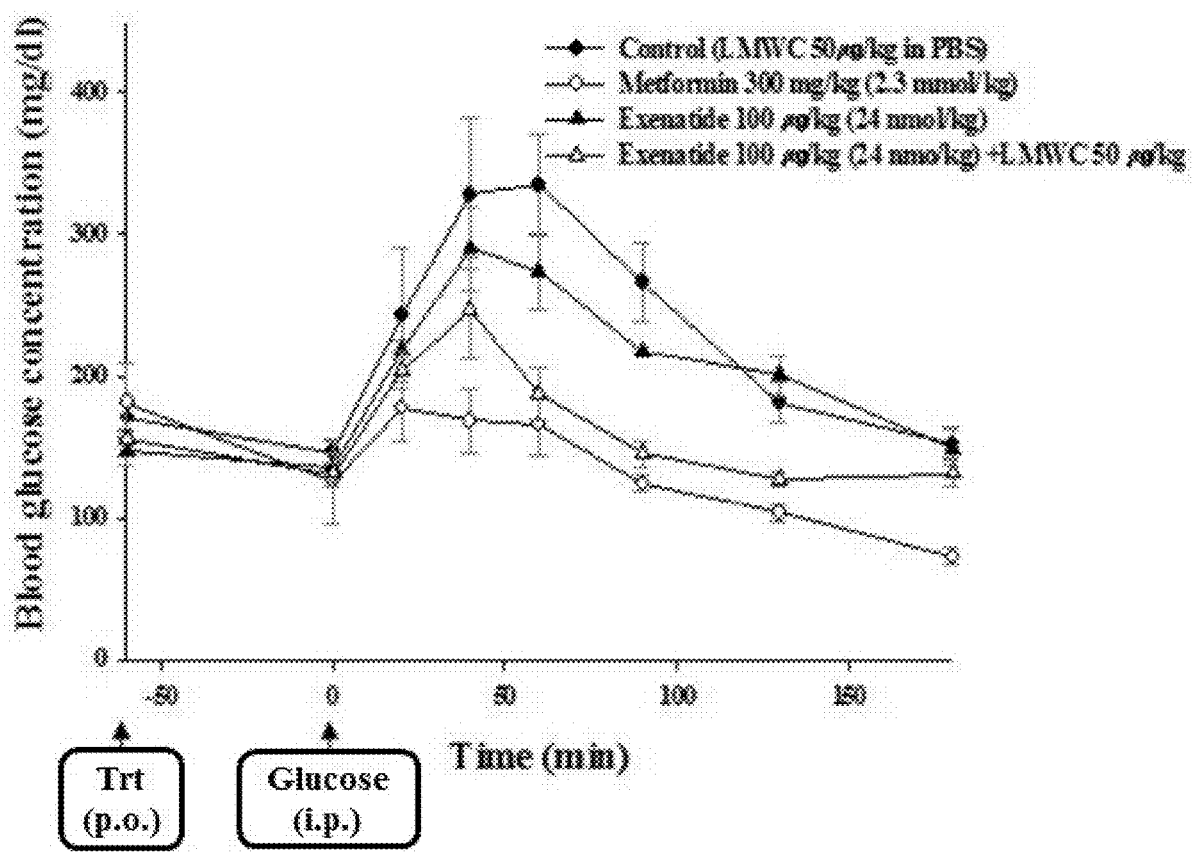
FIGS. 29a and 29b show blood glucose lowering effects by oral administration of exenatide (100 µg/kg) alone, and exenatide mixed with LMWC (50 µg/kg) in mixture using diabetic model mice.
Figure 29B:
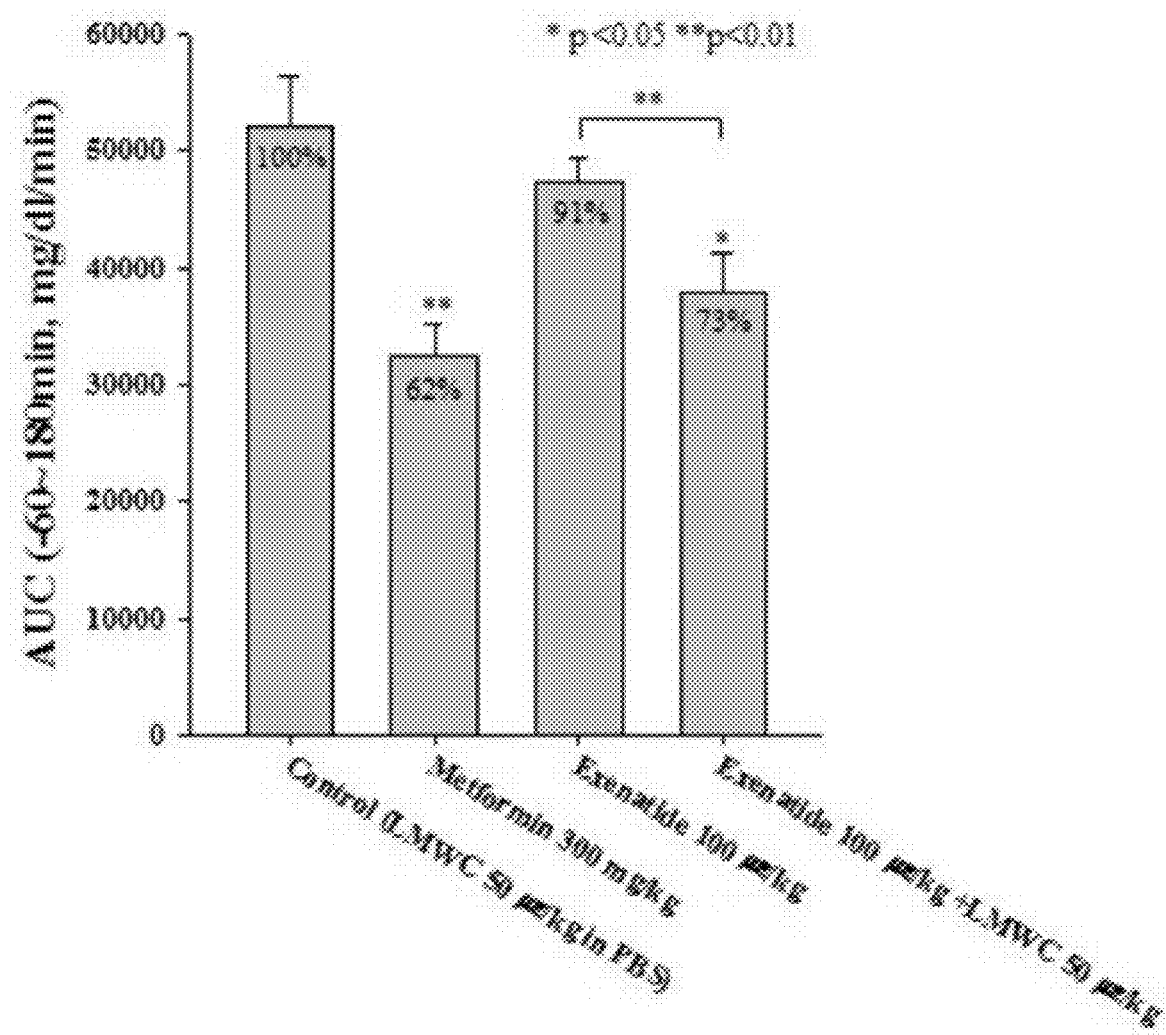

For the comparison between single administration of exenatide 100 μg/kg and oral administration of the mixture with LMWC, the diabetic model mice fasted for 18 hours were (orally) administered with exenatide 100 μg/kg, and a mixture solution of exenatide 100 μg/kg mixed with LMWC 50 μg/kg, and then after 60 minutes, abdominally administered with glucose. After 0, 20, 40, 60, 90, 120, and 180 minutes, the glucose tolerance test of the drugs was carried out. As a result, it was verified that the (oral) co-administration of exenatide 100 μg/kg and LMWC 50 μg/kg had significant glucose tolerance, which was more excellent compared with the single administration of exenatide 100 μg/kg (FIGS. 29a and 29b).

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. An exenatide analog comprising 7 to 9 amino acid deletions in the C-terminal of the amino acid sequence of exenatide and a fatty acid conjugated thereto,
    wherein the amino acid sequence of the exenatide is SEQ ID NO: 1,
    wherein the fatty acid is conjugated to the C-terminal of the amino acid-deleted exenatide via a lysine linker,
    wherein the fatty acid is selected from the group consisting of valeric acid, caprylic acid, and capric acid.

2. A composition comprising:
    (a) the exenatide analog of claim 1; and
    (b) an acceptable carrier.

3. A method for alleviating or treating diabetes comprising:
    administering to a subject a pharmaceutical composition comprising, as an active ingredient, an exenatide analog comprising exenatide having 7 to 9 amino acid deletions in the C-terminal of the amino acid sequence of exenatide and a fatty acid conjugated thereto,
    wherein the amino acid sequence of the exenatide is SEQ ID NO: 1,
    wherein the fatty acid is conjugated to the C-terminal of the amino acid-deleted exenatide via a lysine linker,
    wherein the fatty acid is selected from the group consisting of valeric acid, caprylic acid, and capric acid.

4. A method for suppressing appetite, comprising:
    administering to a subject a pharmaceutical composition containing, as an active ingredient, an exenatide analog comprising exenatide having 7 to 9 amino acid deletions in the C-terminal of the amino acid sequence of exenatide and a fatty acid conjugated thereto,
    wherein the amino acid sequence of the exenatide is SEQ ID NO: 1,
    wherein the fatty acid is conjugated to the C-terminal of the amino acid-deleted exenatide via a lysine linker,
    wherein the fatty acid is selected from the group consisting of valeric acid, caprylic acid, and capric acid.

* * * * *

```
                        SEQUENCE LISTING

<160> NUMBER OF SEQ ID NOS: 29

<210> SEQ ID NO 1
    <211> LENGTH: 39
    <212> TYPE: PRT
    <213> ORGANISM: Artificial Sequence
    <220> FEATURE:
    <223> OTHER INFORMATION: Exenatide

<400> SEQUENCE: 1

His Gly Glu Gly Thr Phe Thr Ser Asp Leu Ser Lys Gln Met Glu Glu
    1               5                   10                  15

Glu Ala Val Arg Leu Phe Ile Glu Trp Leu Lys Asn Gly Gly Pro Ser
                20                  25                  30

Ser Gly Ala Pro Pro Pro Ser
            35

<210> SEQ ID NO 2
    <211> LENGTH: 30
    <212> TYPE: PRT
    <213> ORGANISM: Artificial Sequence
    <220> FEATURE:
    <223> OTHER INFORMATION: GLP-1

<400> SEQUENCE: 2

His Ala Glu Gly Thr Phe Thr Ser Asp Val Ser Ser Tyr Leu Glu Gly
    1               5                   10                  15

Gln Ala Ala Lys Glu Phe Ile Ala Trp Leu Val Lys Gly Arg
                20                  25                  30

<210> SEQ ID NO 3
    <211> LENGTH: 29
    <212> TYPE: PRT
    <213> ORGANISM: Artificial Sequence
    <220> FEATURE:
    <223> OTHER INFORMATION: Ex4 (1-29)

<400> SEQUENCE: 3

His Gly Glu Gly Thr Phe Thr Ser Asp Leu Ser Lys Gln Met Glu Glu
    1               5                   10                  15

Glu Ala Val Arg Leu Phe Ile Glu Trp Leu Lys Asn Gly
                20                  25
```

```
<210> SEQ ID NO 4
<211> LENGTH: 30
<212> TYPE: PRT
<213> ORGANISM: Artificial Sequence
<220> FEATURE:
<223> OTHER INFORMATION: Ex4 (1-30)

<400> SEQUENCE: 4

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly
            20                  25                  30

<210> SEQ ID NO 5
<211> LENGTH: 31
<212> TYPE: PRT
<213> ORGANISM: Artificial Sequence
<220> FEATURE:
<223> OTHER INFORMATION: Ex4 (1-31)

<400> SEQUENCE: 5

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro
            20                  25                  30

<210> SEQ ID NO 6
<211> LENGTH: 32
<212> TYPE: PRT
<213> ORGANISM: Artificial Sequence
<220> FEATURE:
<223> OTHER INFORMATION: Ex4 (1-32)

<400> SEQUENCE: 6

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

<210> SEQ ID NO 7
<211> LENGTH: 33
<212> TYPE: PRT
<213> ORGANISM: Artificial Sequence
<220> FEATURE:
<223> OTHER INFORMATION: Ex4 (1-33)

<400> SEQUENCE: 7

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser

<210> SEQ ID NO 8
<211> LENGTH: 35
<212> TYPE: PRT
<213> ORGANISM: Artificial Sequence
<220> FEATURE:
<223> OTHER INFORMATION: Ex4 (1-35)

<400> SEQUENCE: 8

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
```

Ser Gly Ala
    35

<210> SEQ ID NO 9
<211> LENGTH: 31
<212> TYPE: PRT
<213> ORGANISM: Artificial Sequence
<220> FEATURE:
<223> OTHER INFORMATION: Ex4 (1-30)K(Val)
<220> FEATURE:
<221> NAME/KEY: MISC_FEATURE
<222> LOCATION: (31)..(31)
<223> OTHER INFORMATION: Valeric Acid conjugation

<400> SEQUENCE: 9

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Lys
            20                  25                  30

<210> SEQ ID NO 10
<211> LENGTH: 31
<212> TYPE: PRT
<213> ORGANISM: Artificial Sequence
<220> FEATURE:
<223> OTHER INFORMATION: Ex4 (1-30)K(Cpr)
<220> FEATURE:
<221> NAME/KEY: MISC_FEATURE
<222> LOCATION: (31)..(31)
<223> OTHER INFORMATION: Caprylic acid conjugation

<400> SEQUENCE: 10

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Lys
            20                  25                  30

<210> SEQ ID NO 11
<211> LENGTH: 31
<212> TYPE: PRT
<213> ORGANISM: Artificial Sequence
<220> FEATURE:
<223> OTHER INFORMATION: Ex4 (1-30)K(Cap)
<220> FEATURE:
<221> NAME/KEY: MISC_FEATURE
<222> LOCATION: (31)..(31)
<223> OTHER INFORMATION: Capric acid conjugation

<400> SEQUENCE: 11

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Lys
            20                  25                  30

<210> SEQ ID NO 12
<211> LENGTH: 31
<212> TYPE: PRT
<213> ORGANISM: Artificial Sequence
<220> FEATURE:
<223> OTHER INFORMATION: Ex4(1-30)K(Lau)
<220> FEATURE:
<221> NAME/KEY: MISC_FEATURE
<222> LOCATION: (31)..(31)
<223> OTHER INFORMATION: Lauric acid conjugation

<400> SEQUENCE: 12

His Gly Glu Gly Thr Phe Thr Ser Asp Leu Ser Lys Gln Met Glu
1               5                   10                  15

Glu Ala Val Arg Leu Phe Ile Glu Trp Leu Lys Asn Gly Gly Lys
            20                  25                  30

<210> SEQ ID NO 13
<211> LENGTH: 31
<212> TYPE: PRT
<213> ORGANISM: Artificial Sequence
<220> FEATURE:
<223> OTHER INFORMATION: Ex4(1-30)K(Myr)
<220> FEATURE:
<221> NAME/KEY: MISC_FEATURE
<222> LOCATION: (31)..(31)
<223> OTHER INFORMATION: Myristic acid conjugate

<400> SEQUENCE: 13

His Gly Glu Gly Thr Phe Thr Ser Asp Leu Ser Lys Gln Met Glu
1               5                   10                  15

Glu Ala Val Arg Leu Phe Ile Glu Trp Leu Lys Asn Gly Gly Lys
            20                  25                  30

<210> SEQ ID NO 14
<211> LENGTH: 31
<212> TYPE: PRT
<213> ORGANISM: Artificial Sequence
<220> FEATURE:
<223> OTHER INFORMATION: Ex4(1-30)K(Pal)
<220> FEATURE:
<221> NAME/KEY: MISC_FEATURE
<222> LOCATION: (31)..(31)
<223> OTHER INFORMATION: Palmitic acid conjugate

<400> SEQUENCE: 14

His Gly Glu Gly Thr Phe Thr Ser Asp Leu Ser Lys Gln Met Glu
1               5                   10                  15

Glu Ala Val Arg Leu Phe Ile Glu Trp Leu Lys Asn Gly Gly Lys
            20                  25                  30

<210> SEQ ID NO 15
<211> LENGTH: 31
<212> TYPE: PRT
<213> ORGANISM: Artificial Sequence
<220> FEATURE:
<223> OTHER INFORMATION: Ex4(1-30)K(Ste)
<220> FEATURE:
<221> NAME/KEY: MISC_FEATURE
<222> LOCATION: (31)..(31)
<223> OTHER INFORMATION: Stearic acid conjugate

<400> SEQUENCE: 15

His Gly Glu Gly Thr Phe Thr Ser Asp Leu Ser Lys Gln Met Glu
1               5                   10                  15

Glu Ala Val Arg Leu Phe Ile Glu Trp Leu Lys Asn Gly Gly Lys
            20                  25                  30

<210> SEQ ID NO 16
<211> LENGTH: 31
<212> TYPE: PRT
<213> ORGANISM: Artificial Sequence
<220> FEATURE:
<223> OTHER INFORMATION: Ex(1-30)K(Ara)
<220> FEATURE:
<221> NAME/KEY: MISC_FEATURE
<222> LOCATION: (31)..(31)
<223> OTHER INFORMATION: Arachidic acid conjugate

<400> SEQUENCE: 16

His Gly Glu Gly Thr Phe Thr Ser Asp Leu Ser Lys Gln Met Glu
1               5                   10                  15

Glu Ala Val Arg Leu Phe Ile Glu Trp Leu Lys Asn Gly Gly Lys
            20                  25                  30

<210> SEQ ID NO 17
<211> LENGTH: 33
<212> TYPE: PRT
<213> ORGANISM: Artificial Sequence
<220> FEATURE:
<223> OTHER INFORMATION: Ex4(1-32)K(Val)
<220> FEATURE:
<221> NAME/KEY: MISC_FEATURE
<222> LOCATION: (33)..(33)
<223> OTHER INFORMATION: Valeric acid conjugate

<400> SEQUENCE: 17

His Gly Glu Gly Thr Phe Thr Ser Asp Leu Ser Lys Gln Met Glu
1               5                   10                  15

Glu Ala Val Arg Leu Phe Ile Glu Trp Leu Lys Asn Gly Gly Pro Ser
            20                  25                  30

Lys

<210> SEQ ID NO 18
<211> LENGTH: 33
<212> TYPE: PRT
<213> ORGANISM: Artificial Sequence
<220> FEATURE:
<223> OTHER INFORMATION: Ex4(1-32)K(Cpr)
<220> FEATURE:
<221> NAME/KEY: MISC_FEATURE
<222> LOCATION: (33)..(33)
<223> OTHER INFORMATION: Caprylic acid conjugate

<400> SEQUENCE: 18

His Gly Glu Gly Thr Phe Thr Ser Asp Leu Ser Lys Gln Met Glu
1               5                   10                  15

Glu Ala Val Arg Leu Phe Ile Glu Trp Leu Lys Asn Gly Gly Pro Ser
            20                  25                  30

Lys

<210> SEQ ID NO 19
<211> LENGTH: 33
<212> TYPE: PRT
<213> ORGANISM: Artificial Sequence
<220> FEATURE:
<223> OTHER INFORMATION: Ex4(1-32)K(Cap)
<220> FEATURE:
<221> NAME/KEY: MISC_FEATURE
<222> LOCATION: (33)..(33)
<223> OTHER INFORMATION: Capric acid conjugate

<400> SEQUENCE: 19

His Gly Glu Gly Thr Phe Thr Ser Asp Leu Ser Lys Gln Met Glu
1               5                   10                  15

Glu Ala Val Arg Leu Phe Ile Glu Trp Leu Lys Asn Gly Gly Pro Ser
            20                  25                  30

Lys

<210> SEQ ID NO 20
<211> LENGTH: 33
<212> TYPE: PRT
<213> ORGANISM: Artificial Sequence
<220> FEATURE:

<223> OTHER INFORMATION: Ex4(1-32)K(Lau)
<220> FEATURE:
<221> NAME/KEY: MISC_FEATURE
<222> LOCATION: (33)..(33)
<223> OTHER INFORMATION: Lauric acid conjugate

<400> SEQUENCE: 20

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Lys

<210> SEQ ID NO 21
<211> LENGTH: 33
<212> TYPE: PRT
<213> ORGANISM: Artificial Sequence
<220> FEATURE:
<223> OTHER INFORMATION: Ex4(1-32)K(Myr)
<220> FEATURE:
<221> NAME/KEY: MISC_FEATURE
<222> LOCATION: (33)..(33)
<223> OTHER INFORMATION: Myristic acid conjugate

<400> SEQUENCE: 21

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Lys

<210> SEQ ID NO 22
<211> LENGTH: 33
<212> TYPE: PRT
<213> ORGANISM: Artificial Sequence
<220> FEATURE:
<223> OTHER INFORMATION: Ex4(1-32)K(Pal)
<220> FEATURE:
<221> NAME/KEY: MISC_FEATURE
<222> LOCATION: (33)..(33)
<223> OTHER INFORMATION: Palmitic acid conjugate

<400> SEQUENCE: 22

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Lys

<210> SEQ ID NO 23
<211> LENGTH: 33
<212> TYPE: PRT
<213> ORGANISM: Artificial Sequence
<220> FEATURE:
<223> OTHER INFORMATION: Ex4(1-32)K(Ste)
<220> FEATURE:
<221> NAME/KEY: MISC_FEATURE
<222> LOCATION: (33)..(33)
<223> OTHER INFORMATION: Stearic acid conjugate

<400> SEQUENCE: 23

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Lys

<210> SEQ ID NO 24
<211> LENGTH: 33
<212> TYPE: PRT
<213> ORGANISM: Artificial Sequence
<220> FEATURE:
<223> OTHER INFORMATION: Ex4(1-32)K(Ara)
<220> FEATURE:
<221> NAME/KEY: MISC_FEATURE
<222> LOCATION: (33)..(33)
<223> OTHER INFORMATION: Arachidic acid conjugate

<400> SEQUENCE: 24

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Lys

<210> SEQ ID NO 25
<211> LENGTH: 33
<212> TYPE: PRT
<213> ORGANISM: Artificial Sequence
<220> FEATURE:
<223> OTHER INFORMATION: Precursor to Ex4(1-32)K(Cap)
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (1)..(1)
<223> OTHER INFORMATION: tert-butyl
<220> FEATURE:
<221> NAME/KEY: MOD_RES
<222> LOCATION: (3)..(3)
<223> OTHER INFORMATION: tert-butyl
<220> FEATURE:
<221> NAME/KEY: MOD_RES
<222> LOCATION: (5)..(5)
<223> OTHER INFORMATION: tert-butyl
<220> FEATURE:
<221> NAME/KEY: MOD_RES
<222> LOCATION: (7)..(9)
<223> OTHER INFORMATION: tert-butyl
<220> FEATURE:
<221> NAME/KEY: MOD_RES
<222> LOCATION: (11)..(11)
<223> OTHER INFORMATION: tert-butyl
<220> FEATURE:
<221> NAME/KEY: MOD_RES
<222> LOCATION: (12)..(12)
<223> OTHER INFORMATION: t-butyloxycarbonyl
<220> FEATURE:
<221> NAME/KEY: MOD_RES
<222> LOCATION: (13)..(13)
<223> OTHER INFORMATION: tert-butyl
<220> FEATURE:
<221> NAME/KEY: MOD_RES
<222> LOCATION: (15)..(17)
<223> OTHER INFORMATION: tert-butyl
<220> FEATURE:
<221> NAME/KEY: MOD_RES
<222> LOCATION: (20)..(20)
<223> OTHER INFORMATION: pbf
<220> FEATURE:
<221> NAME/KEY: MOD_RES
<222> LOCATION: (24)..(24)
<223> OTHER INFORMATION: tert-butyl
<220> FEATURE:
<221> NAME/KEY: MOD_RES
<222> LOCATION: (25)..(25)

```
<223> OTHER INFORMATION: t-butyloxycarbonyl
<220> FEATURE:
<221> NAME/KEY: MOD_RES
<222> LOCATION: (27)..(27)
<223> OTHER INFORMATION: t-butyloxycarbonyl
<220> FEATURE:
<221> NAME/KEY: MOD_RES
<222> LOCATION: (28)..(28)
<223> OTHER INFORMATION: tert-butyl
<220> FEATURE:
<221> NAME/KEY: MOD_RES
<222> LOCATION: (33)..(33)
<223> OTHER INFORMATION: 1-(4,4-Dimethyl-2,6-dioxocyclohexylidene)ethyl
<220> FEATURE:
<221> NAME/KEY: MOD_RES
<222> LOCATION: (33)..(33)
<223> OTHER INFORMATION: trityl resin

<400> SEQUENCE: 25

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Lys

<210> SEQ ID NO 26
<211> LENGTH: 33
<212> TYPE: PRT
<213> ORGANISM: Artificial Sequence
<220> FEATURE:
<223> OTHER INFORMATION: Intermediate compound for production of
      Ex4(1-32)K-Cap
<220> FEATURE:
<221> NAME/KEY: MOD_RES
<222> LOCATION: (1)..(1)
<223> OTHER INFORMATION: BLOCKED
<220> FEATURE:
<221> NAME/KEY: MISC_FEATURE
<222> LOCATION: (1)..(1)
<223> OTHER INFORMATION: tert-butyl
<220> FEATURE:
<221> NAME/KEY: MISC_FEATURE
<222> LOCATION: (3)..(3)
<223> OTHER INFORMATION: tert-butyl
<220> FEATURE:
<221> NAME/KEY: MISC_FEATURE
<222> LOCATION: (5)..(5)
<223> OTHER INFORMATION: tert-butyl
<220> FEATURE:
<221> NAME/KEY: MISC_FEATURE
<222> LOCATION: (7)..(9)
<223> OTHER INFORMATION: tert-butyl
<220> FEATURE:
<221> NAME/KEY: MISC_FEATURE
<222> LOCATION: (11)..(11)
<223> OTHER INFORMATION: tert-butyl
<220> FEATURE:
<221> NAME/KEY: MISC_FEATURE
<222> LOCATION: (12)..(12)
<223> OTHER INFORMATION: t-butyloxycarbonyl
<220> FEATURE:
<221> NAME/KEY: MISC_FEATURE
<222> LOCATION: (13)..(13)
<223> OTHER INFORMATION: tert-butyl
<220> FEATURE:
<221> NAME/KEY: MISC_FEATURE
<222> LOCATION: (15)..(17)
<223> OTHER INFORMATION: tert-butyl
<220> FEATURE:
<221> NAME/KEY: MISC_FEATURE
<222> LOCATION: (20)..(20)
<223> OTHER INFORMATION: pbf
<220> FEATURE:
<221> NAME/KEY: MISC_FEATURE
<222> LOCATION: (24)..(24)
```

```
<223> OTHER INFORMATION: tert-butyl
<220> FEATURE:
<221> NAME/KEY: MISC_FEATURE
<222> LOCATION: (25)..(25)
<223> OTHER INFORMATION: t-butyloxycarbonyl
<220> FEATURE:
<221> NAME/KEY: MISC_FEATURE
<222> LOCATION: (27)..(27)
<223> OTHER INFORMATION: t-butyloxycarbonyl
<220> FEATURE:
<221> NAME/KEY: MISC_FEATURE
<222> LOCATION: (28)..(28)
<223> OTHER INFORMATION: tert-butyl
<220> FEATURE:
<221> NAME/KEY: MISC_FEATURE
<222> LOCATION: (33)..(33)
<223> OTHER INFORMATION: trityl resin

<400> SEQUENCE: 26

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Lys

<210> SEQ ID NO 27
<211> LENGTH: 33
<212> TYPE: PRT
<213> ORGANISM: Artificial Sequence
<220> FEATURE:
<223> OTHER INFORMATION: Ex4(1-32)K(Cap) intermediate compound
<220> FEATURE:
<221> NAME/KEY: MOD_RES
<222> LOCATION: (1)..(1)
<223> OTHER INFORMATION: BLOCKED
<220> FEATURE:
<221> NAME/KEY: MISC_FEATURE
<222> LOCATION: (1)..(1)
<223> OTHER INFORMATION: tert-butyl
<220> FEATURE:
<221> NAME/KEY: MISC_FEATURE
<222> LOCATION: (3)..(3)
<223> OTHER INFORMATION: tert-butyl
<220> FEATURE:
<221> NAME/KEY: MISC_FEATURE
<222> LOCATION: (5)..(5)
<223> OTHER INFORMATION: tert-butyl
<220> FEATURE:
<221> NAME/KEY: MISC_FEATURE
<222> LOCATION: (7)..(9)
<223> OTHER INFORMATION: tert-butyl
<220> FEATURE:
<221> NAME/KEY: MISC_FEATURE
<222> LOCATION: (11)..(11)
<223> OTHER INFORMATION: tert-butyl
<220> FEATURE:
<221> NAME/KEY: MISC_FEATURE
<222> LOCATION: (12)..(12)
<223> OTHER INFORMATION: t-butyloxycarbonyl
<220> FEATURE:
<221> NAME/KEY: MISC_FEATURE
<222> LOCATION: (13)..(13)
<223> OTHER INFORMATION: tert-butyl
<220> FEATURE:
<221> NAME/KEY: MISC_FEATURE
<222> LOCATION: (15)..(17)
<223> OTHER INFORMATION: tert-butyl
<220> FEATURE:
<221> NAME/KEY: MISC_FEATURE
<222> LOCATION: (20)..(20)
<223> OTHER INFORMATION: pbf
<220> FEATURE:
<221> NAME/KEY: MISC_FEATURE
<222> LOCATION: (24)..(24)
<223> OTHER INFORMATION: tert-butyl
```

```
<220> FEATURE:
<221> NAME/KEY: MISC_FEATURE
<222> LOCATION: (25)..(25)
<223> OTHER INFORMATION: t-butyloxycarbonyl
<220> FEATURE:
<221> NAME/KEY: MISC_FEATURE
<222> LOCATION: (27)..(27)
<223> OTHER INFORMATION: t-butyloxycarbonyl
<220> FEATURE:
<221> NAME/KEY: MISC_FEATURE
<222> LOCATION: (28)..(28)
<223> OTHER INFORMATION: tert-butyl
<220> FEATURE:
<221> NAME/KEY: MISC_FEATURE
<222> LOCATION: (33)..(33)
<223> OTHER INFORMATION: Capric acid-OH

<400> SEQUENCE: 27

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Lys

<210> SEQ ID NO 28
<211> LENGTH: 33
<212> TYPE: PRT
<213> ORGANISM: Artificial Sequence
<220> FEATURE:
<223> OTHER INFORMATION: Ex4(1-32)K(Cap) intermediate compound
<220> FEATURE:
<221> NAME/KEY: MISC_FEATURE
<222> LOCATION: (33)..(33)
<223> OTHER INFORMATION: Capric acid hydroxyl (TFA form)

<400> SEQUENCE: 28

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Lys

<210> SEQ ID NO 29
<211> LENGTH: 33
<212> TYPE: PRT
<213> ORGANISM: Artificial Sequence
<220> FEATURE:
<223> OTHER INFORMATION: Ex(1-32)K(Cap) AcOH form
<220> FEATURE:
<221> NAME/KEY: MISC_FEATURE
<222> LOCATION: (33)..(33)
<223> OTHER INFORMATION: Capric acid -OH (AcOH form)

<400> SEQUENCE: 29

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Lys
```